United States Patent
Mazaleyrat et al.

(10) Patent No.: US 11,261,438 B2
(45) Date of Patent: Mar. 1, 2022

(54) MEVALONATE DIPHOSPHATE DECARBOXYLASE VARIANTS

(71) Applicants: Global Bioenergies, Evry (FR); Scientist of Fortune S.A., Luxembourg (LU)

(72) Inventors: Sabine Mazaleyrat, Bois le Roi (FR); Marc Delcourt, Paris (FR); Maria Anissimova, Nozay (FR); Philippe Marliere, Tournai (BE)

(73) Assignees: Global Bioenergies, Evry (FR); Scientist of Fortune, S.A., Luxembourg (LU)

( * ) Notice: Subject to any disclaimer, the term of this patent is extended or adjusted under 35 U.S.C. 154(b) by 164 days.

(21) Appl. No.: 14/903,945

(22) PCT Filed: Jul. 9, 2014

(86) PCT No.: PCT/EP2014/064767
§ 371 (c)(1),
(2) Date: Jan. 8, 2016

(87) PCT Pub. No.: WO2015/004211
PCT Pub. Date: Jan. 15, 2015

(65) Prior Publication Data
US 2016/0160204 A1  Jun. 9, 2016

(30) Foreign Application Priority Data

Jul. 9, 2013  (EP) ..................... 13175790

(51) Int. Cl.
*C12N 9/88* (2006.01)
*C12P 5/02* (2006.01)
*C12P 7/04* (2006.01)

(52) U.S. Cl.
CPC ............. *C12N 9/88* (2013.01); *C12P 5/026* (2013.01); *C12P 7/04* (2013.01); *C12Y 401/01033* (2013.01)

(58) Field of Classification Search
None
See application file for complete search history.

(56) References Cited

U.S. PATENT DOCUMENTS

| 6,699,703 B1 * | 3/2004 | Doucette-Stamm ... C07H 21/04 435/252.3 |
| 9,193,978 B2 * | 11/2015 | Delcourt .................. C12N 9/88 |
| 2011/0165644 A1 | 7/2011 | Marliere |

FOREIGN PATENT DOCUMENTS

| WO | 2011076261 A1 | 6/2011 |
| WO | 2012052427 A1 | 4/2012 |

OTHER PUBLICATIONS

NCBI Reference Sequence : WP_000373467.1 ; May 14, 2013. (Year: 2013).*
NCBI Reference Sequence WP_000375267.1 (Downloaded Aug. 14, 2019) Available online May 14, 2013. (Year: 2013).*
NCBI Blastprotein Sequence PDF printout. Comparision of SEQ ID No.: 1 with WP_000375367.1 (Year: 2019).*
Hoskins et al. "Genome of the Bacterium Steptococcus pneumoniae Strain R6", Journal of Bacteriology 183(19): 5709-5717 (Year: 2001).*
GenBank sequence submission EHI65991; Oct. 10, 2011 (Year: 2011).*
International Preliminary Report from corresponding PCT/EP2014/064767, dated Feb. 2, 2016.
International Search Report received in POT/EP2014/064767 dated Jan. 20, 2015.
European Search Report received in EP 13 17 5790 dated Mar. 7, 2014.
Gogerty et al., "Formation of Isobutene from 3-Hydroxy-3-Methylbutyrate by Diphosphomevalonate Decarboxylase", vol. 76, No. 24, XP-002680645, Applied and Environmental Microbiology, American Society for Microbiology, Dec. 1, 2010, pp. 8004-8010.

* cited by examiner

*Primary Examiner* — Anand U Desai
(74) *Attorney, Agent, or Firm* — Michele M Wales; Inhouse Patent Counsel, LLC

(57) ABSTRACT

Described are mevalonate diphosphate decarboxylase variants having improved activity in converting 3-phosphonoxyisovalerate into isobutene. Such variants can be employed in processes for biologically producing isobutene from 3-hydroxyisovalerate or from 3-hydroxy-3-methylbutyrate into isobutene, for biologically producing isoprenol from mevalonate or from mevalonate-3-phosphate or for biologically producing 1,3-butadiene from 3-hydroxypent-4-enoate or from 3-phosphonoxypent-4-enoate.
Also described is an enzyme which is characterized in that it is capable of converting 3-phosphonoxyisovalerate into isobutene with a kcat of more than 0.1 $s^{-1}$.

22 Claims, 16 Drawing Sheets

Figure 1:
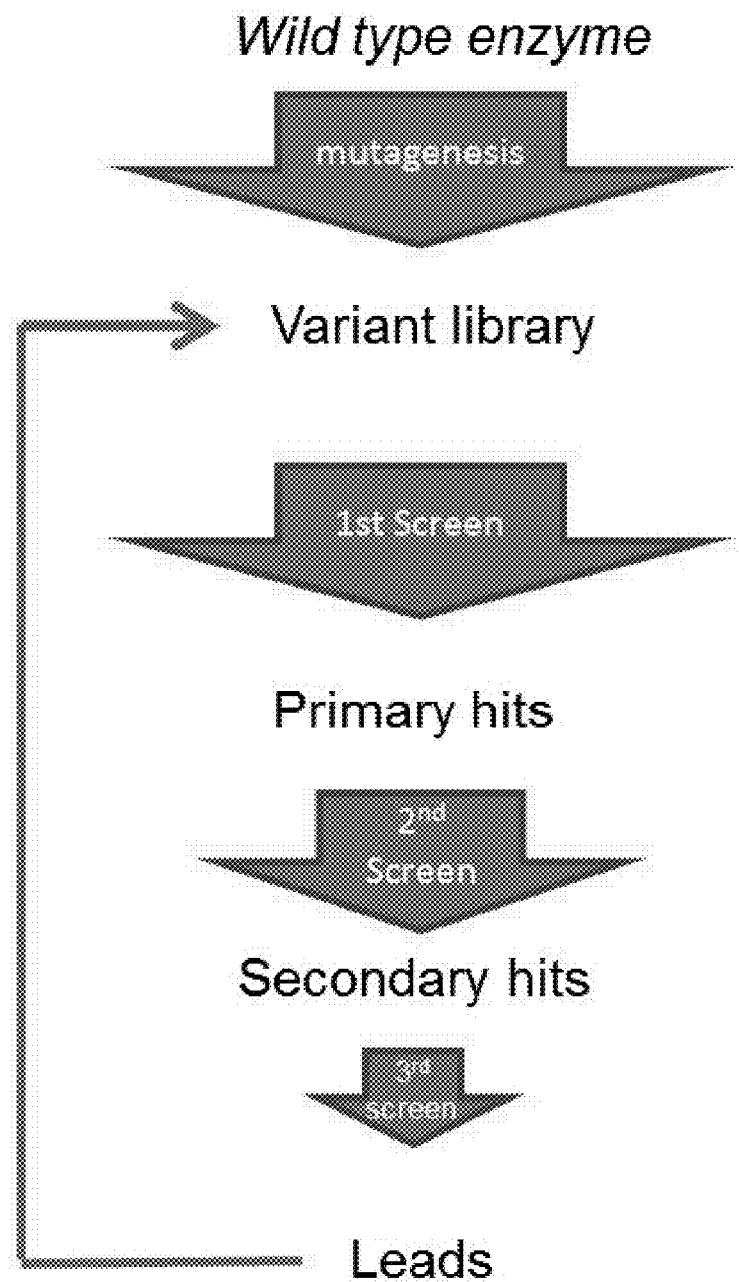

Specification includes a Sequence Listing.

FIG. 10

MEVALONATE DIPHOSPHATE DECARBOXYLASE VARIANTS

This Application is a 371 National Phase filing of PCT/EP2014/064767 filed Jul. 9, 2014, which claims foreign priority of 13175790.8, filed Jul. 9, 2013, which are all incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 13, 2018 is named GB-17-US_Revised_Sequence_Listing_ST25.txt and is 63,023 bytes in size.

The present invention relates to mevalonate diphosphate decarboxylase variants having improved activity in converting 3-phosphonoxyisovalerate into isobutene. Moreover, the present invention relates to enzymes which are characterized in that they are capable of converting 3-phosphonoxyisovalerate into isobutene with a kcat of more than 0.1 $s^{-1}$.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels. Over the past years, the bioproduction of plastics ("bioplastics") and biofuels has become a thriving field due to economic concerns linked to the price of oil; and to environmental considerations that are both global (carbon-neutral products) and local (waste management). Thus, there is a need for efficient enzymes for producing alkenes such as isobutene.

WO 2010/001078 describes a process for producing alkenes; such as isobutene, by enzymatic conversion of 3-hydroxyalkanoic acids with an enzyme having the activity of a decarboxylase, for example a mevalonate diphosphate (MDP) decarboxylase. Such a method is advantageous because it helps to avoid the use of petroleum products, to lower the costs of producing plastics and fuels and can have a considerable global environmental impact by allowing carbon to be stored in solid form. It could be shown that mevalonate diphosphate decarboxylase is capable of using substrates other than its natural substrate mevalonate diphosphate, in particular 3-hydroxyalkanoic acids; and convert them into terminal alkenes. Mevalonate diphosphate (MDP) decarboxylase (enzyme nomenclature EC 4.1.1.33) is an enzyme involved in cholesterol biosynthesis. The enzyme has been isolated from a variety of organisms including animals, fungi; yeasts and some bacteria. It can also be expressed by some plants (Lalitha et al., Phytochemistry 24 (11), (1985), 2569-2571). Many genes encoding this enzyme have been cloned and sequenced. These enzymes are generally composed of 300 to 400 amino acids and use ATP as co-substrate, which is converted during the reaction to ADP and inorganic phosphate. The phosphate group is transferred in a first step from the ATP molecule to the tertiary alcohol of mevalonate diphosphate, releasing ADP. The reaction intermediate, which is phosphorylated on the 3-hydroxyl group, undergoes in a second step elimination of the phosphate group and decarboxylation, in the physiological case releasing isopentenyl diphosphate.

MDP decarboxylases have been isolated from a multitude of different organisms, eukaryotic and prokaryotic, and have been analyzed and characterized in detail. Also, various mutants have been produced in order to identify the amino acid residues which may play a crucial role in the enzymatic activity of the enzyme, For example, Alvear et al, (Biochemistry 21 (1982), 4646-4650) describe the purification and characterization of avian liver MDP decarboxylase and Dhe-Paganon et al. (Biochemistry 33 (1994), 13355-13362) describe the mechanism of the reaction catalyzed by MDP decarboxylase. Berges et al. (J. Bacteriol. 179 (1997), 4664-4670) reported on a mutation of the *S. cerevisiae* MDP decarboxylase which leads to thermosensitivity. Krepkiy and Miziorko (Protein Sci. 13 (2004), 1875-1881) identified active site residues in MDP decarboxylase of yeast and analysed mutations which led to a reduction in activity. Similarly, Krepkiy and Miziorko (Biochemistry 44 (2005), 2671-2677) investigated conserved serine residues which are located in a proposed interdomain active site cleft of MOP decarboxylase as to their relevance and could show that mutation of any of these serine residues leads to a reduction or loss of activity. Also Qiu et al. (Bioorganic & medicinal Chemistry Letters 17 (2007), 6164-6168) analyze MOP decarboxylase (of rat) and report on various mutants which lead to a reduction or loss of activity, Voynova et al, (Arch. Biochem. Biophys. 480 (2008), 58-67) characterized the human MDP decarboxylase and identified several amino acid residues which lead to a decrease or loss of enzyme activity.

Moreover, the crystal structure of several MOP decarboxylases and MDP decarboxylase mutants from different origins has been established, e.g. for the *Staphylococcus epidermidis* enzyme (Barta et al., J. Biol, Chem. 286 (2011), 23900-23910; Barta et al., Biochemistry 51 (2012), 5611-5621; PDB accession numbers 3QT5-6-7-8 and 4DPX, 4DPY, 4DPU, 4DPT, 4DU8, 4DU7 and 4DPW), for the *Trypanosoma brucei* and *Staphylococcus aureus* enzymes (Byres et al, J. Mol. Biol. 371 (2007), 540-553; PDB accession number 2HKE, 2HK2, 2HK3), the human enzyme (Voynova et al, (Arch. Biochem. Biophys. 480 (2008), 58-67; PDB accession number 3O4J), the *Streptococcus pyogenes* enzyme (FOB accession number 2G58), the mouse enzyme (PDB accession number 3FON), the *Legionella pneumophila* enzyme (PDB accession number 3LTO) and the *S. cerevisiae* enzyme (Bonanno et al., Proc. Natl. Acad. Sci. USA. 98 (2001), 12896-12901; PDB accession number 1F14).

Lefurgy et al. (J, Biol. Chem. 285 (2010), 20654-20663 analyzed the ligand binding pocket of MOP decarboxylase of *Streptococcus pneumoniae* by using a series of MDP analogues and Weerasinghe and Dassanayake (J. Mol. Model. 16 (2010) 489-498) reported on the simulation of structural and functional properties of MDP decarboxylase of *S. cerevisiae* using the wild-type enzyme and the thermosensitive mutant described in Berges et al. (J. Bacteriol. 179 (1997), 4664-4670). Byres et al. (J. Mol. Biol, 371 (2007), 540-553) compared the crystal structures of different MDP decarboxylases, in particular of those from *T. brucei*, *S, aureus* and *S. cerevisiae* and observe that the overall architecture of the enzyme remains conserved.

WO 2010/001078 discloses inter alia that it is possible to convert 3-hydroxy-3-methylbutyrate (or 3-hydroxyisovalerate) into isobutene by a decarboxylase, in particular an MDP decarboxylase. In this case, the reaction intermediate is 3-phosphonoxyisovalerate which is further converted in the second part of the reaction into isobutene. Gogerty et al. (Appl. Environ. Microbiol. 76 (2010), 8004-8010) also report on the formation of isobutene from 3-hydroxy-3-methylbutyrate using an MDP decarboxylase from *S. cerevisiae* and show that mutations at residues 145 and 74 of this enzyme, which are located within or close to the proposed active site of this enzyme, lead to an increase of the conversion of 3-hydroxy-3-methylbutyrate into isobutene. However, the level of production of isobutene achieved is still too low for commercial application.

Later works have shown that different MDP decarboxylases may show different efficiencies as regards the catalysis of the first and the second step of the reaction as described above, with some MDP decarboxylases showing a high activity in the first step and others showing a high activity in the second step. Therefore, it had been proposed to combine two MDP decarboxylases which show a high activity in the first and in the second step of the reaction, respectively, so as to optimize the overall enzymatic reaction (WO2012/052427).

However, although such a method allows to produce alkenes by enzymatically converting 3-hydroxyalkanoates (e.g. isobutene from 3-hydroxyisovalerate), there is still a need for improvements, in particular as regards a further increase in efficiency of the process so as to make it more suitable for industrial purposes.

The present application addresses this need by providing the embodiments as defined in the claims.

In particular, the present invention provides enzymes which are characterized in that they are capable of converting 3-phosphonoxyisovalerate into isobutene with a kcat of more than $0.01\ s^{-1}$ or $0.1\ s^{-1}$, preferably of more than $1\ s^{-1}$, more preferably of more than $10\ s^{-1}$, and even more preferably of more than $10^2\ s^{-1}$ or most preferably of more than $10^3\ s^{-1}$. Preferably such enzymes are variants of a mevalonate diphosphate decarboxylase, and even more preferably such enzymes have an amino acid sequence which shows more than 60% sequence homology to the amino acid sequence shown in SEQ ID NO:1. It is preferred that the enzymes according to the invention are non-naturally occurring enzymes. This means that they substantially differ from naturally occurring enzymes, in particular as regards their primary structure, i.e., the amino acid sequence. Thus, they show an amino acid sequence which does not occur in nature. It is preferable that such non-naturally occurring enzymes also differ from naturally occurring enzymes insofar that they have a higher enzymatic activity for the reactions described herein.

Thus, the present invention provides in particular variants of mevalonate diphosphate decarboxylase which show an improved activity as regards the conversion of 3-phosphonoxyisovalerate into isobutene thereby allowing to dramatically increase the production efficiency of isobutene from 3-hydroxyisovalerate.

The term "mevalonate diphosphate decarboxylase" in the context of the present invention refers to an enzyme which naturally has the ability to convert mevalonate diphosphate into isopentenyl diphosphate and which is classified as EC 4.1.1.33. The term "mevalonate diphosphate decarboxylase" also covers enzymes which are classified as a mevalonate diphosphate decarboxylase and which act on mevalonate monophosphate, i.e. which are mevalonate monophosphate decarboxylases. An example for such an enzyme is the enzyme from *Roseiflexus* sp. (strain RS-1) (Uniprot Accession number: A5V173) which is classified as a mevalonate diphosphate decarboxylase. Since some bacteria from *Roseiflexus* genus, e.g. *Roseiflexus castenholzii*, have been reported to have an alternative mevalonate pathway which involves the action of a mevalonate monophosphate decarboxylase an enzyme from *Roseiflexus* sp. may act as a mevalonate monophosphate decarboxylase. Additionally, a third mevalonate pathway has recently been described in *T. acidophilum*. In this pathway, the formation of isopentenyl monophosphate probably occurs through mevalonate-3,5-pyrophosphate (MVA-3,5-PP). The two genes which can be implicated in the decarboxylation of this intermediate are Ta0461 and Ta0893. These genes can be associated to the family of diphosphomevalonate decarboxylase referenced in InterPro database as IPR005935 (http://www.ebi.ac.uk/interpro/entry/IPR005935). but these two enzymes may act as mevalonate-3,5-pyrophosphate decarboxylase. Thus, the term "mevalonate diphosphate decarboxylase" also covers such enzymes. The present invention relates to variants which are derived from a mevalonate diphosphate decarboxylase. The variants of such an enzyme according to the present invention are characterized by the feature that they are derived from an MDP decarboxylase having the amino acid sequence shown in SEQ ID NO:1 or having a related sequence (at least 40% identical, preferably at least 50% identical, even more preferably at least 60% or at least 90% identical) and in which mutations are effected at one or more of the positions as indicated herein below and by the feature that they show the ability to convert 3-phosphonoxyisovalerate into isobutene and that they can do this with an improved activity. In a preferred embodiment the variant according to the present invention is derived from a sequence which shows at least 80% sequence identity to SEQ ID NO:1 and in which one or more substitutions and/or deletions and/or insertions at the positions indicated herein below have been effected.

Given the high conservation between MDP decarboxylases, the teaching of the present invention is not restricted to the enzyme of *S. mitis* (represented by SEQ ID NO: 1) but can be extended to MDP decarboxylases from other organisms. Thus, the present invention also relates to variants of MDP decarboxylase which are derived from enzymes which are structurally related to the *S. mitis* sequence and which show one or more substitutions and/or deletions and/or insertions at positions corresponding to any of the positions as indicated herein-below. The term "structurally related" refers to MDP decarboxylases which show a sequence identity of at least n % to the sequence shown in SEQ ID NO: 1 with n being an integer between 40 and 100, preferably 40, 45, 50, 55, 60, 65, 70, 75, 80, 85, 90, 91, 92, 93, 94, 95, 96, 97, 98 or 99. In a preferred embodiment the structurally related MDP decarboxylase is of prokaryotic origin. These variants are characterized by the feature that they show the ability to convert 3-phosphonoxyisovalerate into isobutene and that they can do this with an improved activity when compared to the enzyme from which these variants are derived. Even more preferably such variants also show an improved activity when compared to the enzyme having the amino acid sequence shown in SEQ ID NO:1.

Thus, in one embodiment the variant of MDP decarboxylase according to the present invention has or preferably is derived from a sequence which is at least n % identical to SEQ ID NO:1 with n being an integer between 40 and 100, preferably 40, 45, 50, 55, 60, 65, 70, 75, 80, 85, 90, 91, 92, 93, 94, 95, 96, 97, 98 or 99, and it has (a) substitution(s) and/or (a) deletion(s) and/or (an) insertion(s) at a position as indicated below. When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 40%, 50% or 60% or 90% identical to a reference sequence default settings may be used or the settings are preferably as follows: Matrix: blosum 30; Open gap penalty: 10,0; Extend gap penalty: 0,05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

Examples for MDP decarboxylases which show a sequence identity of at least 60%, in particular between 60% and 80%, to SEQ ID NO:1 are shown in the following Table.

TABLE 1

| Entry name UniprotKb | Accession | Organism | Entry date | Last Database update | Entry version | Sequence version | % identity with SEQ ID NO: 1 |
|---|---|---|---|---|---|---|---|
| F5U3H6_STRAP (SEQ ID NO: 5) | F5U3H6 | Streptococcus anginosus SK52 | Jul. 27, 2011 | Oct. 19, 2011 | 3 | 1 | 77 |
| A8AUU9_STRGC (SEQ ID NO: 6) | A8AUU9 | Streptococcus gordonii (strain Challis/ ATCC 35105/ CH1/DL1/ V288) | Oct. 23, 2011 | Oct. 19, 2011 | 29 | 1 | 74 |
| F2C8L7_STRSA (SEQ ID NO: 7) | F2C8L7 | Streptococcus sanguinis SK330 | May 31, 2011 | Oct. 19, 2011 | 4 | 1 | 74 |
| E7S990_9STRE (SEQ ID NO: 8) | E7S990 | Streptococcus australis ATCC 700641 | Apr. 5, 2011 | Oct. 19, 2011 | 4 | 1 | 71 |
| E7S3Q3_STRAG (SEQ ID NO: 9) | E7S3Q3 | Streptococcus agalactiae ATCC 13813 | Apr. 5, 2011 | Oct. 19, 2011 | 4 | 1 | 71 |
| F0VY81_STRG2 (SEQ ID NO: 10) | F0VY81 | Streptococcus gallolyticus (strain ATCC BAA-2069) | May 3, 2011 | Oct. 19, 2011 | 5 | 1 | 71 |
| B9DU65_STRU0 (SEQ ID NO: 11) | B9DU65 | Streptococcus uberis (strain ATCC BAA-854/0140J) | Mar. 24, 2009 | Oct. 19, 2011 | 21 | 1 | 70 |
| E8JNQ3_STREI (SEQ ID NO: 12) | E8JNQ3 | Streptococcus equinus ATCC 9812 | Apr. 5, 2011 | Oct. 19, 2011 | 4 | 1 | 70 |
| E0PWI4_STRPY (SEQ ID NO: 13) | E0PWI4 | Streptococcus pyogenes ATCC 10782 | Nov. 2, 2010 | Oct. 19, 2011 | 7 | 1 | 70 |
| Q9FD58_STRPY (SEQ ID NO: 14) | Q9FD58 | Streptococcus pyogenes | Mar. 27, 2001 | Oct. 19, 2011 | 49 | 1 | 70 |
| D0GIF6_9FUSO (SEQ ID NO: 15) | D0GIF6 | Leptotrichia goodfellowii F0264 | Dec. 15, 2009 | Oct. 19, 2011 | 19 | 1 | 62 |

Examples for MDP decarboxylases which show a sequence identity of at least 80%, in particular between 80% and 90%, to SEQ ID NO:1 are shown in the following Table.

alignments, the following settings are preferably chosen: Protein weight matrix: BLOSUM 62; gap open: 10; gap extension: 0.2; gap distance: 5; no end gap.

TABLE 2

| Entry name UniprotKb | Accession | Organism | Entry date | Last update | Entry version | Sequence version | % identity with SEQ ID NO: 1 |
|---|---|---|---|---|---|---|---|
| E8KA62_9STRE | E8KA62 (SEQ ID NO: 16) | Streptococcus peroris ATCC700780 | Apr. 5, 2011 | Oct. 19, 2011 | 5 | 1 | 89 |
| E8JYA8_9STRE | E8JYA8 (SEQ ID NO: 17) | Streptococcus infantis ATCC700779 | Apr. 5, 2011 | Oct. 19, 2011 | 4 | 1 | 88 |
| F5VZT1_9STRE | F5VZT1 (SEQ ID NO: 18) | Streptococcus infantis SK1076 | Jul. 27, 2011 | Oct. 19, 2011 | 3 | 1 | 88 |

Examples for MDP decarboxylases which show a sequence identity of at least 90%, in particular between 90% and 100%, to SEQ ID NO:1 are shown in the following Table.

When the amino acid sequences of MDP decarboxylases are aligned by means of such a method, regardless of insertions or deletions that occur in the amino acid sequences, the positions of the corresponding amino acid

TABLE 3

| Entry name UniprotKb | Accession | Organism | Entry date | Last update | Entry version | Sequence version | % identity with SEQ ID NO: 1 |
|---|---|---|---|---|---|---|---|
| E1LJG7_STRMT | E1LJG7 (SEQ ID NO: 19) | Streptococcus mitis SK321 | Nov. 30, 2010 | Oct. 19, 2011 | 8 | 1 | 96 |
| E9FM52_9STRE | E9FM52 (SEQ ID NO: 20) | Streptococcus sp M334 | Apr. 5, 2011 | Oct. 19, 2011 | 5 | 1 | 95 |
| E6KKU6_STRSA | E6KKU6 (SEQ ID NO: 21) | Streptococcus sanguinis ATCC 49296 | Mar. 8, 2011 | Oct. 19, 2011 | 4 | 1 | 95 |
| D4FR73-STROR | D4FR73 (SEQ ID NO: 22) | Streptococcus oralis ATCC 35037 | May 18, 2010 | Oct. 19, 2011 | 9 | 1 | 94 |
| Q8DR50_STRR6 | Q8DR50 (SEQ ID NO: 23) | Streptococcus pneumonia ATCC BAA-255/R6 | Mar. 1, 2003 | Oct. 19, 2011 | 58 | 1 | 94 |

Amino acid residues located at a position corresponding to a position as indicated herein-below in the amino acid sequence shown in SEQ ID NO:1 can be identified by the skilled person by methods known in the art. For example, such amino acid residues can be identified by aligning the sequence in question with the sequence shown in SEQ ID NO:1 and by identifying the positions which correspond to the above indicated positions of SEQ ID NO: 1. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/ residues can be determined in each of the MDP decarboxylases. Examples of alignments are provided in FIGS. 10 to 12.

In the context of the present invention, "substituted with another amino acid residue" means that the respective amino acid residues at the indicated position can be substituted with any other possible amino acid residues, e.g. naturally occurring amino acids or non-naturally occurring amino acids (Brustad and Arnold, Curr. Opin. Chem. Biol. 15 (2011), 201-210), preferably with an amino acid residue selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Preferred substitutions for certain positions are indicated further below. Moreover, the term "substituted" or "substitution" also means that the respective amino acid residue at the indicated position is modified.

Such modifications include naturally occurring modifications and non-naturally occurring modifications. Naturally occurring modifications include but are not limited to eukaryotic post-translational modification, such as attachment of functional groups (e.g. acetate, phosphate, hydroxyl, lipids (myristoylation of glycine residues) and carbohydrates (e.g. glycosylation of arginine, asparagines etc.). Naturally occurring modifications also encompass the change in the chemical structure by citrullination, carbamylation and disulphide bond formation between cysteine residues; attachment of co-factors (FMN or FAD that can be covalently attached) or the attachment of peptides (e.g. ubiquitination or sumoylation).

Non-naturally occurring modifications include, e.g., in vitro modifications such as biotinylation of lysine residue or the inclusion of non-canonical amino acids (see Liu and Schultz, Annu. Rev. Biochem. 79 (2010), 413-44 and Wang et al., Chem. Bio. 2009 Mar. 27; 16 (3), 323-336; doi: 101016/jchembiol.2009.03.001).

In the context of the present invention, "deleted" or "deletion" means that the amino acid at the corresponding position is deleted.

In the context of the present invention, "inserted" or "insertion" means that at the respective position one or two, preferably one amino acid residue is inserted, preferable in front of the indicated position.

Thus, the present invention relates to a variant of a mevalonate diphosphate decarboxylase showing an improved activity in converting 3-phosphonoxyisovalerate into isobutene over the corresponding mevalonate diphosphate decarboxylase from which it is derived, wherein the mevalonate diphosphate decarboxylase variant is characterized in that it shows one or more substitutions, deletions and/or insertions in comparison to the corresponding sequence from which it is derived and wherein these substitutions, deletions and/or insertions occur at one or more of the positions corresponding to positions 282, 9, 11, 16, 24, 28, 42, 43, 45, 53, 66, 77, 80, 91, 105, 116, 118, 120, 121, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315 in the amino acid sequence shown in SEQ ID NO:1. "Corresponding to" these positions means corresponding to any of these positions in a related sequence.

In a preferred embodiment the mevalonate diphosphate decarboxylase from which the variant is derived is a mevalonate diphosphate decarboxylase which shows the amino acid sequence as shown in SEQ ID NO:1 or an amino acid sequence having at least 40%, preferably at least 50% and even more preferably at least 60%, or most preferred at least 90% sequence identity to SEQ ID NO:1.

Accordingly, in one embodiment, the present invention relates to a variant of a mevalonate diphosphate decarboxylase having an amino acid sequence as shown in SEQ ID NO:1 or an amino acid sequence having at least 40%, 50%, 60% or 90% sequence identity to SEQ ID NO:1, wherein one or more amino acid residues at a position selected from the group consisting of positions 9, 11, 16, 24, 28, 42, 43, 45, 53, 66, 77, 80, 91, 105, 116, 118, 120, 121, 122, 123, 129, 134, 141, 159, 160, 161, 173, 177, 180, 186, 215, 238, 241, 242, 248, 251, 253, 258, 264, 279, 282, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315 in the amino acid sequence shown in SEQ ID NO:1 or at a position corresponding to any of these positions in a related sequence, are substituted with another amino acid residue or deleted or show an insertion at at least one of these positions and wherein said mevalonate diphosphate decarboxylase has improved activity in converting 3-phosphonoxyisovalerate into isobutene. In a preferred embodiment the deletion, insertion or substitution is at a position selected from the group consisting of positions 9, 11, 42, 43, 45, 66, 77, 116, 118, 120, 121, 123, 129, 134, 159, 160, 173, 177, 186, 251, 253, 282, 293, 297, 299, 303, 307 and 308.

The present inventors have found that the activity of a mevalonate diphosphate decarboxylase to catalyze the second step of the above described conversion of 3-hydroxyisovalerate into isobutene, i.e. the conversion of 3-phosphonoxyisovalerate into isobutene, can dramatically be improved by mutating the MDP decarboxylase enzyme at certain positions. They used as a model enzyme the enzyme from S. mitis, the sequence of which is shown in SEQ ID NO: 1. The identified single mutations lead to an increase of activity of up to more than 300% when compared to the unmutated sequence of the S. mitis enzyme (represented by SEQ ID NO: 1). Combining mutations led to a further increase of up to 750% and the identification of additional mutations in addition to these combinations allowed to achieve a further 16-fold increase.

In particular, the present inventors found that substitutions at positions 9, 11, 16, 24, 28, 42, 43, 45, 53, 66, 77, 80, 91, 105, 116, 118, 120, 121, 122, 123, 129, 134, 141, 159, 160, 161, 173, 177, 180, 186, 215, 238, 241, 242, 248, 251, 253, 258, 264, 279, 282, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, or 315 or substitutions at combinations of these positions lead to a drastic increase in the enzyme's ability to convert 3-phosphonoxyisovalerate into isobutene.

As indicated above, the variants of an MDP decarboxylase according to the present invention are characterized in that they show an increased activity in converting 3-phosphonoxyisovalerate into isobutene when compared to the MDP decarboxylase from which they are derived. Thus, in the case where the variant is derived from the MDP decarboxylase of S, mitis having the amino acid sequence shown in SEQ ID NO: 1, the variant shows an increased activity in converting 3-phosphonoxyisovalerate into isobutene when compared to the MDP decarboxylase shown in SEQ ID NO: 1, When the variant is derived from an MOP decarboxylase which is structurally related to the MDP decarboxylase of S. mitis as defined herein above, the variant shows an increased activity in converting 3-phosphonoxyisovalerate into isobutene when compared to the corresponding starting sequence into which the corresponding mutations have been introduced. In a particularly preferred embodiment such variants show also an increased activity in converting 3-phosphonoxyisovalerate into isobutene when compared to the MDP decarboxylase shown in SEQ ID NO: 1. The activity of converting 3-phosphonoxyisovalerate into isobutene may be determined by methods known to the person skilled in the art. In one embodiment, this activity is determined as described in the Examples appended hereto. In a particular embodiment this activity can be measured by using in particular the following assay:

A nucleic acid molecule encoding the respective enzyme is transformed into E. coli, such as E. coli BL21DE3 and the enzyme is expressed in E, coli. The activity of the enzyme can then be measured using either crude cell lysate (i.e. the cell culture is centrifuged, the cell pellet is resuspended in a hypotonic buffer, is sonicated or not but is not centrifuged); or the soluble fraction (i.e. the supernatant obtained following centrifugation of the crude cell lysate); or purified protein (i.e. recombinant protein which is present in the soluble fraction and which is, for example, trapped on a resin using chromatography).

The activity of the expressed enzyme is tested as follows:

A reaction mixture is prepared in glass GC vials by mixing the crude cell lysate, the soluble fraction or the purified protein as described above with 3-phosphonoxyisovalerate in 50 mM Tris pH 7 final concentration. ATP, $MgCl_2$ and KCl are provided as cofactors.

The vials are hermetically sealed and the reaction mixture is incubated for an appropriate time (e.g. 24 h) at 37° C. The isobutene produced by the reaction is determined by gas chromatography by injecting the gas phase obtained from the vial into a gas chromatograph. Controls in the assay are culture with untransformed bacteria, bacteria transformed with an empty expression vector and bacteria expressing the corresponding starting enzyme, e.g. the S. mitis enzyme showing the amino acid sequence as shown in SEQ ID NO:1.

The 3-phosphonoxyisovalerate used in the assay may be prepared in different ways. One possibility is to provide this compound by the following reaction:

0.063 mg/ml of purified Thermophilus acidophilum MDP decarboxylase is mixed with 50 mM hydroxyisovalerate, 40 mM ATP in a 50 mM Tris-Cl pH 7, 20 mM KCl, 20 mM $MgCl_2$ and incubated for 24 hours at 45° C. This enzymatically prepared 3-phosphonoxyisovalerate substrate is used in the reaction mixture.

Figure 9:
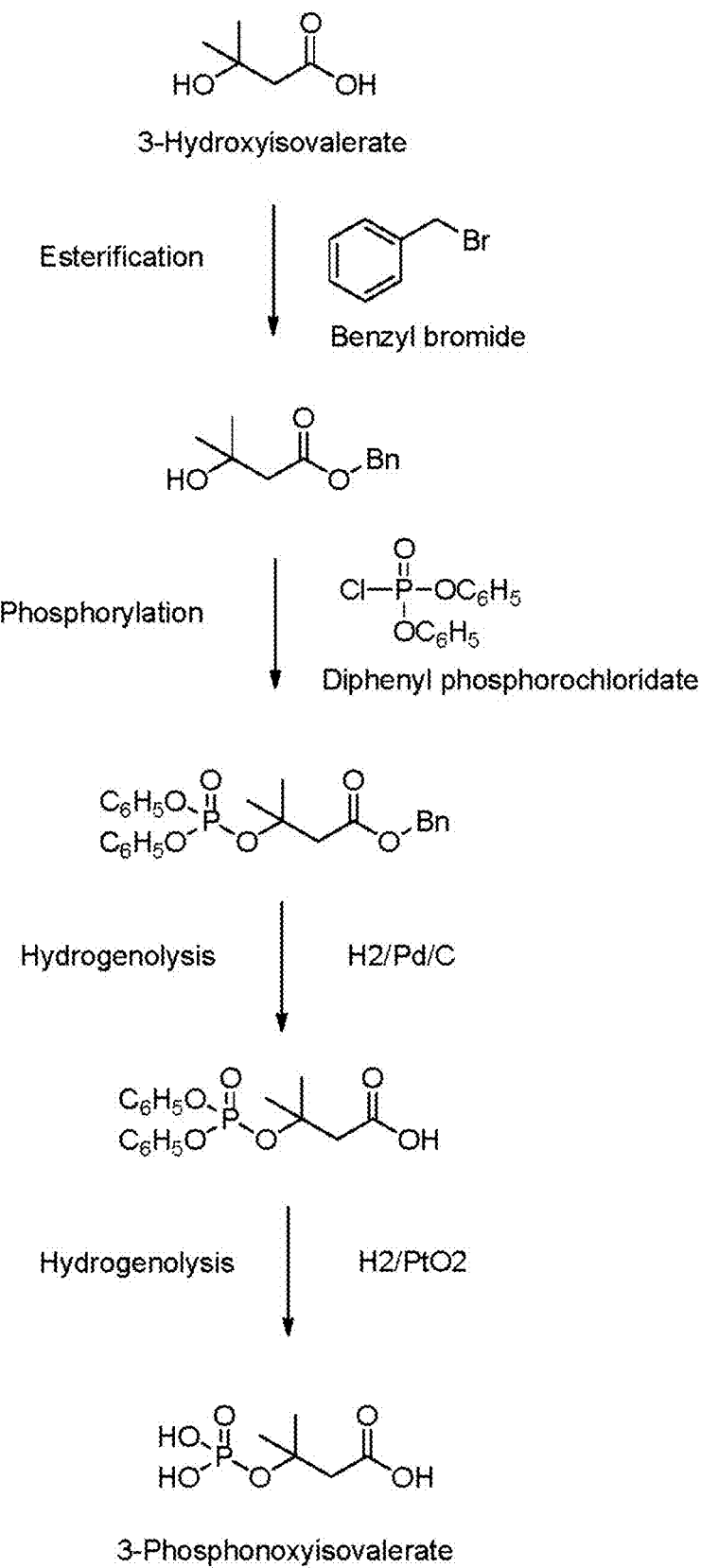

Another, preferred possibility is that the 3-phosphonoxyisovalerate used in the assay is chemically synthesized. The synthesis scheme is shown in FIG. 9.

If chemically synthesized 3-phosphonoxyisovalerate is used in the assay, the concentration is preferably between 3 and 8 mM, preferably it is 5 mM.

In a preferred assay for testing the enzyme activity purified enzyme is used. In this case, the reaction mixture contains 500 µg purified enzyme in 50 mM Tris HCl pH 7.5 and 3-phosphonoxyisovalerate (provided as described above)

It is made sure that cofactors such as ATP, $MgCl_2$ and KCl are present. The volume is adjusted to 500 µl with 50 mM Tris HCl pH 7.5 and the reaction is incubated for 15 hours at 37° C. Subsequently the isobutene produced is determined by gas chromatography.

In one embodiment, the 3-phosphonoxyisovalerate is prepared enzymatically as described above.

In a particularly preferred embodiment the 3-phosphonoxyisovalerate is chemically synthesized. In this case, the reaction mixture contains:

200 µg purified enzyme
3-phosphonoxyisovalerate
5 mM ATP, 20 mM KCl, 10 mM $MgCl_2$ and 50 mM Tris-Cl pH 7.5

In order to test the activity of the enzyme varying concentrations of 3-phosphonoxyisovalerate are used, preferably the following concentrations: 0.625 mM, 1.25 mM, 2.5 mM, 5 mM, 10, mM, 20 mM, 40 mM, 80 mM and 160 mM. It is particularly preferred that the concentration of 3-phosphonoxyisovalerate is 5 mM. The volume is adjusted to 500 µl with 50 mM Tris HCl pH 7.5 and the reaction is incubated for 15 hours at 37° C. Subsequently the isobutene produced is determined by gas chromatography.

Examples for such an assay to determine the activity of an enzyme to convert 3-phosphonoxyisovalerate into isobutene are given in the Example section below in Example 1.

In the context of the present invention, an "improved activity" means that the activity of the MDP decarboxylase in question is at least 10%, preferably at least 20%, more preferably at least 30% or 50%, even more preferably at least 70% or 80% and particularly preferred at least 90% or 100% higher than that of the MDP decarboxylase from which the variant is derived, preferably higher than that of the MDP decarboxylase of S. mitis represented by SEQ ID NO:1. In even more preferred embodiments the improved activity may be at least 150%, at least 200%, at least 300%, at least 750% or at least 1000% higher than that of the corresponding MDP decarboxylase from which the variant is derived, preferably higher than that of the MDP decarboxylase of S. mitis represented by SEQ ID NO:1 In a particularly preferred embodiment, the activity is measured by using an assay with purified enzyme and chemically synthesized 3-phosphonoxyisovalerate as described hereinabove. The improved activity of a variant can be measured as a higher isobutene production in a given time under defined conditions, compared with the parent enzyme. This improved activity can result from a higher kcat value. It can also result from a lower Km value. It can also result from a higher kcat/Km value. The degree of improvement can be measured as the improvement in isobutene production. The degree of improvement can also be measured in terms of kcat improvement, of kcat/Km improvement, or in terms of Km decrease.

According to one embodiment, the MOP decarboxylase of the present invention has an amino acid sequence in which (1) an amino acid residue at position 1 in the amino acid sequence shown in SEQ ID NO:1 or at a position corresponding to this position in a related sequence, is deleted or substituted with leucine; and/or (2) an amino acid residue at position 2 in the amino acid sequence shown in SEQ ID NO:1 or at a position corresponding to this position in a related sequence, is deleted or substituted with histidine; and/or (3) an amino acid residue at position 9 in the amino acid sequence shown in SEQ ID NO:1 or at a position corresponding to this position in a related sequence, is deleted or substituted with leucine; and/or (4) an amino acid residue at position 11 in the amino acid sequence shown in SEQ ID NO:1 or at a position corresponding to this position in a related sequence, is deleted or substituted with cysteine, glutamic acid or phenylalanine, preferably cysteine; and/or (5) an amino acid residue at position 16 in the amino acid sequence shown in SEQ ID NO:1 or at a position corresponding to this position in a related sequence, is deleted or substituted with leucine; and/or (6) an amino acid residue at position 23 in the amino acid sequence shown in SEQ ID NO:1 or at a position corresponding to this position in a related sequence, is deleted or substituted with leucine; and/or (7) an amino acid residue at position 24 in the amino acid sequence shown in SEQ ID NO:1 or at a position corresponding to this position in a related sequence, is deleted or substituted with arginine, serine, or leucine; and/or (8) an amino acid residue at position 28 in the amino acid sequence shown in SEQ ID NO:1 or at a position corresponding to this position in a related sequence, is deleted or substituted with lysine or alanine; and/or (9) an amino acid residue at position 31 in the amino acid sequence shown in SEQ ID NO:1 or at a position corresponding to this position in a related sequence, is deleted or substituted with serine; and/or

(10) an amino acid residue at position 42 in the amino acid sequence shown in SEQ ID NO:1 or at a position corresponding to this position in a related sequence, is deleted or substituted with alanine or leucine; and/or

(11) an amino acid residue at position 43 in the amino acid sequence shown in SEQ ID NO:1 or at a position corresponding to this position in a related sequence, is deleted or substituted with leucine; and/or

(12) an amino acid residue at position 45 in the amino acid sequence shown in SEQ ID NO:1 or at a position corresponding to this position in a related sequence, is deleted or substituted with leucine, phenylalanine, methionine or valine, preferably leucine; and/or

(13) an amino acid residue at position 53 in the amino acid sequence shown in SEQ ID NO:1 or at a position corresponding to this position in a related sequence, is deleted or substituted with valine; and/or

(14) an amino acid residue at position 57 in the amino acid sequence shown in SEQ ID NO:1 or at a position corresponding to this position in a related sequence, is deleted or substituted with serine; and/or

(15) an amino acid residue at position 58 in the amino acid sequence shown in SEQ ID NO:1 or at a position corresponding to this position in a related sequence, is deleted or substituted with threonine; and/or

(16) an amino acid residue at position 66 in the amino acid sequence shown in SEQ ID NO:1 at a position corresponding to this position in a related sequence, is deleted or substituted with histidine; and/or

(17) an amino acid residue at position 75 in the amino acid sequence shown in SEQ ID NO:1 or at a position corresponding to this position in a related sequence, is deleted or substituted with isoleucine; and/or

(18) an amino acid residue at position 77 in the amino acid sequence shown in SEQ ID NO:1 or at a position corresponding to this position in a related sequence, is deleted or substituted with asparagine or arginine; and/or

(19) an amino acid residue at position 80 in the amino acid sequence shown in SEQ ID NO:1 or at a position corresponding to this position in a related sequence, is deleted or substituted with glycine; and/or

(20) an amino acid residue at position 86 in the amino acid sequence shown in SEQ ID NO:1 or at a position corresponding to this position in a related sequence, is deleted or substituted with glutamine; and/or

(21) an amino acid residue at position 87 in the amino acid sequence shown in SEQ ID NO:1 or at a position corresponding to this position in a related sequence, is deleted or substituted with glutamic acid; and/or

(22) an amino acid residue at position 91 in the amino acid sequence shown in SEQ ID NO:1 or at a position corresponding to this position in a related sequence, is deleted or substituted with histidine; and/or

(23) an amino acid residue at position 105 in the amino acid sequence shown in SEQ ID NO:1 or at a position corresponding to this position in a related sequence, is deleted or substituted with alanine; and/or

(24) an amino acid residue at position 111 in the amino acid sequence shown in SEQ ID NO:1 or at a position corresponding to this position in a related sequence, is deleted or substituted with methionine; and/or

(25) an amino acid residue at position 116 in the amino acid sequence shown in SEQ ID NO:1 or at a position corresponding to this position in a related sequence, is deleted or substituted with arginine, isoleucine, leucine, serine or methionine, preferably arginine or isoleucine; and/or

(26) an amino acid residue at position 118 in the amino acid sequence shown in SEQ ID NO:1 at a position corresponding to this position in a related sequence, is deleted or substituted with leucine or tryptophane; and/or

(27) an amino acid residue at position 120 in the amino acid sequence shown in SEQ ID NO:1 or at a position corresponding to this position in a related sequence, is deleted or substituted with asparagine, leucine, arginine, isoleucine or valine, preferably asparagine, leucine, arginine or isoleucine; and/or

(28) an amino acid residue at position 121 in the amino acid sequence shown in SEQ ID NO:1 or at a position corresponding to this position in a related sequence, is deleted or substituted with arginine, leucine, tryptophan, phenylalanine, tyrosine, asparagine or lysine, preferably arginine or phenylalanine; and/or

(29) the amino acid residue at position 122 in the amino acid sequence shown in SEQ ID NO:1 or at a position corresponding to this position in a related sequence, is substituted with methionine or tyrosine; and/or

(30) an amino acid residue at position 123 in the amino acid sequence shown in SEQ ID NO:1 or at a position corresponding to this position in a related sequence, is deleted or substituted with methionine or arginine; and/or

(30) an amino acid residue at position 129 in the amino acid sequence shown in SEQ ID NO:1 or at a position corresponding to this position in a related sequence, is deleted or substituted with proline or valine; and/or

(32) an amino acid residue at position 134 in the amino acid sequence shown in SEQ ID NO:1 or at a position corresponding to this position in a related sequence, is deleted or substituted with glycine; and/or

(33) an amino acid residue at position 139 in the amino acid sequence shown in SEQ ID NO:1 or at a position corresponding to this position in a related sequence, is deleted or substituted with cysteine or alanine; and/or

(34) an amino acid residue at position 141 in the amino acid sequence shown in SEQ ID NO:1 or at a position corresponding to this position in a related sequence, is deleted or substituted with proline, cysteine; glycine or threonine; and/or

(35) an amino acid residue at position 142 in the amino acid sequence shown in SEQ ID NO:1 or at a position corresponding to this position in a related sequence, is deleted or substituted with alanine; and/or

(36) an amino acid residue at position 159 in the amino acid sequence shown in SEQ ID NO:1 or at a position corresponding to this position in a related sequence, is deleted or substituted with leucine; and/or

(37) an amino acid residue at position 160 in the amino acid sequence shown in SEQ ID NO:1 or at a position corresponding to this position in a related sequence, is deleted or substituted with valine; and/or

(38) an amino acid residue at position 161 in the amino acid sequence shown in SEQ ID NO:1 or at a position corresponding to this position in a related sequence; is deleted or substituted with arginine; and/or

(39) an amino acid residue at position 164 in the amino acid sequence shown in SEQ ID NO:1 or at a position corresponding to this position in a related sequence, is deleted or substituted with glutamine; and/or

(40) an amino acid residue at position 166 in the amino acid sequence shown in SEQ ID NO:1 or at a position corresponding to this position in a related sequence, is deleted or substituted with serine; and/or

(41) an amino acid residue at position 173 in the amino acid sequence shown in SEQ ID NO:1 or at a position corresponding to this position in a related sequence, is deleted or substituted with cysteine; and/or
(42) an amino acid residue at position 177 in the amino acid sequence shown in SEQ ID NO:1 or at a position corresponding to this position in a related sequence, is deleted or substituted with valine or cysteine, preferably valine; and/or
(43) an amino acid residue at position 179 in the amino acid sequence shown in SEQ ID NO:1 or at a position corresponding to this position in a related sequence, is deleted or substituted with lysine or leucine; and/or
(44) an amino acid residue at position 180 in the amino acid sequence shown in SEQ ID NO:1 or at a position corresponding to this position in a related sequence, is deleted or substituted with proline; and/or
(45) an amino acid residue at position 182 in the amino acid sequence shown in SEQ ID NO:1 or at a position corresponding to this position in a related sequence, is deleted or substituted with glutamic acid; and/or
(46) an amino acid residue at position 186 in the amino acid sequence shown in SEQ ID NO:1 or at a position corresponding to this position in a related sequence, is deleted or substituted with histidine, leucine, valine, isoleucine or asparagine; and/or
(47) an amino acid residue at position 188 in the amino acid sequence shown in SEQ ID NO:1 or at a position corresponding to this position in a related sequence, is deleted or substituted with cysteine; and/or
(48) an amino acid residue at position 198 in the amino acid sequence shown in SEQ ID NO:1 or at a position corresponding to this position in a related sequence, is deleted or substituted with aspartic acid; and/or
(49) an amino acid residue at position 204 in the amino acid sequence shown in SEQ ID NO:1 or at a position corresponding to this position in a related sequence, is deleted or substituted with leucine; and/or
(50) an amino acid residue at position 205 in the amino acid sequence shown in SEQ ID NO:1 or at a position corresponding to this position in a related sequence, is deleted or substituted with histidine; and/or
(51) an amino acid residue at position 208 in the amino acid sequence shown in SEQ ID NO:1 or at a position corresponding to this position in a related sequence, is deleted or substituted with leucine; and/or
(52) an amino acid residue at position 215 in the amino acid sequence shown in SEQ ID NO:1 or at a position corresponding to this position in a related sequence; is deleted or substituted with alanine; and/or an amino acid residue at position 221 in the amino acid sequence shown in SEQ ID NO:1 or at a position corresponding to this position in a related sequence, is deleted or substituted with glutamic acid; and/or
(54) an amino acid residue at position 227 in the amino acid sequence shown in SEQ ID NO:1 or at a position corresponding to this position in a related sequence, is deleted or substituted with lysine; and/or
(55) an amino acid residue at position 231 in the amino acid sequence shown in SEQ ID NO:1 or at a position corresponding to this position in a related sequence, is deleted or substituted with glutamine or leucine; and/or
(56) an amino acid residue at position 238 in the amino acid sequence shown in SEQ ID NO:1 or at a position corresponding to this position in a related sequence, is deleted or substituted with arginine, glutamic acid or lysine; and/or
(57) an amino acid residue at position 241 in the amino acid sequence shown in SEQ ID NO:1 or at a position corresponding to this position in a related sequence, is deleted or substituted with methionine or isoleucine; and/or
(58) an amino acid residue at position 242 in the amino acid sequence shown in SEQ ID NO:1 or at a position corresponding to this position in a related sequence, is deleted or substituted with alanine or glutamic acid; and/or
(59) an amino acid residue at position 246 in the amino acid sequence shown in SEQ ID NO:1 or at a position corresponding to this position in a related sequence, is deleted or substituted with glutamic acid; and/or
(60) an amino acid residue at position 248 in the amino acid sequence shown in SEQ ID NO:1 or at a position corresponding to this position in a related sequence; is deleted or substituted with threonine; and/or
(61) an amino acid residue at position 251 in the amino acid sequence shown in SEQ ID NO:1 or at a position corresponding to this position in a related sequence, is deleted or substituted with methionine, phenylalanine or valine, preferably methionine; and/or
(62) an amino acid residue at position 252 in the amino acid sequence shown in SEQ ID NO:1 or at a position corresponding to this position in a related sequence, is deleted or substituted with glutamic acid; and/or
(63) an amino acid residue at position 253 in the amino acid sequence shown in SEQ ID NO:1 or at a position corresponding to this position in a related sequence, is deleted or substituted with valine or isoleucine; and/or
(64) an amino acid residue at position 255 in the amino acid sequence shown in SEQ ID NO:1 or at a position corresponding to this position in a related sequence, is deleted or substituted with glutamic acid; and/or
(65) an amino acid residue at position 258 in the amino acid sequence shown in SEQ ID NO:1 or at a position corresponding to this position in a related sequence; is deleted or substituted with leucine; and/or
(66) an amino acid residue at position 264 in the amino acid sequence shown in SEQ ID NO:1 or at a position corresponding to this position in a related sequence, is deleted or substituted with glutamine; and/or
(67) an amino acid residue at position 267 in the amino acid sequence shown in SEQ ID NO:1 or at a position corresponding to this position in a related sequence, is deleted or substituted with arginine; and/or
(68) an amino acid residue at position 279 in the amino acid sequence shown in SEQ ID NO:1 or at a position corresponding to this position in a related sequence, is deleted or substituted with alanine; and/or
(69) an amino acid residue at position 282 in the amino acid sequence shown in SEQ ID NO:1 or at a position corresponding to this position in a related sequence, is deleted or substituted with cysteine, serine, glutamic acid, glycine, glutamine; threonine, valine, alanine or aspartic acid; and/or
(70) an amino acid residue at position 291 in the amino acid sequence shown in SEQ ID NO:1 or at a position corresponding to this position in a related sequence, is deleted or substituted with aspartic acid; and/or
(71) an amino acid residue at position 293 in the amino acid sequence shown in SEQ ID NO:1 or at a position corresponding to this position in a related sequence, is deleted or substituted with phenylalanine or tryptophan; and/or

(72) an amino acid residue at position 297 in the amino acid sequence shown in SEQ ID NO:1 or at a position corresponding to this position in a related sequence; is deleted or substituted with cysteine or leucine, preferably cysteine; and/or

(73) an amino acid residue at position 299 in the amino acid sequence shown in SEQ ID NO:1 or at a position corresponding to this position in a related sequence, is deleted or substituted with proline or lysine; and/or

(74) an amino acid residue at position 303 in the amino acid sequence shown in SEQ ID NO:1 or at a position corresponding to this position in a related sequence; is deleted or substituted with methionine; and/or

(75) an amino acid residue at position 307 in the amino acid sequence shown in SEQ ID NO:1 or at a position corresponding to this position in a related sequence, is deleted or substituted with histidine; and/or

(76) an amino acid residue at position 308 in the amino acid sequence shown in SEQ ID NO:1 or at a position corresponding to this position in a related sequence; is deleted or substituted with serine; and/or

(77) an amino acid residue at position 315 in the amino acid sequence shown in SEQ ID NO:1 or at a position corresponding to this position in a related sequence, is deleted or substituted with serine.

The invention also relates to variants as defined in (1) to (77) hereinabove, wherein the amino acid residue indicated as substituting the amino acid residue at the position in SEQ ID NO: 1 is not that particular amino acid residue but an amino acid residue which is conservative in relation to the indicated substituting amino acid. Whether an amino acid is conservative with respect to another amino acid can be judged according to means and methods known in the art. One possibility is the PAM 250 matrix; alternatively, the Blosum Family Matrices can be used.

In one embodiment the present invention relates to a variant of a MDP decarboxylase having an amino acid sequence as shown in SEQ ID NO:1 or an amino acid sequence having at least 40%, 50%, 60% or 90% sequence identity to SEQ ID NO:1, wherein the amino acid residue at position 282 in the amino acid sequence shown in SEQ ID NO:1 or at a position corresponding to this position in a related sequence is substituted with another amino acid residue or is deleted. In a preferred embodiment the present invention relates to such a variant in which at least one further amino acid residue is substituted or deleted at a position selected from the group consisting of positions 9, 11, 16, 24, 28, 42, 43, 45, 53, 66, 77, 80, 91, 105, 116, 118, 120, 121, 122, 123, 129, 134, 141, 159, 160, 161, 173; 177, 180, 186, 215, 238, 241, 242, 248, 251, 253; 258, 264, 279; 291, 293, 297; 299, 303, 307, 308, 1, 2, 23, 31, 57, 58, 75, 86, 87, 111, 139, 142, 164, 166, 179, 182, 188, 198, 204, 205, 208, 221, 227, 231, 246, 252; 255; 267, and 315, preferably selected from the group consisting of positions 9, 11, 16, 24, 28, 42; 45, 53, 80, 91, 105, 116, 118, 120, 121, 122, 123; 129, 141, 159, 161, 173, 177, 180, 215, 238; 241, 242, 248, 251, 253, 264, 279, 291, 293, 297, 299; 303, 307, 308 and 315, even more preferably selected from the group consisting of positions 9, 11, 42, 45, 116, 118, 120, 121, 122, 123, 129, 177, 251, 253, 264, 293, 297 and 303.

In one particular embodiment, the amino acid residues at position 282 in the amino acid sequence shown in SEQ ID NO:1 or at a position corresponding to this position in a related sequence is substituted with cysteine, serine, glutamic acid, glycine, glutamine, threonine, valine, alanine or aspartic acid, preferably with cysteine. In another particular embodiment, the substitutions at any one of positions 9, 11, 16, 24, 28, 42, 43, 45, 53, 66, 77, 80, 91, 105, 116, 118, 120, 121, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315 are as indicated herein-above.

In one embodiment the present invention relates to a variant of a MDP decarboxylase having an amino acid sequence as shown in SEQ ID NO:1 or an amino acid sequence having at least 40%, 50%, 60% or 90% sequence identity to SEQ ID NO:1, wherein the amino acid residues at position 121 in the amino acid sequence shown in SEQ ID NO:1 or at a position corresponding to this position in a related sequence is deleted or substituted with another amino acid residue, preferably arginine, leucine, lysine or phenylalanine. In a preferred embodiment the present invention relates to such a variant in which at least one further amino acid residue is deleted or substituted at a position selected from the group consisting of positions 9, 11, 16, 24, 28, 42, 43, 45, 53, 66, 77, 80, 91, 105, 116, 118, 120, 122, 123, 129, 134, 141, 159, 160, 161, 173, 177, 180, 186, 215, 238, 241, 242, 248, 251, 253, 258, 264, 279, 282, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315, preferably selected from the group consisting of positions 11, 16, 24, 28, 45, 53, 80, 91, 105, 116, 118, 120, 123, 141, 159, 161, 173, 177, 180, 215, 238, 241, 242, 248, 258, 279, 282, 291, 297, 299, 303, 307, 308 and 315. The substitutions at any of these positions are preferably those as listed herein-above.

The present invention also relates to a variant of a MDP decarboxylase having an amino acid sequence as shown in SEQ ID NO:1 or an amino acid sequence having at least 40%, 50%, 60% or 90% sequence identity to SEQ ID NO:1, wherein the amino acid residues at position 282 in the amino acid sequence shown in SEQ ID NO:1 or at a position corresponding to this position in a related sequence is deleted or substituted with another amino acid residue, wherein the amino acid residue at position 121 in the amino acid sequence shown in SEQ ID NO:1 or at a position corresponding to this position in a related sequence is deleted or substituted with another amino acid residue and wherein at least one further amino acid residue is substituted at a position selected from the group consisting of positions 9, 11; 16; 24; 28, 42, 43, 45, 53, 66, 77, 80, 91, 105, 116, 118, 120, 122, 123, 129, 134, 141, 159, 160, 161, 173, 177, 180, 186, 215, 238, 241; 242, 248, 251, 253, 258, 264, 279, 291, 293, 297, 299; 303, 307, 308, 1, 2, 23; 31, 57, 58, 75, 86, 87, 111, 139; 142, 164, 166, 179, 182, 188, 198, 204, 205, 208, 221, 227, 231, 246, 252, 255, 267, and 315, preferably selected from the group consisting of positions 11, 16, 24, 28, 45, 53, 80, 91, 105, 116, 118, 120, 123, 141, 159, 161, 173, 177, 180, 215, 238, 241, 242, 248, 258, 279, 291, 297, 299, 303, 307, 308 and 315.

In another particular embodiment, the amino acid residue at position 121 in the amino acid sequence shown in SEQ ID NO:1 or at a position corresponding to this position in a related sequence is substituted with arginine; leucine; lysine and phenylalanine. In a further preferred embodiment, the substitutions at any one of the positions 9, 11, 16, 24, 28, 42, 43, 45, 53, 66, 77, 80, 91, 105; 116, 118, 120, 122, 123, 129, 134; 141, 159, 160, 161, 173; 177; 180, 186, 215, 238, 241; 242, 248, 251, 253, 258, 264, 279, 291, 293, 297, 299, 303, 307, 308, 1, 2, 23, 31, 57, 58, 75, 86, 87, 111, 139, 142; 164; 166, 179, 182, 188, 198, 204, 205; 208, 221, 227, 231, 246, 252, 255, 267, and 315 are those as indicated herein-above.

In a preferred embodiment the variant according to the invention is characterized in that it contains at least three deletions and/or substitutions, wherein one deletion/substitution is at position 282 in the amino acid sequence shown in SEQ ID NO:1 or at a position corresponding to this position in a related sequence, another deletion/substitution is at position 121 in the amino acid sequence shown in SEQ ID NO:1 or at a position corresponding to this position in a related sequence and at least one further deletion/substitution is at a position selected from the group consisting of positions 11, 45, 116, 120 or 177 of SEQ ID NO: 1 or a position corresponding to any of these positions.

It is preferred that the following positions in SEQ ID NO:1 or the positions corresponding to any of these positions in a related sequence in a related sequence as defined above are at least modified by deletion or substitution:

45, 121 and 282; or
11, 121 and 282; or
116, 121 and 282; or
121, 177 and 282; or
120, 121 and 282; or
173, 282 and 297.

The substitutions at the indicated positions are preferably those as indicated herein-above.

Particularly preferred variants with three mutations show the following substitutions in SEQ ID NO:1:

E45L-Y121R-K282C
K282C-Y121R-Y11E
K116I-Y121R-K282C
Y121R-E177V-K282C
A120R-Y121L-K282C
M173C-K282C-F297L or the corresponding substitutions at the corresponding positions in a structurally related sequence as defined above.

The present invention also relates to a variant of a MOP decarboxylase having an amino acid sequence as shown in SEQ ID NO:1 or an amino acid sequence having at least 40%, 50%, 60% or 90% sequence identity to SEQ ID NO:1, wherein the amino acid residues at position 282 in the amino acid sequence shown in SEQ ID NO:1 or at a position corresponding to this position in a related sequence is substituted with another amino acid residue, wherein the amino acid residues at position 297 in the amino acid sequence shown in SEQ ID NO:1 or at a position corresponding to this position in a related sequence is substituted with another amino acid residue and wherein the amino acid residues at position 173 in the amino acid sequence shown in SEQ ID NO:1 or at a position corresponding to this position in a related sequence is substituted with another amino acid residue. In a particular embodiment, the amino acid residues at position 282 in the amino acid sequence shown in SEQ ID NO:1 or at a position corresponding to this position in a related sequence is substituted with cysteine, serine, glutamic acid, glycine, glutamine, threonine, valine, alanine or aspartic acid, preferably with cysteine. In another particular embodiment, the amino acid residue at position 297 in the amino acid sequence shown in SEQ ID NO:1 or at a position corresponding to this position in a related sequence is substituted with leucine. In a further embodiment the amino acid residues at position 173 in the amino acid sequence shown in SEQ ID NO:1 or at a position corresponding in a related sequence to this position is substituted with cysteine.

In another embodiment the variant according to the invention is characterized in that it contains at least four deletions and/or substitutions at positions selected from the group consisting of positions 9, 11, 16, 24, 28, 42, 43, 45, 53, 66, 77, 80, 91, 105, 116, 118, 120, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315, preferably selected from the group consisting of positions 9, 11, 16, 24, 28, 45, 53, 80, 91, 105, 118, 121, 123, 141, 159, 161, 173, 177, 180, 215, 238, 241, 242, 248, 258, 279, 282, 291, 297, 299, 303, 307, 308 and 315 in the amino acid sequence shown in SEQ ID NO:1 or at a position corresponding to any of these positions in a related sequence as defined above. Preferably, one of the deletions/substitutions is at position 303 of SEQ ID NO:1 or at a position corresponding to this position in a related sequence as defined above. More preferably, this position is replaced by a methionine. In another embodiment the substitutions at the remaining three positions are effected at positions selected from the group consisting of positions 45, 121, 173, 282, 307 and 308 or at a position corresponding to any of these positions in a related sequence as defined above.

It is preferred that the following positions in SEQ ID NO:1 or the positions corresponding to any of these positions in a related sequence as defined above are at least modified by deletion or substitution:

121, 282, 303 and 308; or
173, 303, 307 and 308; or
45, 173, 282 and 303.

Preferably, the substitution at position 45 is valine, the substitution at position 121 is an arginine, the substitution at position 173 or 282 is a cysteine, the substitution at position 307 is a histidine and the substitution at position 308 is a serine. Most preferred are the following combinations of substitutions: Y121R-K282C-L303M-T308S; M173C-L303M-K307H-T308S; E45V-M173C-K282C-L303M or the corresponding substitutions at the corresponding positions in a structurally related sequence as defined above.

In another embodiment the variant according to the invention is characterized in that it contains at least five deletions and/or substitutions at positions selected from the group consisting of positions 9, 11, 16, 24, 28, 42, 43, 45, 53, 66, 77, 80, 91, 105, 116, 118, 120, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315, preferably selected from the group consisting of positions 9, 11, 16, 24, 28, 45, 53, 80, 91, 105, 118, 121, 123, 141, 159, 161, 173, 177, 180, 215, 238, 241, 242, 248, 258, 279, 282, 291, 297, 299, 303, 307, 308 and 315 in the amino acid sequence shown in SEQ ID NO:1 or at a position corresponding to any of these positions in a related sequence as defined above. Preferably, one of these substitutions is at position 303 of SEQ ID NO:1 or at a position corresponding to this position in a related sequence as defined above. More preferably, this position is replaced by a methionine. In another embodiment the deletions/substitutions at the remaining three positions are effected at positions selected from the group consisting of positions 9, 11, 118, 121, 159, 173, 282, 307 and 308 or at a position corresponding to any of these positions in a related sequence as defined above.

It is preferred that the following positions in SEQ ID NO:1 or the positions corresponding to any of these positions in a related sequence as defined above are at least modified by deletion or substitution:

121, 173, 282, 303 and 308; or
159, 173, 303, 307 and 308; or
9, 11, 303, 307 and 308; or
118, 121, 173, 282 and 303.

Preferably the substitution at position 9 is leucine, the substitution at position 11 is phenylalanine, the substitution at position 118 is leucine, the substitution at position 121 is an arginine, the substitution at position 159 is leucine, the substitution at position 173 or 282 is a cysteine, the substitution at position 307 is a histidine and the substitution at position 308 is a serine.

Particularly preferred variants with five mutations show the following substitutions in SEQ ID NO:1:
Y121R-M173C-K282C-L303M-T308S
E159L-M173C-L303M-K307H-T308S
R9L-Y11F-L303M-K307H-T308S
C118L-Y121R-M173C-K282C-L303M
or the corresponding substitutions at the corresponding positions in a structurally related sequence as defined above.

In another embodiment the variant according to the invention is characterized in that it contains at least six deletions and/or substitutions at positions selected from the group consisting of positions 9, 11, 16, 24, 28, 42, 43, 45, 53, 66, 77, 80, 91, 105, 116, 118, 120, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315, preferably selected from the group consisting of positions 16, 24, 28, 45, 53, 80, 91, 105, 118, 121, 123, 141, 159, 161, 173, 177, 180, 215, 238, 241, 242, 248, 258, 279, 282, 291, 297, 299, 303, 307, 308 and 315 in the amino acid sequence shown in SEQ ID NO:1 or at a position corresponding to any of these positions in a related sequence as defined above. Preferably, one of these deletions/substitutions is at position 282 of SEQ ID NO:1 or at a position corresponding to this position in a related sequence as defined above. More preferably, this position is replaced by a cysteine. In another embodiment, one of these deletions/substitutions is at position 173 of SEQ ID NO:1 or at a position corresponding to this position in a related sequence as defined above. More preferably, this position is replaced by a cysteine. In another embodiment the deletions/substitutions at the remaining four positions are effected at positions selected from the group consisting of positions 45, 121, 159, 215, 297, 303 and 308 or at a position corresponding to any of these positions in a related sequence as defined above.

It is preferred that the following positions in SEQ ID NO:1 or the positions corresponding to any of these positions in a related sequence as defined above are at least modified by deletion or substitution:
121, 159, 173, 282, 303 and 308; or
121, 159, 173, 215, 282 and 303; or
45, 159, 173, 282, 297 and 308.

Preferably, the substitution at position 45 is leucine, the substitution at position 121 is an arginine, the substitution at position 159 is leucine, the substitution at position 215 is alanine, the substitution at position 297 is leucine, the substitution at position 303 is a methionine and the substitution at position 308 is a serine. Most preferred are the following combinations of substitutions:

Particularly preferred variants with six mutations show the following substitutions in SEQ ID NO:1:
Y121R-E159L-M173C-K282C-L303M-T308S
Y121R-E159L-M173C-V215A-K282C-L303M
E45L-E159L-M173C-K282C-F297L-T308S
or the corresponding substitutions at the corresponding positions in a structurally related sequence as defined above.

In another embodiment the variant according to the invention is characterized in that it contains at least seven substitutions at positions selected from the group consisting of positions 9, 11, 16, 24, 28, 42, 43, 45, 53, 66, 77, 80, 91, 105, 116, 118, 120, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315, preferably selected from the group consisting of positions 16, 24, 28, 45, 53, 80, 91, 105, 118, 121, 123, 141, 159, 161, 173, 177, 180, 215, 238, 241, 242, 248, 258, 279, 282, 291, 297, 299, 303, 307, 308 and 315 in the amino acid sequence shown in SEQ ID NO:1 or at a position corresponding to any of these positions in a related sequence as defined above. Preferably, one of these deletions/substitutions is at position 282 of SEQ ID NO:1 or at a position corresponding to this position in a related sequence as defined above. More preferably, this position is replaced by a cysteine. In another embodiment, one of these deletions/substitutions is at position 173 of SEQ ID NO:1 or at a position corresponding to this position in a related sequence as defined above. More preferably, this position is replaced by a cysteine. In another embodiment, one of these deletions/substitutions is at position 121 of SEQ ID NO:1 or at a position corresponding to this position in a related sequence as defined above. More preferably, this position is replaced by an arginine. In another embodiment, one of these deletions/substitutions is at position 303 of SEQ ID NO:1 or at a position corresponding to this position in a related sequence as defined above. More preferably, this position is replaced by a methionine. In another embodiment the deletions/substitutions at the remaining three positions are effected at positions selected from the group consisting of positions 45, 118, 159, 177, 242, 297, 307, 308 and 315 or at a position corresponding to any of these positions in a related sequence as defined above.

It is preferred that the following positions in SEQ ID NO:1 or the positions corresponding to any of these positions in a related sequence as defined above are at least modified by deletion or substitution:
121, 159, 173, 282, 303, 307 and 308; or
45, 121, 159, 173, 282, 303 and 308; or
121, 159, 173, 282, 297, 303 and 308; or
118, 121, 159, 173, 282, 303 and 308; or
121, 159, 173, 177, 282, 303 and 308; or
121, 159, 173, 242, 282, 303 and 308; or
118, 121, 159, 173, 282, 303 and 315; or
118, 121, 159, 173, 177, 282 and 303;
45, 121, 173, 282, 297, 303 and 308; or
45, 118, 121, 173, 282, 303 and 308; or
45, 121, 159, 173, 282, 297 and 303, Preferably, the substitution at position 45 is valine, the substitution at position 118 is leucine or tryptophan, the substitution at position 159 is leucine, the substitution at position 177 is cysteine, the substitution at position 242 is alanine, the substitution at position 297 is leucine, the substitution at position 307 is a histidine and the substitution at position 308 or 315 is a serine. Most preferred are the following combinations of substitutions:

Particularly preferred variants with seven mutations show the following substitutions in SEQ ID NO:1:
Y121R-E159L-M173C-K282C-L303M-K307H-T308S
E45V-Y121R-E159L-M173C-K282C-L303M-T308S
Y121R-E159L-M 173C-K282C-F297L-L303M-T308S
C118L-Y121R-E159L-M173C-K282C-L303M-T308S Y121R-E159L-M173C-E177C-K282C-L303M-T308S
Y121R-E159L-M173C-T242A-K282C-L303M-T308S
C118L-Y121R-E159L-M173C-K282C-L303M-G315S
C118W-Y121R-E159L-M173C-E177C-K282C-L303M
C118L-Y121R-E159L-M173C-E177C-K282C-L303M
E45V-Y121R-M173C-K282C-F297L-L303M-T308S
E45V-C118L-Y121R-M173C-K282C-L303M-T308S
E45V-Y121R-E159L-M173C-K282C-F297L-L303M or the corresponding substitutions at the corresponding positions in a structurally related sequence as defined above.

In another embodiment the variant according to the invention is characterized in that it contains at least eight or at least nine deletions and/or substitutions at positions selected from the group consisting of positions 9, 11, 16, 24, 28, 42, 43, 45, 53, 66, 77, 80, 91, 105, 116, 118, 120, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315, preferably selected from the group consisting of positions 16, 24, 28, 45, 53, 80, 91, 105, 118, 121, 123, 141, 159, 161, 173, 177, 180, 215, 238, 241, 248, 258, 279, 282, 291, 297, 299, 303, 308 and 315 in the amino acid sequence shown in SEQ ID NO:1 or at a position corresponding to any of these positions in a related sequence as defined above. Preferably, one of these deletions/substitutions is at position 282 of SEQ ID NO:1 or at a position corresponding to this position in a related sequence as defined above. More preferably, this position is replaced by a cysteine. In another embodiment, one of these deletions/substitutions is at position 173 of SEQ ID NO:1 or at a position corresponding to this position in a related sequence as defined above. More preferably, this position is replaced by a cysteine. In another embodiment, one of these deletions/substitutions is at position 121 of SEQ ID NO:1 or at a position corresponding to this position in a related sequence as defined above. More preferably, this position is replaced by an arginine. In another embodiment, one of these deletions/substitutions is at position 303 of SEQ ID NO:1 or at a position corresponding to this position in a related sequence as defined above. More preferably, this position is replaced by a methionine. In another embodiment the deletions/substitutions at the remaining four and five positions, respectively, are effected at positions selected from the group consisting of positions 24, 45, 80, 118, 123, 159, 177, 215, 258, 297, 308 and 315 or at a position corresponding to any of these positions in a related sequence as defined above.

It is preferred that the following positions in SEQ ID NO:1 or the positions corresponding to any of these positions in a related sequence as defined above are at least modified by deletion or substitution:

80, 121, 159, 173, 282, 303, 308 and 315; or
24, 121, 159, 123, 173, 258, 282 and 303; or
118, 121, 159, 173, 177, 215, 282 and 303; or
24, 118; 121; 159; 173, 177, 282 and 303; or
45, 80, 121, 173, 282, 297, 303 and 308; or
45, 121, 159, 173, 177, 282, 303 and 308; or
118, 121, 159, 173, 177; 282; 297; 303 and 308; or
118, 121, 159, 173, 177, 215, 282, 297 and 303; or
80, 118; 121, 159, 173, 177, 282, 303 and 315; or
24, 45, 121, 123, 173; 282; 297; 303 and 308; or
45, 121, 159, 173, 177, 215, 258, 282 and 303.

Preferably, the substitution at position 24 is arginine, the substitution at position 45 is valine or leucine, the substitution at position 80 is glycine, the substitution at position 118 is leucine or tryptophan, the substitution at position 123 is arginine, the substitution at position 159 is leucine, the substitution at position 177 is cysteine, the substitution at position 215 is alanine, the substitution at position 258 is leucine, the substitution at position 297 is leucine and the substitution at position 308 or 315 is a serine.

Particularly preferred variants with eight or nine mutations show the following substitutions in SEQ ID NO:1:

D80G-Y121R-E159L-M173C-K282C-L303M-T308S-G315S
K24R-121R-E159L-K123R-M173C-M258L-K282C-L303M
C118L-Y121R-E159L-M173C-E177C-V215A-K282C-L303M
K24R-C118L-Y121R-E159L-M173C-E177C-K282C-L303M
E45V-D80G-Y121R-M173C-K282C-F297L-L303M-T308S
E45L-Y121R-E159L-M173C-E177C-K282C-L303M-T308S
C118L-Y121R-E159L-M173C-E177C-K282C-F297L-L303M-T308S
C118L-Y121R-E159L-M173C-E177C-V215A-K282C-F297L-L303M
D80G-C118L-Y121R-E159L-M173C-E177C-K282C-L303M-G315S
K24R-E45V-Y121R-K123R-M173C-K282C-F297L-L303M-T308S
E45V-Y121R-E159L-M173C-E177C-V215A-M258L-K282C-L303M or the corresponding substitutions at the corresponding positions in a structurally related sequence as defined above.

In another embodiment the variant according to the invention is characterized in that it contains at least ten substitutions at positions selected from the group consisting of positions 9, 11, 16, 24, 28, 42, 43, 45, 53, 66, 77, 80, 91, 105, 116, 118, 120, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315, preferably selected from the group consisting of positions 16, 24, 28, 45, 53, 91, 105, 118, 121, 141, 159, 161, 173, 177, 180, 215, 238, 241, 248, 279, 282, 291, 297, 299, 303 and 308 in the amino acid sequence shown in SEQ ID NO:1 or at a position corresponding to any of these positions in a related sequence as defined above. In one embodiment the deleted/substituted positions are positions 45, 118, 121, 159, 173, 215, 282, 297, 303 and 308. Preferably, the substitution at position 45 is valine, the substitution at position 118, 159 and 297 is leucine, the substitution at position 121 is arginine, the substitution at position 173 or 282 is cysteine, the substitution at position 215 is alanine, the substitution at position 303 is methionine and the substitution at position 308 is a serine. Thus, a particularly preferred variant with ten mutations shows the following substitutions in SEQ ID NO:1:

E45V-C118L-Y121R-E159L-M173C-V215A-K282C-F297L-L303M-T308S or the corresponding substitutions at the corresponding positions in a structurally related sequence as defined above.

In another embodiment the variant according to the invention is characterized in that it contains at least eleven deletions and/or substitutions at positions selected from the group consisting of positions 9, 11, 16, 24, 28, 42, 43, 45, 53, 66, 77, 80, 91, 105, 116, 118, 120, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315, preferably selected from the group consisting of positions 16, 24, 28, 53, 91, 105, 118, 121, 141, 159, 161, 173, 177, 180, 238, 241, 248, 279, 282, 291, 297, 299, 303 and 308 in the amino acid sequence shown in SEQ ID NO:1 or at a position corresponding to any of these positions in a related sequence as defined above. In one embodiment the deleted/substituted positions are positions 24, 118, 121, 159, 173, 177, 282, 291, 297, 303 and 308. Preferably, the substitution at position 24 or 121 is arginine, the substitution at position 118, 159 and 297 is leucine, the substitution at position 173, 177 or 282 is cysteine or valine, the substitution at position 291 is aspartate, the substitution at position 303 is methionine and the substitution at position 308 is a serine. Thus, a particularly preferred variant with eleven mutations shows the following substitutions in SEQ ID NO:1:

K24R-C118L-Y121R-E159L-M173C-E177C-K282C-E291D-F297L-L303M-T308S or the corresponding substitutions at the corresponding positions in a structurally related sequence as defined above.

A mutant containing these 11 substitutions is also referred to as "F9" in the context of the appended Example section.

In a preferred embodiment, the variant to the invention is characterized in that it contains at least ten, preferably at least eleven deletions and/or substitutions at positions selected from the group consisting of position 24, 118, 121, 159, 173, 177, 282, 291, 297, 303 and 308 in SEQ ID NO:1 or the positions corresponding to any of these positions in a related sequence as defined above, preferably substitutions as in the variant F9, and that it contains in addition at least one further deletion/substitution at a position selected from the group consisting of positions 16, 28, 53, 91, 105, 141, 161, 180, 238, 241, 248, 279, 1, 2, 23, 31, 57, 58, 75, 86, 87, 111, 139, 142, 164, 166, 179, 182, 188, 198, 204, 205, 208, 221, 227, 231, 246, 252, 255, 267, and 299 in SEQ ID NO:1 or the positions corresponding to any of these positions in a related sequence as defined above. Preferably substitutions at any of these positions are as defined herein-above.

In one embodiment the at least one further deletion/substitution is at positions 16 and 105 or at positions 16 and 141 in SEQ ID NO:1 or the positions corresponding to any of these positions in a related sequence as defined above.

In another embodiment the at least one further deletion/substitution is at positions 16, 141 and 241 in SEQ ID NO:1 or the positions corresponding to any of these positions in a related sequence as defined above.

In another embodiment the at least one further deletion/substitution is at positions 16, 141, 241 and 248 in SEQ ID NO:1 or the positions corresponding to any of these positions in a related sequence as defined above.

In another embodiment the at least one further deletion/substitution is at positions 141, 241 and 248 in SEQ ID NO:1 or the positions corresponding to any of these positions in a related sequence as defined above.

In another embodiment the at least one further deletion/substitution is at positions 16, 91, 141, 241 and 248 in SEQ ID NO:1 or the positions corresponding to any of these positions in a related sequence as defined above.

In another embodiment the at least one further deletion/substitution is at positions 16, 91, 141, 241, 248 and 299 in SEQ ID NO:1 or the positions corresponding to any of these positions in a related sequence as defined above.

In another embodiment the at least one further deletion/substitution is at positions 16, 91, 141, 241, 248, 299 and 28 in SEQ ID NO:1 or the positions corresponding to any of these positions in a related sequence as defined above.

In another embodiment the at least one further deletion/substitution is at positions 16, 91, 141, 241, 248, 299 and 28 in SEQ ID NO:1 or the positions corresponding to any of these positions in a related sequence as defined above.

In another embodiment the at least one further deletion/substitution is at positions 16, 141, 241, 248 and 28 in SEQ ID NO:1 or the positions corresponding to any of these positions in a related sequence as defined above.

In another embodiment the at least one further deletion/substitution is at positions 16, 141, 241, 248, 28 and 180 in SEQ ID NO:1 or the positions corresponding to any of these positions in a related sequence as defined above.

In another embodiment the at least one further deletion/substitution is at positions 16, 141, 241, 248, 28, 53 and 180. in SEQ ID NO:1 or the positions corresponding to any of these positions in a related sequence as defined above In another embodiment the at least one further deletion/substitution is at positions 16, 141, 241, 248, 28, 180 and 238 in SEQ ID NO:1 or the positions corresponding to any of these positions in a related sequence as defined above.

In another embodiment the at least one further deletion/substitution is at positions 16, 141, 241, 248, 28, 180 and 279 in SEQ ID NO:1 or the positions corresponding to any of these positions in a related sequence as defined above.

In another embodiment the at least one further deletion/substitution is at positions 16, 141, 241, 248, 28, 180 and 161 in SEQ ID NO:1 or the positions corresponding to any of these positions in a related sequence as defined above.

Particularly preferred variants show at least ten, preferably at least eleven deletions and/or substitutions at positions selected from the group consisting of position 24, 118, 121, 159, 173, 177, 282, 291, 297, 303 and 308, preferably substitutions as in the variant F9, in SEQ ID NO:1 or the corresponding substitutions at the corresponding positions in a structurally related sequence as defined above, and show in addition the following substitution(s) in SEQ ID NO:1:

S141P
S141T
S105A
Q299K
I16L
S248T
K241M
I16L-S105A
S141P-K241M-S248T
I16L-R91H-S141P-K241M-S248T
I16L-S141P
I16L-R91H-S141P-K241M-S248T Q299K
I16L-S141P-K241M
I16L-S141P-K241M-S248T
I16L-R91H-S141P-K241M-S248T-Q299K-M28K
I16L-R91H-S141P-K241M-S248T-Q299K-M28A
I16L-R91H-S141P-K241M-S248T-Q299K-K180P
I16L-S141P-K241I-S248T
I16L-S141P-K241I-S248T-M28K
I16L-S141P-K241I-S248T-M28K-K180P
I16L-S141P-K241I-S248T-M28K-T53V-K180P
I16L-S141P-K241I-S248T-M28K-K180P-A238K
I16L-S141P-K241I-S248T-M28K-K180P-A238R
I16L-S141P-K241I-S248T-M28K-K180P-C282V
I16L-S141P-K241I-S248T-M28K-K180P-P279A
I16L-S141P-K241I-S248T-M28K-K180P-Y161R
D2H
M42L-D87E-S139C-R186L-K231Q
E164Q-R186V-D252E

D87E-S139C-R186L-K231Q
R186V-Q267R
S139C-R186I
L111M-F122Y-R186L
M75I-R186V
S139A-S141C
K179K-R186V
R186V
A57S-A58T-K77R-R186V
L111M-R186L
R186L
A31S-R186V
S139A-S141G
M75I-R186L-S308T
R186L-S308T
R186I
L111M-R186V-S308T
R186V-D221E
L111M-R186V
M1L-L111M-R186V-S308T
R186N
R24S-G86Q-R186I
I16L-S141P-K241I-K180P-E227K
I16L-S141P-K241I-K180P-D291E-M303L
S141P-K241I-S248T-K180P-R24K
I16L-S141P-K241I-S248T-L297F
I16L-S141P-K241I-S248T-M28K-K180P-L188C-L297F-A246E
I16L-S141P-K241I-S248T-M28K-K180P-L188C-L297F-T242E
I16L-S141P-K241I-S248T-M28K-K180P-L188C-L297F-Y255E
I16L-S141P-K241I-S248T-M28K-K180P-L188C-L297F-T198D
I16L-S141P-K241I-S248T-M28K-K180P-L188C-L297F-K23L
I16L-S141P-K241I-S248T-M28K-K180P-L188C-L297F-K179L
I16L-S141P-K241I-S248T-M28K-K180P-L188C-L297F-K231L
I16L-S141P-K241I-S248T-M28K-K180P-L188C-L297F-P182E
I16L-S141P-K241I-S248T-M28K-K180P-L188C-L297F-A238E
I16L-S141P-K241I-S248T-M28K-K180P-L188C-L297F-K208L
I16L-S141P-K241I-S248T-M28K-K180P-L188C-L297F-R204L
I16L-S141P-K241I-S248T-M28K-K180P-L188C-L297F-R24L
I16L-S141P-K241I-S248T-M28K-K180P-L188C-L297F
I16L-S141P-K241I-K180P-D291E
I16L-S141P-K241I-S248T-K180P-Q267R-R24K-L118C-L159E
I16L-S141P-K241I-S248T-M28K-K180P-L188C-L297F-S142A
I16L-S141P-K241I-S248T-M28K-K180P-L159E-D291E
I16L-S141P-K241I-S248T-K180P-G166S-R24K
I16L-S141P-K241I-S248T-K180P-R24K
I16L-S141P-K241I-S248T-M28K-K180P-L188C-L297F-Q205H or the corresponding substitution(s) at the corresponding positions in a structurally related sequence as defined above.

The present inventors also constructed a computer 3D model of the *S. mitis* enzyme represented by the amino acid sequence shown in SEQ ID NO: 1 (see FIG. 6) in order to locate the mutated residues in the three dimensional structure. The structure of the enzyme is characterized by a cone-shaped fold, where the N-terminal region is oriented orthogonally against the relatively plane C-terminal region comprising five alpha helices. The active site is a positively charged cleft formed between the N and C terminal domains with an ATP binding P-loop nearby. The 3D structure of the *S. mitis* enzyme is extremely similar to the 3D structure of the MDP decarboxylase of *S. pyogenes* (see FIG. 6), the amino acid sequence of which shows 69% sequence identity to the *S. mitis* enzyme (SEQ ID NO:1). The 3D structure is also very similar to that reported in Byres et al. (J. Mol. Biol. 371 (2007), 540-553) for the MDP decarboxylases of *S. brucei* and *S. aureus*. FIG. 7 shows the sequence of the MDP decarboxylase in which the secondary structure (β-sheets and α-helices) as well as some of the mutated residues are highlighted.

It has been demonstrated that the mutations identified in the present invention have a direct effect on the rate of production of isobutene from 3-phosphonoxyisovalerate by the enzyme; however it is possible that these mutations confer to the enzyme other properties that have not been fully identified yet. For example, several substitutions replace wild type residues with cysteine residues (Y11, M173 and K282). In the improved mutants residues 234, M1730 and K2820 are close enough in the 3D modeled structure to suggest that the creation of a disulphide bridge is possible. Such a bond could stabilize the overall structure of the enzyme. To support this, some preliminary data indicates that some mutants are more resistant to thermal denaturation than the wild type enzyme.

Similarly these mutations may have an effect on the stability to pH, optimal temperature and the oligomeric state of the proteins. Preliminary data collected on the effect of pH on isobutene production indicate that some mutant variants are more active at acidic pH compared to the wild type enzyme.

One group of the identified positions are located in the N-terminal domain of the protein, in particular positions 1, 2, 9, 11, 42, 43, 45, 57, 58, 75, 77, 80, 86, 87, 91, 116, 118, 120, 121, 122, 123, 129 and 134.

An analysis revealed that residues 77, 80, 116, 118, 120, 121, 122, 123, 129 and 134 are located on the alpha helices No. 1, 2 and 3 in the N-terminal domain and are situated most distally from the substrate binding pocket. Residues 9, 11, 42, 43, 45 and 91 are located in close proximity to these alpha helices and in particular, they are located in the beta sheet on beta strands 1 and 4 that are directly adjacent to each other (see FIG. 8). Thus, all these residues are located in the N-terminus, are located close to each other in the 3D structure and do not show any structural proximity to the active site of the enzyme. Thus, in one preferred embodiment, the present invention relates to a variant of a mevalonate diphosphate decarboxylase having an amino acid sequence as shown in SEQ ID NO:1 or an amino acid sequence having at least 40%, 50%, 60% or 90% sequence identity to SEQ ID NO:1, wherein one or more amino acid residues at a position selected from the group consisting of positions 9, 11, 42, 43, 45, 77, 80, 91, 116, 118, 120, 121, 122, 123, 129 and 134 in the amino acid sequence shown in SEQ ID NO:1 or at a position corresponding to any of these positions, are substituted with another amino acid residue and wherein said mevalonate diphosphate decarboxylase has improved activity in converting 3-phosphonoxyisovalerate into isobutene.

Another group of the identified positions, in particular positions 159, 160, 164, 166, 173, 177, 179, 198, 204, 205, 208, 221, 227, 231, 238, 241, 242, 246, 248, 251, 252, 253, 255, 258, 264, 267, 282, 291, 293, 297, 299, 303, 307 and 308, are located in the C-terminal domain and most of these positions are located in alpha helices and in beta strands, in particular in alpha helices 8 and 9 and in beta strands 9 to 12. It is assumed that mutations at positions 238, 241, 242, 248, 253, 258, 264, 291, 293, 297, 299, 303, 307 and 308 (i.e. in the alpha helix no° 9 and in beta-strand no° 12) might create a more stable conformation that stabilizes the whole structure. Thus, in one preferred embodiment, the present invention relates to a variant of a mevalonate diphosphate decarboxylase having an amino acid sequence as shown in SEQ ID NO:1 or an amino acid sequence having at least 40%, 50%, 60% or 90% sequence identity to SEQ ID NO:1, wherein one or more amino acid residues at a position selected from the group consisting of positions 159, 160, 173, 177, 238, 241, 242, 248, 251, 253, 258, 264, 282, 291, 293, 297, 299, 303, 307 and 308, more preferably selected from the group consisting of positions 238, 241, 242, 248, 253, 258, 264, 291, 293, 297, 299, 303, 307 and 308 in the amino acid sequence shown in SEQ ID NO:1 or at a position corresponding to any of these positions in a related sequence, are substituted with another amino acid residue and wherein said mevalonate diphosphate decarboxylase has improved activity in converting 3-phosphonoxyisovalerate into isobutene.

In one particular embodiment it is preferred that one or more amino acid residues at a position selected from the group consisting of positions 293, 297, 299, 303, 307 and 308 in the amino acid sequence shown in SEQ ID NO:1 or at a position corresponding to any of these positions in a related sequence, are substituted with another amino acid residue. These residues are located in the most C-terminal part of the enzyme (in alpha helix 9 and beta strand 12) and might create a more stable confirmation that stabilizes the whole structure.

A third group of identified positions is located in or close to the binding pocket of the enzyme. This group encompasses positions 16, 23, 24, 28, 31, 111, 139, 141, 142, 182, 186, 188, 279 and 282. The MDP binding pocket is delimited by regions 13-22 and 97-107 that form the ATP binding site and includes in particular the P-loop (P99-S107). Another side consists of the region 274-280 where the catalytic base D276 is located and the region 136-146 which includes R144 that drives the final decarboxylation step of the substrate. Position 5105 lies within the phosphate binding loop (consensus GHMP kinase P-Xaa-GLSASAA->PTAAGLSSSSS in S. mitis). Interestingly the mutation that improves the production of IBN is a substitution to Ala that is closer to the consensus P-binding loop sequence compared to the wild type S. mitis MDP P-loop sequence. S141 is closely located to the R144 residue and its hydroxyl group interacts with the natural enzyme substrate and is thus believed to be important to determine the enzyme specificity. Substitution of S141 with threonine which has a bulkier side chain could potentially facilitate the interaction of the enzyme with the smaller sized mono-phosphorylated substrate Ply. Substitution to proline would drastically alter the structure of the region and might better accommodate this non-natural substrate Ply. 116, K24R and M28 are neighboring K22 which interacts with the phosphate groups of the natural substrate; altering this residues could affect the structure of this loop and bring K22 closer to the substrate. The best performing mutants harbor the K24R which alters the length of the side chains while increasing the positively charged environment of the binding pocket and the mutation M28K which adds a positive charge. P279 and K282 are close to the catalytic base D276 and R186 is neighboring S185 which interacts with the MVAPP substrate.

Thus, in one preferred embodiment, the present invention relates to a variant of a mevalonate diphosphate decarboxylase having an amino acid sequence as shown in SEQ ID NO:1 or an amino acid sequence having at least 40%, 50%, 60% or 90% sequence identity to SEQ ID NO:1, wherein one or more amino acid residues at a position selected from the group consisting of positions 16, 24, 28, 141, 186, 279 and 282 in the amino acid sequence shown in SEQ ID NO:1 or at a position corresponding to any of these positions in a related sequence, are substituted with another amino acid residue and wherein said mevalonate diphosphate decarboxylase has improved activity in converting 3-phosphonoxyisovalerate into isobutene.

The present invention also relates to a method for providing a variant of a mevalonate diphosphate decarboxylase wherein said variant shows an improved activity of converting 3-phosphonoxyisovalerate into isobutene said method comprising the step of effecting one or more changes in the sequence of the mevalonate diphosphate decarboxylase wherein said change(s) is/are effected at one or more amino acid positions selected from the group consisting of the amino acid positions corresponding to positions 282, 9, 11, 16, 24, 28, 42, 43, 45, 53, 66, 77, 80, 91, 105, 116, 118, 120, 121, 122, 123, 129, 134, 141, 159, 160, 161, 173, 177, 180, 186, 215, 238, 241, 242, 248, 251, 253, 258, 264, 279, 291, 293, 297, 299, 303, 307, 308, 1, 2, 23, 31, 57, 58, 75, 86, 87, 111, 139, 142, 164, 166, 179, 182, 188, 198, 204, 205, 208, 221, 227, 231, 246, 252, 255, 267, and 315 in the amino acid sequence shown in SEQ ID NO:1. "Corresponding to" means corresponding to any of these positions in a related sequence.

As regards the preferred embodiments of a mevalonate diphosphate decarboxylase to be mutated according to such a method, the same applies as has been set forth hereinabove.

In one preferred embodiment the mevalonate diphosphate decarboxylase from which the variant is derived is a mevalonate diphosphate decarboxylase which shows the amino acid sequence as shown in SEQ ID NO:1 or an amino acid sequence having at least 40%, 50%, 60% or 90% sequence identity to SEQ ID NO:1 or any of the preferred degrees of sequence identity as specified herein above.

Moreover, as regards preferred embodiments of the degree of improvement in activity and the changes to be effected, the same applies as described herein above.

The MDP decarboxylase of the present invention can be fused to a homologous or heterologous polypeptide or protein, an enzyme, a substrate or a tag to form a fusion protein. Fusion proteins in accordance with the present invention will have the same improved activity as the MDP decarboxylases of the present invention. Polypeptides, enzymes, substrates or tags that can be added to another protein are known in the art. They may be useful for purifying or detecting the proteins of the invention. For instance, tags that can be used for detection and/or purification are e.g. FLAG-tag, His6-tag or a Strep-tag. Tags for improving solubility or stability of the enzyme are MBP or ATS. Alternatively, the protein of the invention can be fused to an enzyme e.g. luciferase, for the detection or localisation of said protein. Other fusion partners include, but are not limited to, bacterial β-galactosidase, trpE, Protein A, β-lactamase, alpha amylase, alcohol dehydrogenase or yeast alpha mating factor.

It is also conceivable that the polypeptide, enzyme, substrate or tag is removed from the protein of the invention after e.g. purification.

Fusion proteins can typically be made by either recombinant nucleic acid methods or by synthetic polypeptide methods known in art.

The present invention further relates to a nucleic acid molecule encoding the enzymes, more preferably the MDP decarboxylase variants of the present invention and to a vector comprising said nucleic acid molecules. Vectors that can be used in accordance with the present invention are known in the art. The vectors can further comprise expression control sequences operably linked to the nucleic acid molecules of the present invention contained in the vectors. These expression control sequences may be suited to ensure transcription and synthesis of a translatable RNA in bacteria or fungi. Expression control sequences can for instance be promoters. Promoters for use in connection with the nucleic acid molecules of the present invention may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

Preferably, the vector of the present invention is an expression vector. Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad, Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad, Sci, USA 80 (1983), 21-25). Termination signals for transcription are also described in the literature.

Preferably, the nucleic acid molecules according to the invention are non-naturally occurring nucleic acid molecules, i.e., they are molecules which do not occur in nature. Such non-naturally occurring molecules differ significantly from naturally occurring nucleic acid molecules due to a difference, e.g., in structure. For example, such a non-naturally occurring nucleic acid molecule may encode a non-naturally occurring enzyme as described herein-above. Also a vector according to the present invention is preferably a non-naturally occurring vector, e.g., due to the presence of a non-naturally occurring nucleic acid molecule or due to the combination of elements which do not occur in such a combination in nature.

In addition, the present invention relates to a host cell comprising the vector of the present invention.

In a preferred embodiment, the host cell according to the presenting invention is a microorganism, in particular a bacterium or a fungus. In a more preferred embodiment, the host cell of the present invention is E. coli, a bacterium of the genus Clostridium or a yeast cell, such as S. cerevisiae. In another preferred embodiment the host cell is a plant cell or a non-human animal cell.

The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc. Such a host cell according to the present invention is preferably a non-naturally occurring host cell, i.e., a host cell which does not occur in nature. Such a non-naturally occurring host cell differs from a naturally occurring cell due to a modification with a nucleic acid molecule or vector as described herein-above.

The present invention also relates to the use of the MDP decarboxylase of the present invention or a host cell comprising said MDP decarboxylase for the conversion of 3-hydroxyisovalerate or of 3-phosphonoxyisovalerate into isobutene, In addition, the present invention relates to a method for producing isobutene from 3-hydroxyisovalerate or from 3-phosphonoxyisovalerate comprising the steps of: Culturing the host cell of the present invention in a suitable medium and recovering said isobutene.

It has been described previously that the MDP decarboxylase is able to catalyze the conversion of mevalonate into isoprenol via the intermediate mevalonate-3-phosphate (see WO 2011/076261). The inventors could show that also the MDP decarboxylase variants according to the present invention are able to catalyze this conversion and in particular the conversion of mevalonate-3-phosphate into isoprenol. Therefore, the present invention also relates to the use of an MDP decarboxylase variant according to the present invention and as described herein above or of a microorganism expressing such a variant for the conversion of mevalonate or mevalonate-3-phosphate into isoprenol.

In addition, the present invention relates to a method for producing isoprenol from mevalonate or from mevalonate-3-phosphate comprising the steps of: Culturing the host cell of the present invention in a suitable medium and recovering said isoprenol.

It has also been described that the MDP decarboxylase is able to catalyze the conversion of 3-hydroxypent-4-enoate into 1,3-butadiene (see PCT/EP2012/075921) via the intermediate 3-phosphonoxypent-4-enoate. The inventors could show that also the MDP decarboxylase variants according to the present invention are able to catalyze this conversion, in particular the conversion of 3-phosphonoxypent-4-enoate into 1,3-butadiene. Therefore, the present invention also relates to the use of an MDP decarboxylase variant according to the present invention and as described herein above or of a microorganism expressing such a variant for the conversion of 3-hydroxypent-4-enoate or of 3-phosphonoxypent-4-enoate into 1,3-butadiene.

In addition, the present invention relates to a method for producing 1,3-butadiene from 3-hydroxypent-4-enoate or from 3-phosphonoxypent-4-enoate comprising the steps of: Culturing the host cell of the present invention in a suitable medium and recovering said 1,3-butadiene.

In the above described methods, the microorganisms are cultivated under suitable culture conditions allowing the occurrence of the enzymatic reaction of the MDP decarboxylases of the present invention. The specific culture conditions depend on the specific microorganism employed but are well known to the person skilled in the art. The culture conditions are generally chosen in such a manner that they allow the expression of the genes encoding the MDP decarboxylases of the present invention. Various methods are known to the person skilled in the art in order to improve and fine-tune the expression of certain genes at certain stages of the culture such as induction of gene expression by chemical inducers or by a temperature shift.

In another embodiment, the above described methods of the invention comprise the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical process like the method of the present invention is carried out which involves organisms, preferably microorganisms and/or biochemically active substances, i.e., the enzyme(s) described above derived from such organisms or organisms harboring the above described enzyme(s). In a bioreactor or a fermenter, this process can either be aerobic or anaerobic. These bioreactors are commonly cylindrical, and may range in size from litres to hundreds of cubic meters, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

The method according to the invention furthermore comprises the step of collecting gaseous products, i.e. isobutene, degassing out of the reaction, i.e. recovering the products which degas, e.g., out of the culture. Thus in a preferred embodiment, the method is carried out in the presence of a system for collecting isobutene under gaseous form during the reaction.

As a matter of fact, short alkenes such as isobutene adopt the gaseous state at room temperature and atmospheric pressure. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

The present invention is further described by reference to the following non-limiting figures and examples.

FIG. 1: General diagram of the directed evolution approach

Figure 2:
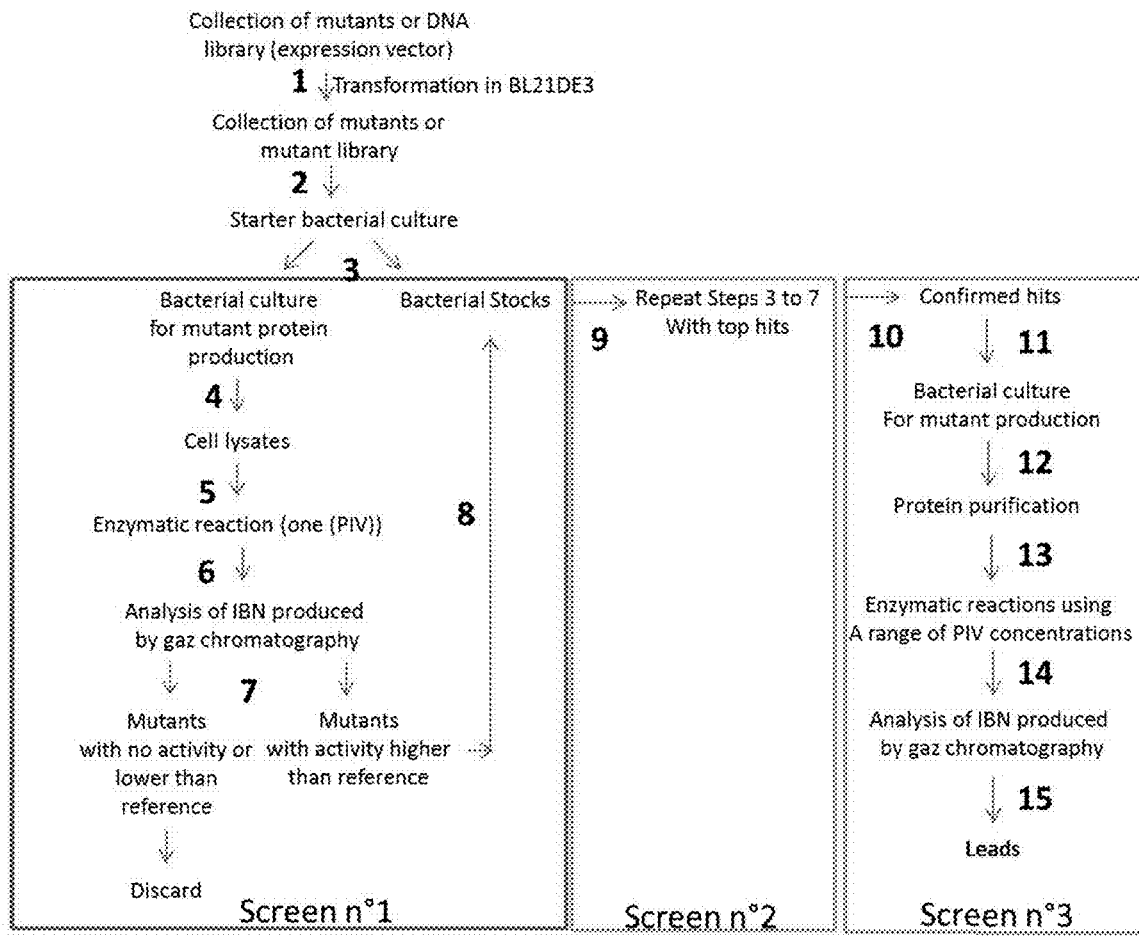

FIG. 2: General schematic outline of the screening process

Figure 3:
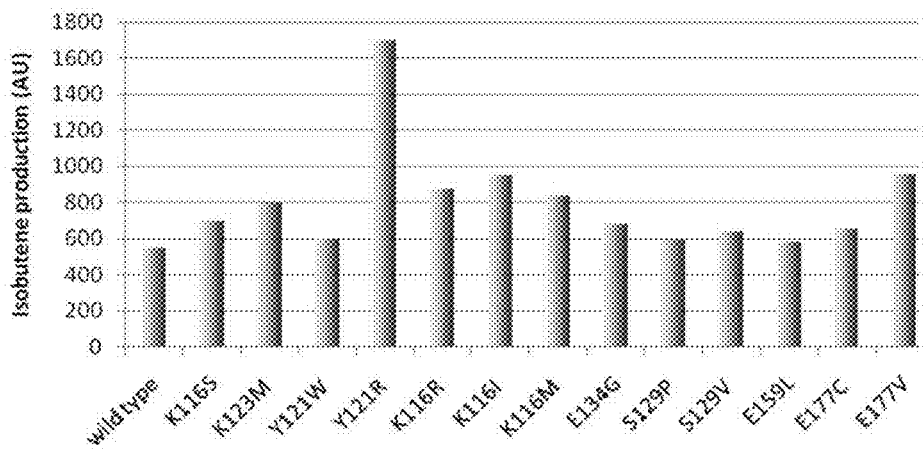
Figure 4A:
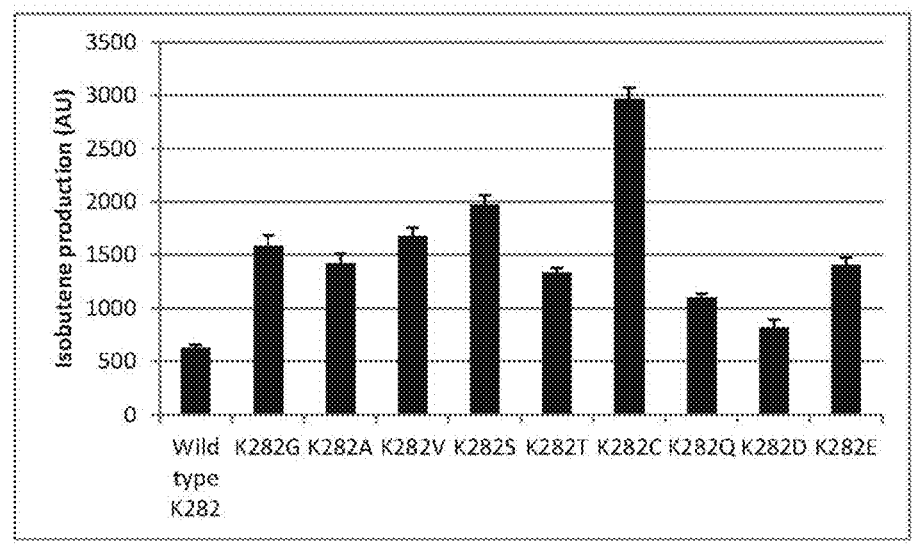
Figure 4B:
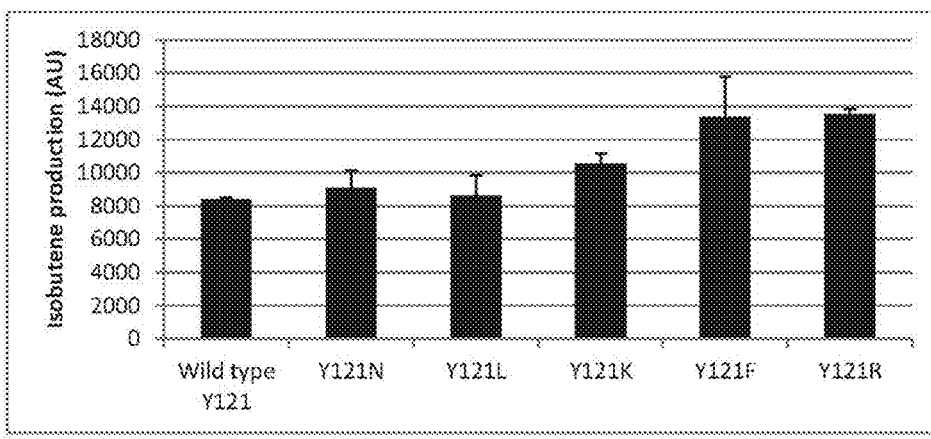

FIG. 3: Results obtained by analyzing the quantity of isobutene produced by a subset of the mutants from Table 1 using the activity assay with purified protein FIG. 4A: Panel of substitutions at position K282 that improve the activity in converting 3-phosphonoxyisovalerate into isobutene. Mutational analysis at position K282 indicates that conservative substitutions may have a similar effect on the production of isobutene. i.e.: Substitutions of K282 into nucleophilic S or C or to hydrophobic V and A increase the activity of the enzyme (assay set up using clarified cell lysate—n=3);

FIG. 4B: Panel of substitutions at position Y121 that improve the activity in converting 3-phosphonoxyisovalerate into isobutene. Mutational analysis at position Y121 indicates that conservative substitutions may have a similar effect on the production of isobutene (assay set up using crude cell lysate—n=3).

Figure 5:
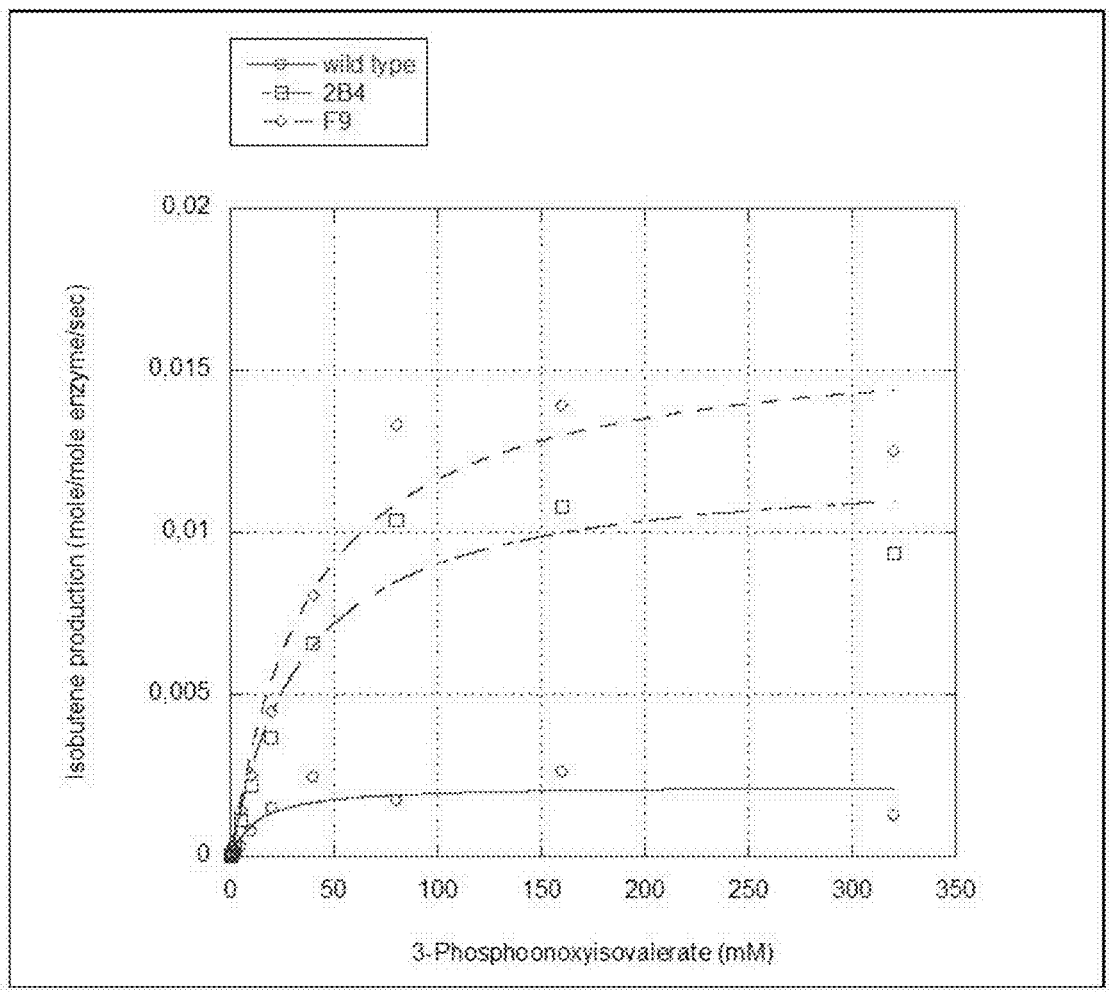

FIG. 5: The production rate of isobutene (mole of isobutene/mole enzyme/sec) was plotted as a function of the concentration of 3-phosphonooxyisovalerate and the curve was fitted using Michealis Menten equation (V=(Vmax*(substrate))/(Km+(substrate)))

Figure 6:
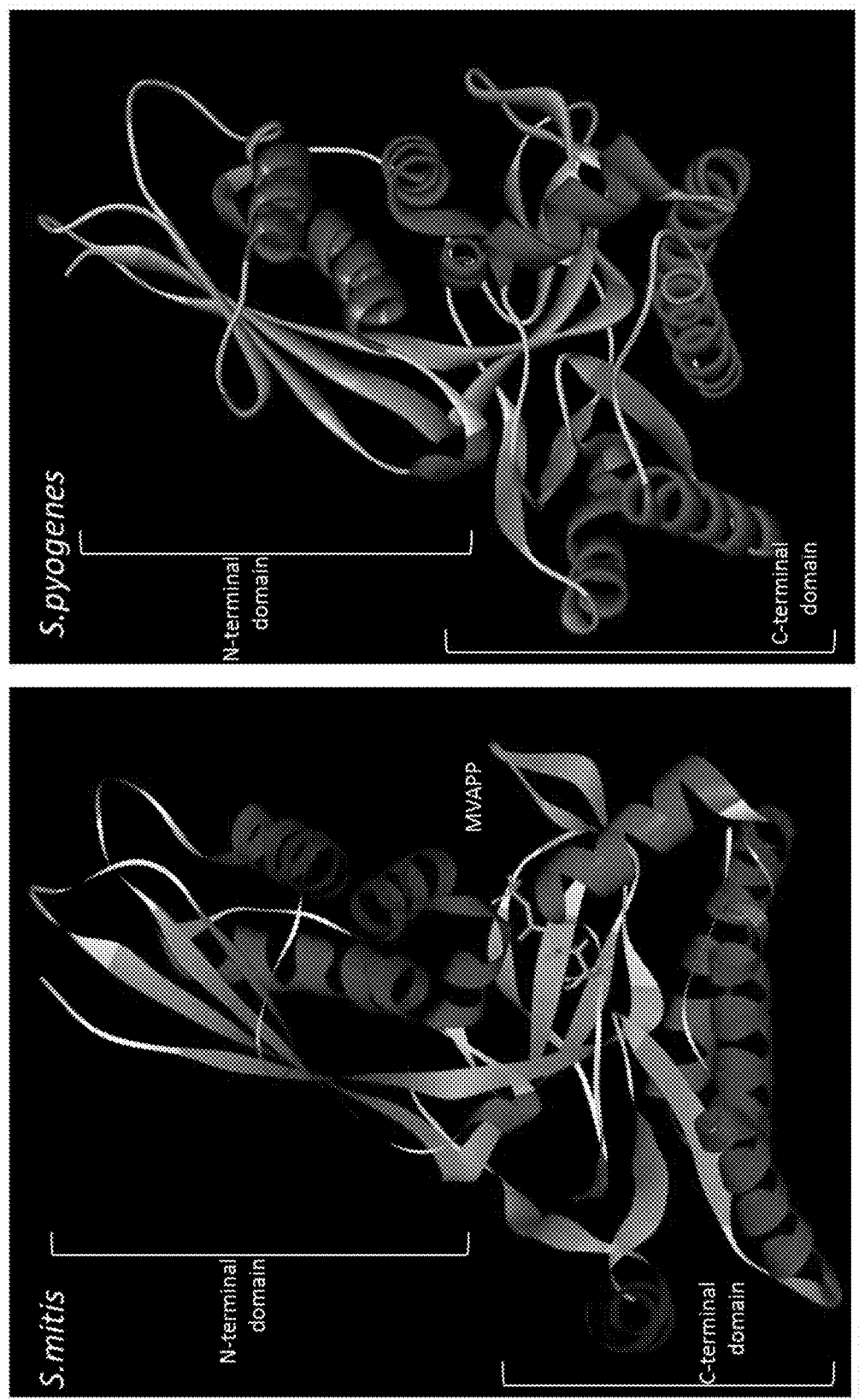

FIG. 6: 3D structure of the S. mitis MDP decarboxylase (SEQ ID NO:1) and the 3D structure of the MDP decarboxylase from S. pyogenes MDD which shows 69% sequence identity to SEQ ID NO: 1. The 3D structure was established by using the MODELER algorithm implemented in the Discovery Studio platform (version 3.0, Accelrys, San Diego, Calif.). 100 structures were generated and selection was based on minimization of total energy and analysis of the structural quality of the models according to the MODELER probability density functions. The selected structure was used for further studies. In silico mutagenesis was performed in Discovery studio 3.0 to visualize the mutations in the 2B4 variant.

Figure 7:

FIG. 7: Sequence of the MDP decarboxylase (SEQ ID NO:1) in which the secondary structure (β-sheets and α-helices) as well as the mutated residues are highlighted.

Figure 8A:

FIG. 8A: Mevalonate diphosphate decarboxylase structure is characterized by a cone-shaped fold, where the N-terminal region is orientated orthogonally against the relatively planar C-terminal region comprising 5 alpha-helices. The active site is a positively charged cleft formed between the N and C terminal domains with an ATP binding P loop nearby.

Classification of the mutations according to their location in the structure: residues are visualized in yellow.

Figure 8B:
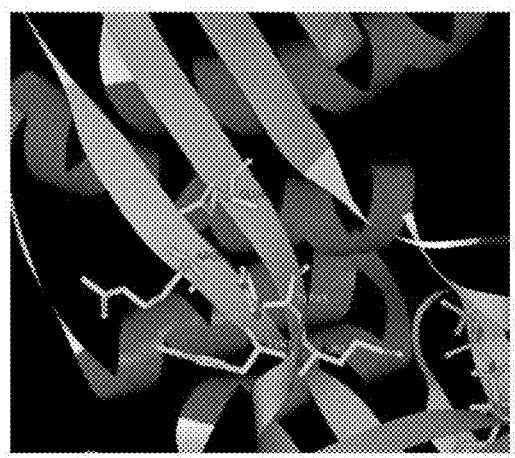

FIG. 8B: 3 D structure showing the location of residues 9, 11, 42, 43 and 45 on beta strands 1 and 4 that are directly adjacent to each other.

Figure 8C:

FIG. 8C: Residues in the C-terminal domain: The majority of these residues are situated in a region defined by alpha helices 8-9 and beta strands 9-12. Mutations targeting residues located the most C-terminally L293, F297, Q299, L303, K307 and T308 (alpha helix no 9 and beta-strand no 12) might create a more stable confirmation that stabilizes the whole structure.

FIG. 9: Scheme for the chemical synthesis of 3-phosphonoxyisovalerate.

Figure 10:
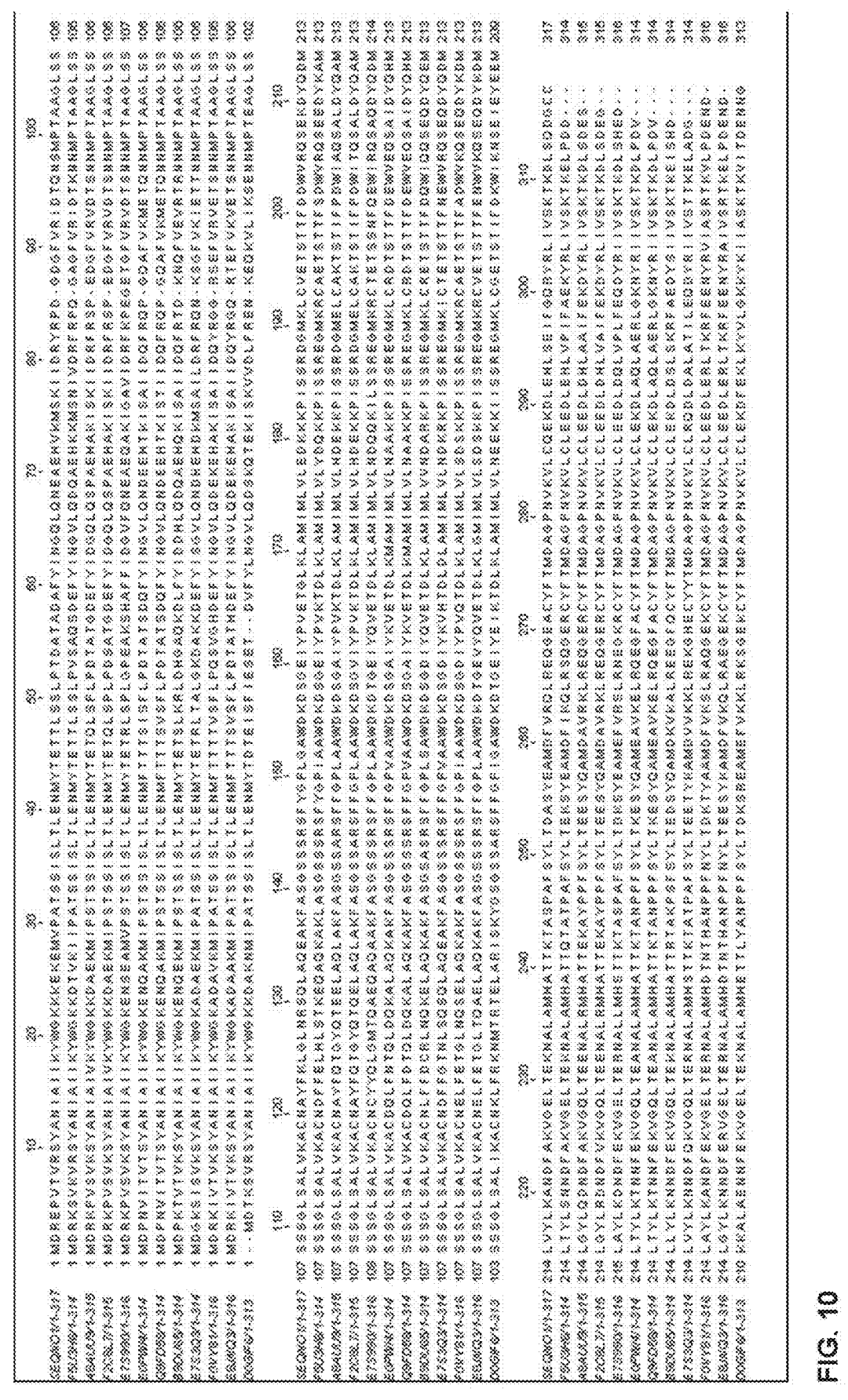

FIG. 10: Sequence alignment of SEQ ID NO:1 with MDP decarboxylases (SEQ ID NOs:5-15) showing between 60% and 80% sequence identity to SEQ ID NO:1.

Figure 11:
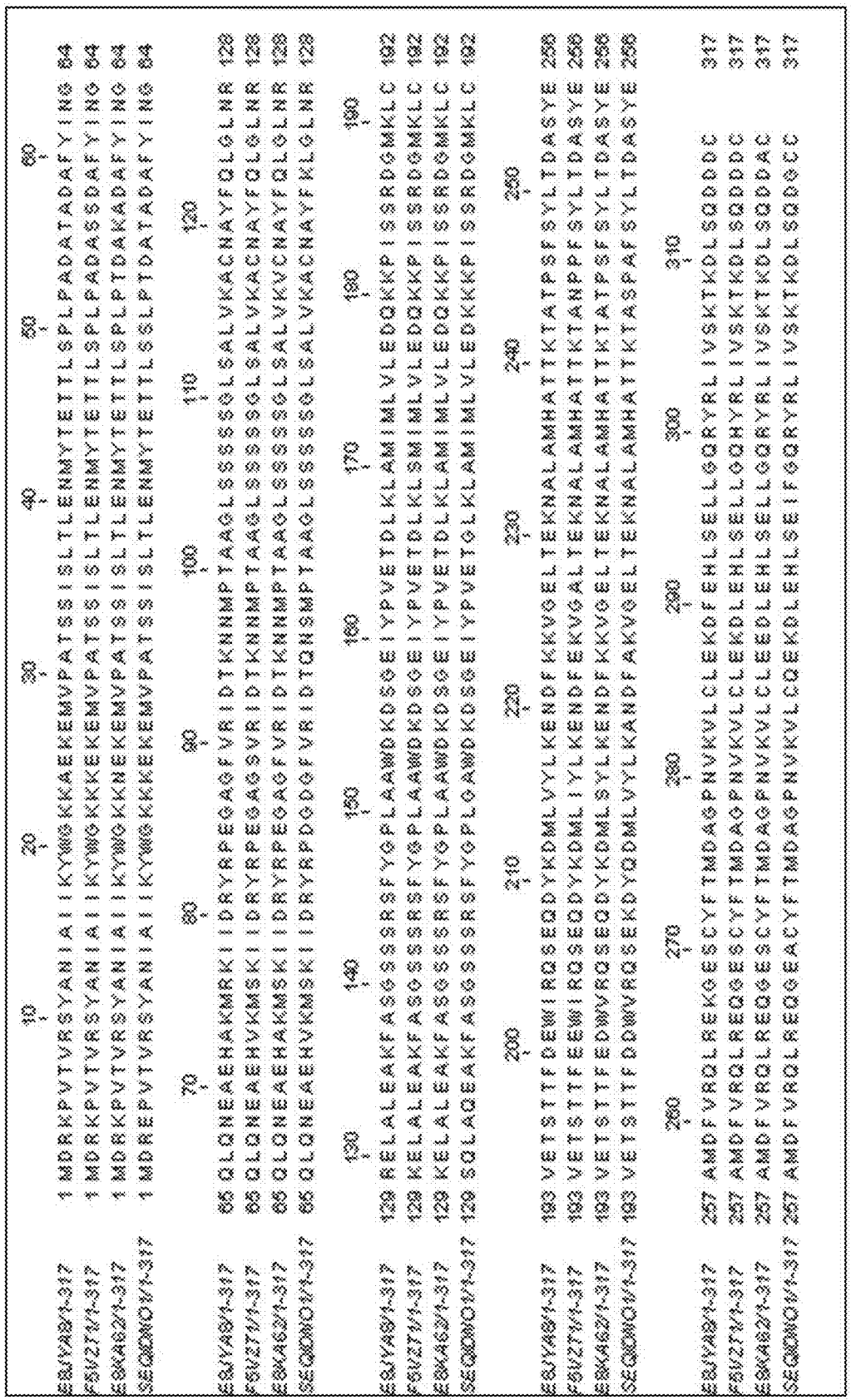

FIG. 11: Sequence alignment of SEQ ID NO:1 with MDP decarboxylases (SEQ ID NOs:16-18) showing between 80% and 90% sequence identity to SEQ ID NO:1.

Figure 12:
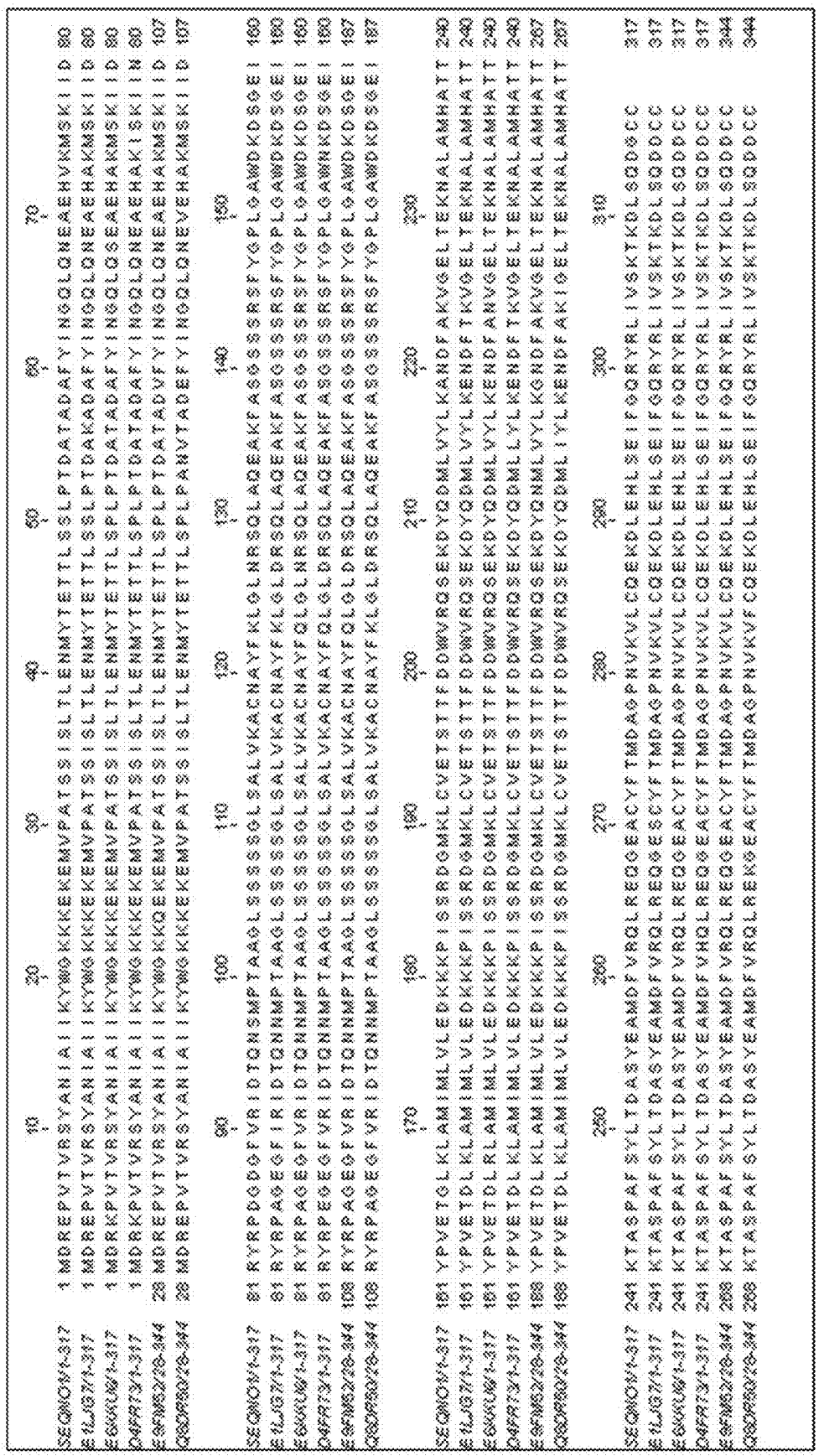

FIG. 12: Sequence alignment of SEQ ID NO:1 with MDP decarboxylases SEQ ID NOs:19-23) showing between 90% and 100% sequence identity to SEQ ID NO:1.

Figure 13:
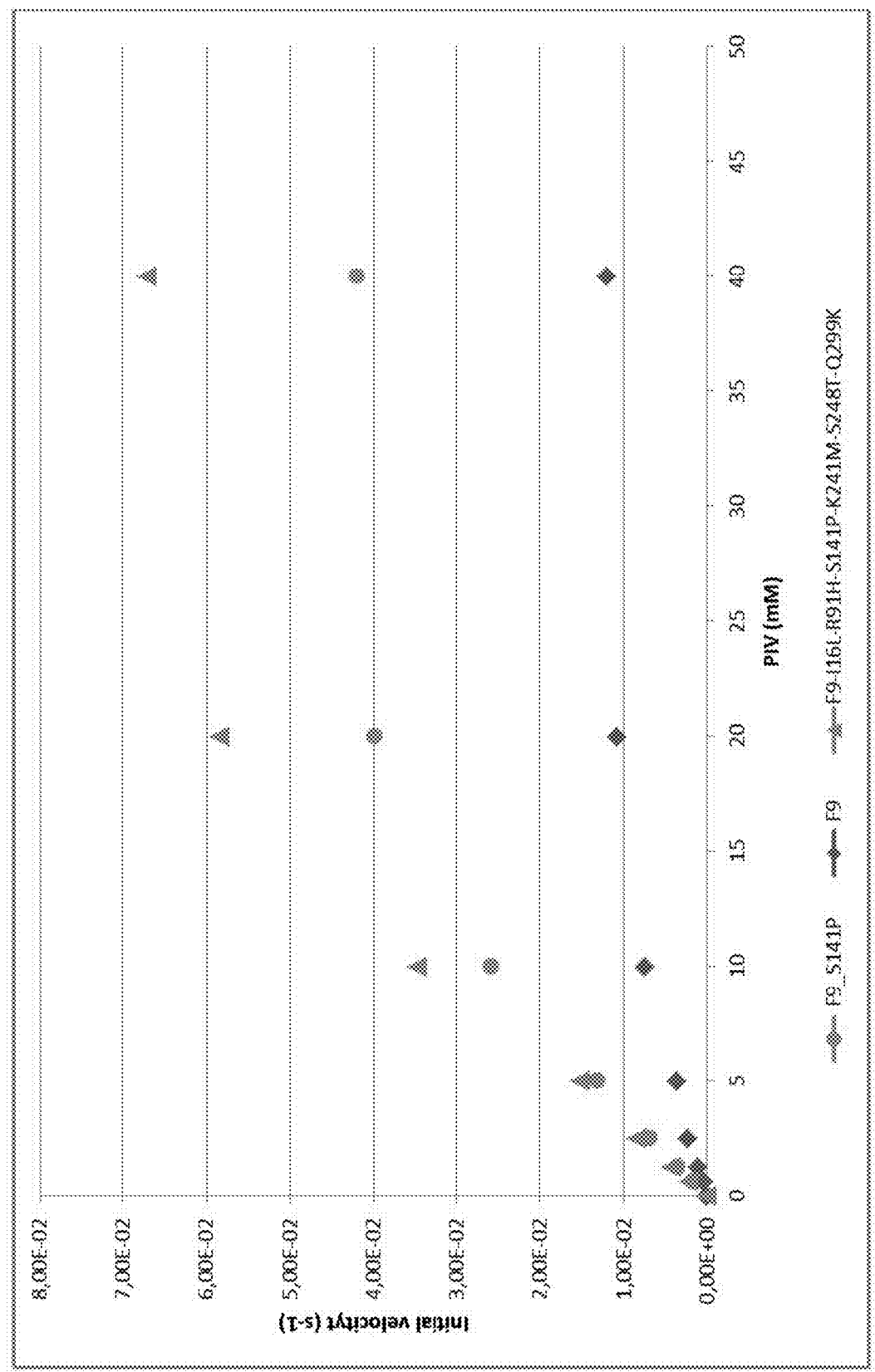

FIG. 13: Apparent kcat for MDP decarboxylase variants F9, F9-S141P, F9-I16L-R91H-S141P-K241M-S248T-Q299K.

Figure 14:
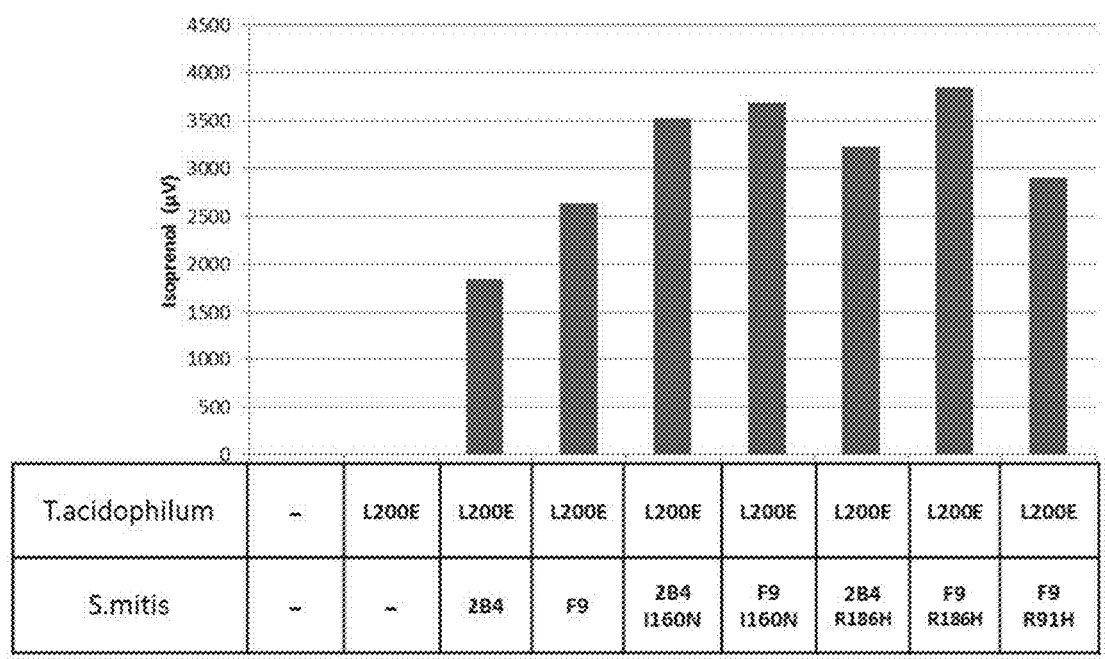

FIG. 14: Conversion of mevalonate-3-phosphate into isoprenol by several mutants.

Figure 15:
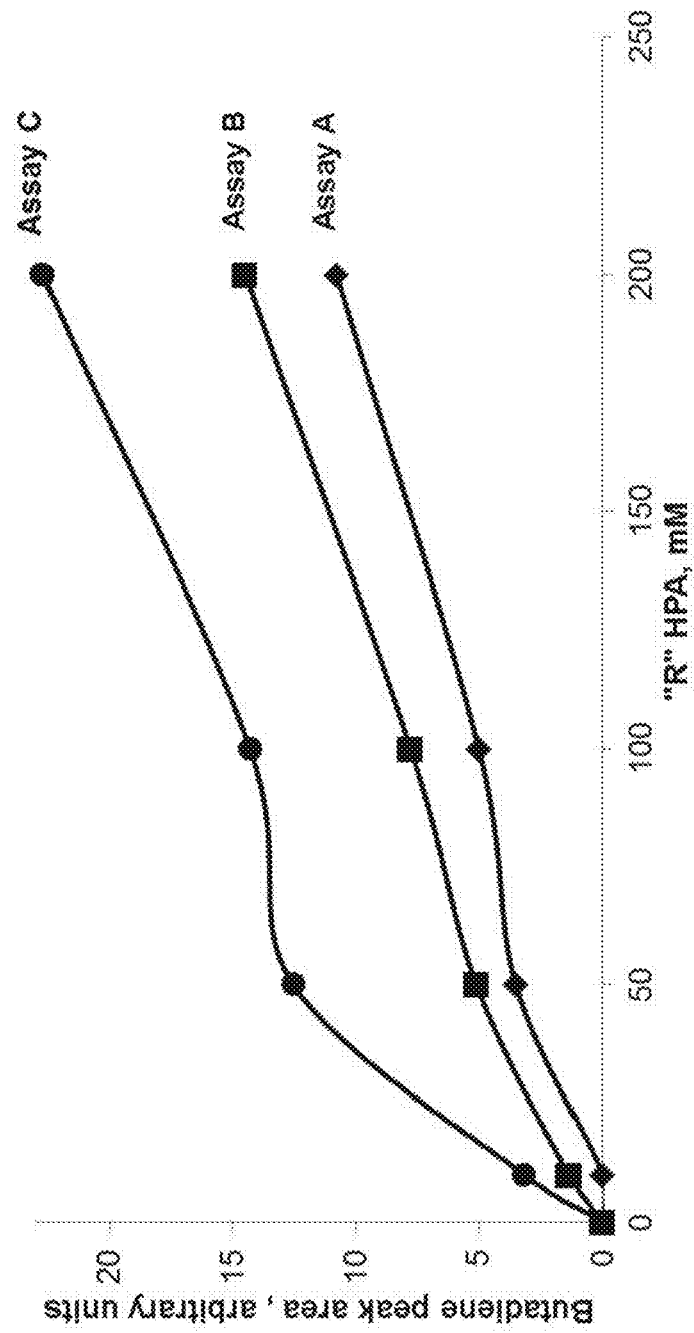

FIG. 15: shows 1,3-butadiene production from (R)-3-hydroxypent-4-enoate in the following enzymatic assays:
Assay A: without enzyme
Assay B: in the presence of 0.5 mg of MDP decarboxylase *Th. acidophilum* mutant L200E
Assay C: combined assay containing 0.5 mg of mutant L200E of MDP decarboxylase *Th. acidophilum* and 5 mg of mutant 2B4 of MDP decarboxylase *S. mitis*.

Figure 16:
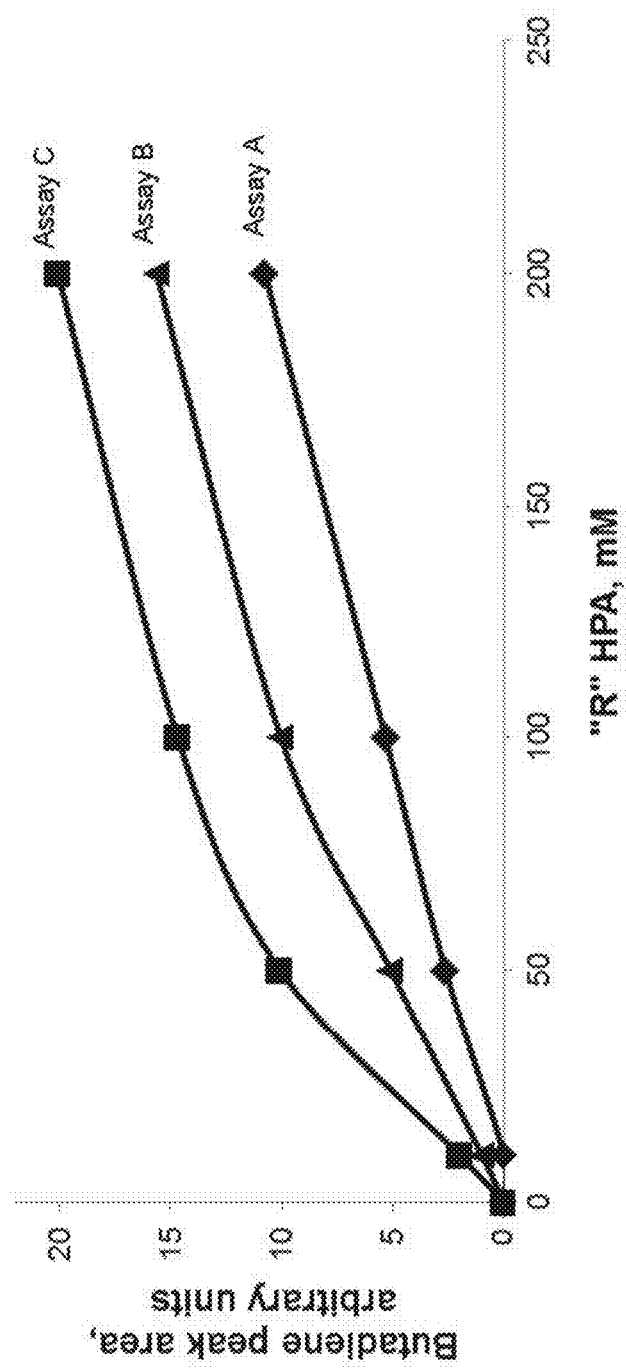

FIG. 16: shows 1,3-butadiene production from (R)-3-hydroxypent-4-enoate in the following enzymatic assays:
Assay A: without enzyme
Assay B: in the presence of 0.5 mg of MDP decarboxylase *Th. acidophilum* mutant L200E
Assay C: combined assay containing 0.5 mg of mutant L200E of MDP decarboxylase *Th. acidophilum* and 5 mg of mutant F9 of MDP decarboxylase *S. mitis*.

EXAMPLES

Materials and Methods

Methods Used to Construct and Select Mutations
a. Directed Evolution Strategy

The enzyme *Streptococcus mitis* MOP decarboxylase is capable of catalyzing, amongst other reactions, the reaction of phosphorylation of 3-hydroxyisovalerate into 3-phosphonoxyisovalerate and the reaction of decarboxylation of 3-phosphonoxyisovalerate into isobutene. A directed evolution approach was used in order to specifically improve the rate of conversion of 3-phosphonoxyisovalerate into isobutene by *S. mitis* MDP decarboxylase. This approach consisted in (1) the generation of an initial collection of single point mutants for *S. mitis* MDP decarboxylase, (2) the design of assay systems to test the activity of these enzyme variants, (3) the use of the activity assays to screen the collection of mutants in order to identify mutants with improved activity compared to the activity of the wild type *S. mitis* MDP decarboxylase, (4) additional rounds of evolution (library construction and screening) using as starting material the best mutants identified during the previous round of evolution (see FIG. 1). This approach led to the identification and characterization of a collection of mutants with increased activity compared to the wild type enzyme. During the sequential rounds of evolution, a range of molecular biology techniques were used to create the library and mutant collection to be screened. The activity assays consist generally of several steps in order to eliminate false negatives or assay artifacts amongst the initial positive hits and only retain true leads. The activity assays were modified accordingly with the increase in activity rate of the isolated mutants in order to adjust its sensitivity and throughput.

b. Construction of *Streptococcus mitis* MDP Decarboxylase Enzyme Mutants

The polynucleotide sequences coding for the different mutants identified during the evolution of the *Streptococcus mitis* MDP decarboxylase enzyme were generated using a range of standard molecular biology techniques. All these techniques used a codon-optimised polynucleotide sequence for expression in *Escherichia coli* as template (see SEQ ID NO: 4;). The sequence optimization has been done by Geneart using their GeneOptimizer software.

Different FOR-based techniques known in the art were used for the construction of single point mutants. For the generation of enzyme variants bearing multiple mutations (at least two mutations), either FOR-based techniques or other methods known in the art were used to introduce these mutations.

Following mutagenesis, the mutated polynucleotide sequence was inserted into an expression vector (used for recombinant protein production in *E. coli* and screening) either using standard ligase-based subcloning techniques, whole plasmid extension by PCR or ligase-independent cloning techniques (LIC; Life Technology Gateway® recombinant technology).

c. Selection of the Enzyme Mutants with Increased Activity

Description of the Screening Method (See FIG. 2): The DNA library or the collection of mutants inserted into the expression vector was transformed into the commercially available recombinant protein expression *E. coli* strain BL21 DE3. The DNA library transformation reaction was plated out onto LB Ampicillin plates and isolated clones were used to inoculate a starter culture. When transforming a collection of mutants, each clone was individually transformed, plated out and an isolated clone used to inoculate a starter culture; or the transformation mixture for each individual clone was directly used to inoculate a starter culture. The protein expression was carried out using an auto-induction medium (ZYM-5250) as described in Studier F. W (Protein Expr. Purif. 41 (2005), 207-234) with an initial cell growth phase for 6 hours at 37° C. and an induction stage overnight at 28° C. After the transformation, all subsequent steps were carried out in microplates or deepwell plates. The cell cultures were centrifuged and the pellets were stored for at least 1 hour at −80° C. The cell pellets were then resuspended in a small volume of buffer and lysed by sonication before being subjected to centrifugation for the removal of cell debris.

Screening for Variants with an Increased Activity of Converting 3-Phosphonoxyisovalerate into Isobutene To test the activity of the mutant enzyme to catalyze the conversion of 3-phosphonoxyisovalerate into isobutene, a reaction mix was prepared in glass GC vials by mixing cell lysates (supernatant), 3-phosphonoxyisovalerate substrate in 50 mM Tris pH 7 final concentration, 3-phosphonoxyisovalerate has been prepared enzymatically by incubating 3-hydroxyisovalerate, purified Thermoplasma *acidophilum* MOP decarboxylase and cofactors (ATP, $MgCl_2$, KCl) at 37° C. for 24 hours. The reaction mixture was incubated for varying length of time at 37° C. and the gas phase was injected in a gas chromatograph alongside the appropriate references (isobutene for calibration, wild type enzymes, negative controls . . . ). Following analysis of the GC chromatograms, mutants showing an activity increased by at least 20% were selected and subjected to a second round of screening which followed the same conditions as the primary screen.

The final step in the selection process included the production and purification of the top hits, i.e. enzyme variants with the highest improved activity validated by the primary and secondary screens and their activity was tested with different substrate concentrations. Confirmed hits were further characterized and the kcat and Km for the reaction was calculated.

Modification of the Screening Process:

As mentioned before, the screening protocol was regularly modified as new improved mutants were identified. The main modification of the protocols covers the following points:
- Cell culture conditions: mode of inoculation (using isolated clone or transformation reaction), medium volume (200 μl to 5 ml), 24 deepwell plates, 96 deepwell and standard 96-well microplates, agitation varies according to the type of shaker incubator
- Cell lysis: type and volume of buffer used, sonication or no sonication, centrifugation or not (crude lysate can be used effectively)
- Set up of the enzymatic reaction:
  - Either 3-phosphonoxyisovalerate is enzymatically prepared prior to the assay (concentration of enzyme T. acidophilum, cofactors, HIV variable as well as the incubation time and temperature)
  - The reaction of phosphorylation of 3-hydroxyisovalerate and the decarboxylation of 3-phosphonoxyisovalerate into isobutene is combined in one tube: S. mitis MDD mutant is combined with purified T. acidophilum and 3-hydroxyisovalerate. The reaction is incubated and assayed for the presence and quantity of isobutene,
  - Pure 3-phosphonoxyisovalerate compound chemically synthesized is used in the assay. 3-phosphonoxyisovalerate (PIV) was chemically synthesized from 3-hydroxyisovalerate according to the scheme depicted in FIG. 9 by SYNTHEVAL (France)
  - Subjecting the enzymatic reaction to agitation during incubation leads to a 5 fold increase in signal
- Number of steps in the screening can vary
- Number of replicates analyzed for each clone vary (1 reaction per clone in the primary screens, clone can be tested in duplicate, triplicate or more in the following screens)
- Method of GC analysis can vary: type of columns, type of vials and septa, and method (oven, injectors, detectors, temperature, time of analysis . . . )

Example 1: Identification of Single Point Mutants of S. mitis MDP Decarboxylase with Increased Activity for the Reaction of Conversion of 3-Phosphonoxyisovalerate into Isobutene A collection of 2632 single point mutants of S. mitis MDP decarboxylase was prepared using standard molecular biology techniques. Saturation mutagenesis aimed at substituting systematically all the 317 amino acids of S. mitis MDP decarboxylase with the 19 non wild type amino acids. The average number of substitutions per position was 8 out of the 19 possible. The coding sequence for each individual mutant was sub-cloned in an expression vector to allow the production of an N-terminal 6-His-tagged recombinant mutant enzyme in E. coli.

The recombinant protein expression E. coli strain BL21 DE3 was transformed with the expression vectors encoding the mutant enzymes, the empty expression vector (negative control) and the expression vector encoding the wild type enzyme (positive control). To speed up the process, the transformation was carried out in a 96-well plate. Briefly, 2 μl of DNA plasmid miniprep of each mutant and each control was transferred per well into a 96-well 0.2 ml FOR reaction plate before addition of 40 μl/well of chemically competent BL21 DE3 E. coli cells. The plate was incubated on ice for 15 minutes before carrying out a heatshock for 1 minute at 42° C. in the AB 2720 Thermal cycler. The plate was then immediately placed on ice and cooled for 1 minute before 1 ml of sterile Luria-Bertani medium was added (10 g/l Tryptone, 5 yeast extract, 10 g/l NaCl, pH 7). The plate was sealed using gas-permeable adhesive film and incubated for 45 minutes at 37° C. at 200 rpm in an Infors Minitron orbital shaker. 50 μl of the transformation mixture was then used to inoculate 0.5 ml of Luria-Bertani medium supplemented with 100 μg/ml ampicillin placed in a 96 deep-well plate. These plates were sealed and incubated overnight at 37° C. at 200 rpm. Bacterial stocks were prepared in a 96-well plate by mixing 100 μl of the overnight starter cultures with 35 μl sterile 50% glycerol and stored at −80° C. until further use.

For the production of the recombinant mutant enzyme, 1 ml of sterile autoinduction medium (Studier F. W, Protein Expr. Purif. 41 (2005), 207-234) supplemented with the appropriate antibiotic, was distributed in the wells of a 96-deep well plate and said wells were inoculated with 10 μL of thawed glycerol stocks. Each plate contained approximately 70 to 80 distinct mutant enzymes, 8 negative controls (empty expression vector) and 8 wild type enzyme clones for use as a reference. Plates were incubated for 6 hours at 37° C. at 1000 rpm in a Heidolph Titramax orbital shaker followed by a further overnight incubation at 28° C. at 1000 rpm. Bacterial cells were pelleted by centrifugation for 20 minutes at 3200×g at 4° C. Cell pellets were stored at −80° C.

Pellets were thawed on ice for 5 to 10 minutes and were resuspended in 250 μl of resuspension buffer (50 mM Tris-CI pH7, 20 mM KCl, 10 mM $MgCl_2$, 10% glucose, 1 μl/ml Merck-Novagen Lysonase). Cell suspensions were incubated at room temperature for 15 minutes and on ice for 30 minutes. Bacterial cells lysis was carried out by sonicating these cell suspensions for 4 pulses of 5 minutes in an Advantage Lab ultrasonic water bath filled with ice and water (5 minutes of rest on ice between pulses). Cell lysates were then centrifuged for 20 minutes at 10° C. at 3200×g to pellet cell debris and 240 μl of the supernatants were transferred into a fresh plate. The enzymatic reaction was set up in Agilent 2 ml glass vials by mixing 200 μl of the supernatant with 300 μl of 3-phosphonoxyisovalerate substrate. The vials were hermetically sealed using crimp caps (PTFE-silicon-PTFE coated), incubated in a waterbath for 24 hours at 37° C. and stored at −20° C. prior to analysis by gas chromatography. To prepare 3-phosphonoxyisovalerate substrate, 0.063 mg/ml of purified Thermophilus acidophilum MDP decarboxylase was mixed with 50 mM hydroxyisovalerate, 40 mM Adenosine tri-phosphate in a 50 mM Tris-CI pH7, 20 mM KCl, 20 mM $MgCl_2$ and incubated for 24 hours at 45° C. This enzymatically prepared 3-phosphonoxyisovalerate substrate was aliquoted and stored at −20° C. until further use.

The isobutene produced by the enzymatic reaction in the presence of S. mitis MDP decarboxylase was quantified by gas chromatography. The vials were thawed quickly at 30° C. for 30 minutes and placed on an automated sampler mounted onto a Varian GC-430 system equipped with a Varian CP SilicaPlot column (30 m×0.32 mm), one injection port and one Flame Ionization detector (FID). The sampler was set up to inject 100 µl of headspace gas. For the GC analysis method used to detect isobutene, oven temperature was set to 185° C., injector port temperature was set to 150° C. with a split ratio of 4:1 and the FID detector to 250° C.

cation kit according the users' manual. The activity was determined by mixing in a 2 ml GC vial: 500 µg of purified enzyme, 300 µl of 3-phosphonoxyisovalerate substrate and the volume was adjusted to 500 µl with 50 mM Tris-Cl pH7. The reaction was incubated for 24 hours at 37° C. and stopped by freezing the samples at −20° C. The quantity of isobutene produced was determined by GC analysis.

This screening procedure led to the identification of 71 mutations which confer S. mitis MDP decarboxylase an increased activity of isobutene production. Table 4 lists the position and type of substitutions that have been identified. FIG. 3 shows the results obtained by analyzing the quantity of isobutene produced by a subset of the mutants from Table 4 using the activity assay with purified protein. Additional data is represented by FIG. 4 a) and b).

TABLE 4

List of the position and type of substitutions that have been identified.

| | R9 | Y11 | M42 | Y43 | E45 | L66 | K77 | K116 | C118 | A120 | Y121 | K123 | S129 | E134 | % increase compared to wild type enzyme |
|---|---|---|---|---|---|---|---|---|---|---|---|---|---|---|---|
| Substitutions | | | | | | | | | | | | | | | >300% |
| | | | | | | | | | | | R | | | | >200% |
| | | | | | | | | | | | | | | | >100% |
| | | | | | | | | | | | | | | | 75-100% |
| | | | | | | | | R, I | | | | | | | 50-75 |
| | | C | A | | L | | | S, M | | | N, L, R, I | M | | | 25-50% |
| | L | F | | L | F, M, V | H | N | L | | | V | W | P, V | G | 10-25% |

| | E159 | I160 | M173 | E177 | R186 | T251 | A253 | K282 | L293 | F297 | Q299 | L303 | K307 | T308 | % increase compared to wild type enzyme |
|---|---|---|---|---|---|---|---|---|---|---|---|---|---|---|---|
| Substitutions | | | | | | | | C | | | | | | | >300% |
| | | | | | | | | S | | | | | | | >200% |
| | | | | | | | | E, G | | | | | | | >100% |
| | | | | | | | | Q, T, V, A | | | | | | | 75-100% |
| | L | | | | M | | | | | | | | | | 50-75 |
| | | V | C | V | | | | D, | F, W | C | | M | | | 25-50% |
| | | | | C | H | F, V | V, I | | | L | P | | H | S | 10-25% |

The GC uses nitrogen as carrier gas (constant flow of 1.5 ml/min) and a mixture of air (air flow 28 ml/min) and hydrogen (300 ml/min) for the FID detection system. The duration of the analysis was approx. 3 minutes per sample and under these conditions isobutene was observed to elute at 2.5 min. A sample of commercially bought pure isobutene was injected prior to the start of the analysis to calibrate the GC system and to determine the retention time for isobutene. Following the analysis, chromatograms were processed using Galaxy software; the area under the peak was integrated for each mutant and compared to that of the wild type enzyme, Mutants showing an increase of at least 10-15% of isobutene production compared to the amount produced by the wild type enzyme were tested for a second time according to the protocol described above in order to eliminate false positives. Finally all mutant enzymes that have been selected through these two rounds of screening were tested once again using normalized quantities of purified protein in the assay. Briefly, the bacterial glycerol stocks of the selected mutant enzymes were used to inoculate 7 ml of LB-Amp. 2 ml of this starter culture was used to inoculate 200 ml of autoinduction medium and the plasmid DNA was extracted from the 5 ml of culture leftover. The plasmid DNA was sequenced to confirm the presence and the type of a mutation. The bacterial expression for the production of the mutant enzymes was carried out as previously described and the N-terminal 6His-tagged mutant enzymes were purified from the pellet using Macherey-Nagel Protino purification Example 2: Characterization of Variants of S. mitis MDP Decarboxylase with High Turnover Rate A collection of S. mitis MDP decarboxylase variants has been created by combining a selection of single point mutations which confer high increase in activity (increase of at least 50% compared with the activity of the wild type enzyme) using FOR-based techniques. Additional diversity was also created by random mutagenesis. The quantity of isobutene produced by these variants was determined in an enzymatic assay whereby 500 µg of purified enzyme was mixed to 300 µl of 3-phosphonoisovalerate substrate in 50 mM Tris-Cl pH7 buffer. Following a 24-hour incubation period at 37° C., the reaction was stopped by freezing the samples at −20° C. and the quantity of isobutene produced was determined by GC analysis. For the GC headspace assay, 100 µl of the headspace gas was injected in the injector port of a Varian GC-430 system equipped with a Varian CP SilicaPlot column (30 m×0.32 mm) and a FID. The GC analysis method used to detect isobutene is characterized by an oven temperature at 185° C., injector port temperature at 150° C. with a split ratio of 1:10 and the FID detector temperature at 250° C. Nitrogen was used as carrier gas (constant flow of 1.5 ml/min) and a mixture of air (air flow 28 ml/min) and hydrogen (300 ml/min) were used to supply the FID detection system.

A number of variants showing mutations of up to 11 positions have been identified which show an increased activity in the activity assay. The different variants are shown in the following Tables.

TABLE 5

Double mutants

| Mutations | % increase in activity compared to wild type enzyme |
|---|---|
| K282CM42A | 483 |
| K282CL264Q | 453 |
| K282CL303M | 510 |
| K282CC118L | 465 |
| K282CA253i | 493 |
| K282CA120N | 507 |
| K282CE45M | 516 |
| K282CF297L | 471 |
| K282CY11C | 508 |
| K282CY121R | 400 |
| K282CS129V | 514 |
| K282CA120L | 435 |
| K282CK116L | 440 |
| K282R9L | 428 |
| K282CY11E | 270 |
| K282CE177V | 493 |
| K282CK116R | 479 |
| K282CA120I | 205 |
| K282CK116M | 576 |
| K282CT251M | 452 |
| K282CL293F | 375 |
| K282CK123M | 178 |
| K282CF122M | 233 |
| K282CY121L | 290 |

TABLE 6

Triple mutants

| Mutations | % increase in activity compared to wild type enzyme |
|---|---|
| E45LY121RK282C | 420 |
| K282CY121RY11E | 230 |
| K116IY121RK282C | 147 |
| Y121RE177VK282C | 524 |
| A120RY121LK282C | 184 |
| M173CK282CF297L | 500 |

TABLE 7

Combinations of 4 mutations

| Mutations | % increase in activity compared to wild type enzyme |
|---|---|
| Y121RK282CL303MT308S | 377 |
| M173CL303MK307HT308S | 480 |
| E45VM173CK282CL303M | 500 |

TABLE 8

Combinations of 5 mutations

| Mutations | % increase in activity compared to wild type enzyme |
|---|---|
| Y121RM173CK282CL303MT308S | 507 |
| E159LM173CL303MK307HT308S | 480 |
| R9LY11FL303MK307HT308S | 440 |
| C118LY121RM173CK282CL303M | 500 |

TABLE 9

Combinations of 6 mutations

| Mutations | % increase in activity compared to wild type enzyme |
|---|---|
| Y121RE159LM173CK282CL303MT308S | 558 |
| Y121RE159LM173CV215AK282CL303M | 500 |
| E45LE159LM173CK282CF297LT308S | 550 |

TABLE 10

Combinations of 7 mutations

| Mutations | % increase in activity compared to wild type enzyme |
|---|---|
| Y121RE159LM173CK282CL303MK307HT308S | 643 |
| E45VY121RE159LM173CK282CL303MT308S | 500 |
| Y121RE159LM173CK282CF297LL303MT308S | 500 |
| C118LY121RE159LM173CK282CL303MT308S | 500 |
| Y121RE159LM173CE177CK282CL303MT308S | 500 |
| Y121RE159LM173CT242AK282CL303MT308S | 500 |
| C118LY121RE159LM173CK282CL303MG315S | 500 |
| C118WY121RE159LM173CE177CK282CL303M | 500 |
| C118LY121RE159LM173CE177CK282CL303M | 500 |
| E45VY121RM173CK282CF297LL303MT308S | 500 |
| E45VC118LY121RM173CK282CL303MT308S | 550 |
| E45VY121RE159LM173CK282CF297LL303M | 550 |

TABLE 11

Combinations of 8 mutations

| Mutations | % increase in activity compared to wild type enzyme |
|---|---|
| D80GY121RE159LM173CK282CL303MT308SG315S | 500 |
| K24RY121RE159LK123RM173CM258LK282CL303M | 500 |
| C118LY121RE159LM173CE177CV215AK282CL303M | 500 |
| K24RC118LY121RE159LM173CE177CK282CL303M | 500 |
| E45VD80GY121RM173CK282CF297LL303MT308S | 500 |
| E45LY121RE159LM173CE177CK282CL303MT308S | 550 |

TABLE 12

Combinations of 9 mutations

| Mutations | % increase in activity compared to wild type enzyme |
|---|---|
| C118LY121RE159LM173CE177CK282CF297LL303MT308S | 500 |
| C118LY121RE159LM173CE177CV215AK282CF297LL303M | 500 |
| D80GC118LY121RE159LM173CE177CK282CL303MG315S | 500 |
| K24RE45VY121RK123RM173CK282CF297LL303MT308S | 550 |
| E45VY121RE159LM173CE177CV215AM258LK282CL303M | 550 |

TABLE 13

Combinations of 10 mutations

| Mutations | % increase in activity compared to wild type enzyme |
|---|---|
| E45VC118LY121RE159LM173CV215AK282CF297LL303MT308S | 500 |

TABLE 14

Combinations of 11 mutations

| Mutations | % increase in activity compared to wild type enzyme |
|---|---|
| K24RC118LY121RE159LM173CE177CK282CE291DF297LL303MT308S | 750 |

Two variants named 2B4 (SEQ ID NO:2) and F9 (SEQ ID NO:3) as having high increase in activity in the assay were selected for further characterization. The 2B4 and F9 protein sequence contain 6 and 11 mutations respectively compared to the wild type enzyme (see Table 15). F9 carries two novel mutations, K24R and E291D that were not identified in the original single point mutations screen.

TABLE 15

Mutations of variants 2B4 and F9

| ID | Mutations | total mutation |
|---|---|---|
| 2B4 | Y121RE159LM173CK282CL303MT308S | 6 |
| F9 | K24RC118LY121RE159LM173CE177CK282CE291DF297LL303MT308S | 11 |

Michaelis Menten $k_{cat}$ and $K_m$ steady-state kinetics constants were determined for these two variants as follows: a series of enzymatic reactions were set up in GC vials with 200 μg of purified 2B4, F9 or the wild type enzyme, a range of 0 to 320 mM of chemically synthesized 3-phosphonooxy-isovalerate, 5 mM ATP, 20 mM KCl, 10 mM $MgCl_2$ and 50 mM Tris-CI pH 7.5. The vials were sealed and incubated for 15 hours at 37° C. before analysing the isobutene produced by GC as previously described. Previous experiments had determined that the rate of isobutene production in this experimental set up was constant in the 20 first hours of the enzymatic reaction and thus the rate of isobutene produced per hour as determined after 15-hour incubation is equal to the initial rate of isobutene production at the beginning of the reaction. In order to quantify the absolute amount of isobutene produced by the reaction, the GC was calibrated using a range of concentration of pure isobutene (0 to 10,000 ppm). The calibration table was found to be linear in this range of isobutene concentration. The production rate of isobutene (mole of isobutene/mole enzyme/sec) were plotted as a function of the concentration of 3-phosphonooxy-isovalerate and the curve was fitted using Michealis Menten equation $(V=(V_{max}*(substrate))/(K_m+(substrate)))$ (FIG. 2) to extract the kcat (s−1) and Km values (mM) that are summarized in Table 16. As shown in FIG. 5 and Table 16, variants 2B4 and F9 had a higher kcat than the wild type enzyme.

TABLE 16

Summary of the kcat (s−1) and Km values (mM) of the variants 2B4 and F9

| ID | Km (mM) | kcat (10−3 · s−1) | kcat/Km (mM−1 · s−1) |
|---|---|---|---|
| wild type enzyme | 12.5 | 2.2 | 0.18 |
| 2B4 | 34.4 | 12 | 0.35 |
| F9 | 38.38 | 16 | 0.42 |

Example 3: Identification of Variants of *S. mitis* MDP Decarboxylase with Further Increased Activity for the Reaction of Conversion of 3-Phosphonoxyisovalerate into Isobutene Additional MVD variants with a further enhanced activity in converting 3-phosphonoxyisovalerate into isobutene were identified through successive rounds of mutagenesis, recombination of point mutations and in vitro and/or in vivo screening assay. The list of these MVD variants is presented in the following Table 17.

TABLE 17

| Mutations added to F9 variant | Fold Increase | Screening Assay |
|---|---|---|
| S141P | 3 | IN VITRO |
| S141T | 2 | IN VITRO |
| S105A | 1.8-2 | IN VITRO |
| Q299K | 1.25 | IN VITRO |
| I16L | 1.25 | IN VITRO |
| S248T | 1.4 | IN VITRO |
| K241M | 1.25 | IN VITRO |
| I16L S105A | 2.2 | IN VITRO |
| S141P K241M S248T | 3.1 | IN VITRO |
| I16L R91H S141P K241M S248T | 3.5 | IN VITRO |
| I16L S141P | 3.5 | IN VITRO |
| I16L R91H S141P K241M S248T Q299K | 3.6 | IN VITRO |
| I16L S141P K241M | 3.6 | IN VITRO |
| I16L S141P K241M S248T | 3.7 | IN VITRO |
| I16L R91H S141P K241M S248T Q299K M28K | 7.24 | IN VITRO |
| I16L R91H S141P K241M S248T Q299K M28A | 5.48 | IN VITRO |
| I16L R91H S141P K241M S248T Q299K K180P | 5.00 | IN VITRO |
| I16L S141P K241I S248T | 5.25 | IN VIVO |
| I16L S141P K241I S248T M28K | 8.37 | IN VIVO |
| I16L S141P K241I S248T M28K K180P | 11.55 | IN VIVO |
| I16L S141P K241I S248T M28K T53V K180P | 11.97 | IN VIVO |
| I16L S141P K241I S248T M28K K180P A238K | 15.015 | IN VIVO |
| I16L S141P K241I S248T M28K K180P A238R | 16.17 | IN VIVO |
| I16L S141P K241I S248T M28K K180P C282V | 15.015 | IN VIVO |
| I16L S141P K241I S248T M28K K180P P279A | 17.325 | IN VIVO |
| I16L S141P K241I S248T M28K K180P Y161R | 16.17 | IN VIVO |

The fold increase is the ratio of MDP decarboxylase variant activity over wild type MDP decarboxylase activity. The fold increase is determined for one substrate concentration (1 or 2 mM PIV for in vitro assay and 500 mM acetone for in vivo assay). The quantity of the enzyme is not normalised but these MVD variants are expressed in similar amounts as observed on SDS-PAGE analysis of cell lysates.

The template for mutagenesis was the variant named "F9" which corresponds to the *S. mitis* MOP decarboxylase of SEQ ID NO:1 with the following mutations: K24RC118LY121RE159LM173CE177CK282CE291 DF297LL 303MT308S (see SEQ ID NO: 3). The in vitro screening assay used was the one described herein-above section c of Materials and Methods, preferably an in vitro assay involving the use of cell lysate.

For the in vivo testing a further in vivo assay was developed. This assay is based on the use of a bacterial strain transformed with an expression vector that contains the coding sequences and lead to the production of the 3 enzymes involved in the metabolic pathway converting acetone to isobutene; namely for the production of 3-hydroxyisovalerate (HIV) the *M. musculus* HMG-CoA synthase (referred to in the following as HIV synthase) was used; for the phosphorylation of 3-hydroxyisovalerate into 3-phosphonoxyisovalerate (PIV) the *T. acidophilum* MDP decarboxylase was used (referred to in the following as HIV phosphorylase) and for the conversion of PIV into isobutene (IBN) by decarboxylation the *S. mitis* MDP decarboxylase variant to be tested was used (referred to in the following as PIV decarboxylase). This strain is first cultured, overnight in a shaking incubator at 30° C./1000 rpm, in 1 ml of auto-induction culture medium to produce the three types of recombinant enzymes. The cell pellet containing these three overexpressed recombinant enzymes is then resuspended in 500 µl of minimum medium supplemented with 500 mM acetone and incubated for a further 16 hours in a shaking incubator set at 37° C./1000 rpm. During this second step, HIV synthase catalyses the condensation of acetone (from the medium) with the cellular acetyl CoA into HIV which is then sequentially converted into PIV and IBN by the HIV phosphorylase and the PIV decarboxylase using the cellular ATP. The IBN produced is then quantified by gas chromatography using the same method as the in vitro screening assay described in section c of Materials and Methods.

The main advantages of this assay are as follows: (1) the production of IBN occurs within the cell, (2) cellular metabolites (ATP and acetylCoA) and cellular co-factors are used, only acetone is added to the reaction (acetone being a none limiting factor in this pathway due to the efficiency of the clostridial acetone pathway) (3) the increase in IBN production is measured in the context of the complete IBN production pathway and takes into account not only the cooperation of the three enzymes of interests, but also the presence of potential endogenous inhibitors or competitors and low substrate concentrations, (4) enzymes are in their most native form and are not subjected to any form of extraction of a purification process that could denature them and negatively affect their activity.

For some above described variants, the fold increase in activity has also been determined over a range of substrate concentrations in order to calculate kinetic parametres (apparent kcat and Km) using equal quantities of MDP decarboxylase variants. The fold increase for the apparent kcat is generally similar to that determined in the screening assays (see FIG. 13). In FIG. 13, the fold increase for F9-S141P kcat is approx. x3.5 of the F9 kcat compared to x3 determined in the screening assay; the fold increase for F9-I16L-R91H-S141P-K241M-S248T-Q299K kcat is approx. x5.5 of the F9 kcat compared to x3.7 determined in the screening assay.

Example 4: Variants of *S. mitis* MDP Decarboxylase Also Show an Increased Activity in Catalyzing the Conversion of Mevalonate-3-Phosphate into Isoprenol The ability of MDP decarboxylases variants to convert mevalonate-3-phosphate into isoprenol was evaluated using a coupled-enzymatic assay. This assay combines the sequential activities of two MDP decarboxylases, (1) *T. acidophilum* MDP decarboxylase (L200E mutant) catalyses the phosphorylation of mevalonate into mevalonate-3-phosphate; (2) *S. mitis* MDP decarboxylase catalyses the conversion of mevalonate-3-phosphate into isoprenol. This assay was set up in 50 mM Tris-HCl pH7.5, 10 mM MgCl$_2$, 20 mM KCl, 40 mM ATP using 200 mM R,S-sodium mevalonate substrate, 2 mg/ml of *S. mitis* MDP decarboxylase variants and 0.1 mg/ml of *T. acidophilum* MDP decarboxylase (L200E mutant). Negative controls were also prepared without enzymes or with either enzyme. The reaction mixture was incubated in a sealed glass vial for 24 hours at 37° C. isoprenol was extracted by mixing 50 µl of the reaction mix to 100 µl of ethyl acetate. 100 µl of the upper ethyl acetate phase was transferred to a clean vial and analysed by Gas chromatography. Commercial isoprenol was used as a reference. The samples were analysed on a Varian GC-430 gas chromatograph equipped with a flame ionization detector (FID). A 1 µl sample was analysed on a DB-WAX column (30 m, 032×0.50 µm, Agilent) using the following temperature gradient: 2 minutes at 60° C., temperature ramp to 220° C. (20° C./min) and finally 10 minutes at 220° C. In these conditions the retention time of isoprenol was 7.38 min.

It was observed that mutations I160N, R186H, R91H also confer an increase in the activity of *S. mitis* MDP decarboxylase to convert mevalonate-3-phosphate into isoprenol (see FIG. 14). The increase of activity is specific to these particular mutations as an increase in the production was detected on either the "2B4" or "F9" variant template.

Example 5: Butadiene Production from 3-Hydroxypent-4-Enoate Catalyzed by Mutant 2B4 of MDP Decarboxylase from *S. mitis*

The mutant 2B4 is described in Example 2.

(R)-3-hydroxypent-4-enoic acid was synthesized upon request by a company specialized in custom synthesis (Syntheval, France)

The enzymatic reactions were performed under the following conditions:
50 mM Tris-HCl pH 7.5
0-200 mM (R)-3-hydroxypent-4-enoic acid ("R" HPA)
50 mM ATP
20 mM $MgCl_2$
20 mM KCl The pH was adjusted to 7.5

Each assay was started by the addition of a particular purified enzyme to 0.5 ml of reaction mixture. The assays were then incubated with shaking at 37° C. in a 2 ml sealed vial (Interchim). Control reactions were run in parallel. After 20 hours of incubation the butadiene production was analyzed as follows. One ml of the gaseous phase of each assay was collected and directly injected into a Gas Chromatograph GC-450 (Brucker) equipped with a Flame Ionization Detector (FID). Nitrogen was used as carrier gas with a flow rate of 1.5 ml/min. Volatile compounds were chromatographically separated on Rt-Alumina Bond/$Na_2SO_4$ column (30 m, 0.32 mm ID, 5 µm) (Restek) using an isothermal mode at 130° C. The enzymatic reaction product was identified by comparison with 1,3-butadiene standard (Sigma). Under these GC conditions, the retention time for butadiene was 7.4 min.

The results are shown in FIG. 15: No formation of 1,3-butadiene was observed without substrate. The GC analysis of reactions without enzyme showed only traces of butadiene resulted from the thermal decomposition of the 3-hydroxypent-4-enoate. The catalytic tests showed a significant increase of butadiene production in the presence of mutant 2B4 of MOP decarboxylase from *S. mitis*.

Example 6: Butadiene Production from 3-Hydroxypent-4-Enoate Catalyzed by Mutant F9 of MDP Decarboxylase from *S. mitis*

The mutant F9 is described in Example 2.

The enzymatic reactions were performed under the following conditions:
50 mM Tris-HCl pH 7.5
0-200 mM "R" 3-hydroxypent-4-enoic acid ("R" HPA)
50 mM ATP
20 mM $MgCl_2$
20 mM KCl The pH was adjusted to 7.5

Each assay was started by the addition of a particular enzyme to 0.5 ml of reaction mixture. The assays were then incubated with shaking at 37° C. in a 2 ml sealed vial (Interchim). Control reactions were run in parallel. After 20 hours of incubation the butadiene production was analyzed according to the procedure described in Example 5.

The results are shown in FIG. 16: No formation of 1,3-butadiene was observed without substrate. The GC analysis of reactions without enzyme showed only traces of butadiene resulted from the thermal decomposition of the 3-hydroxypent-4-enoate. The catalytic tests showed a significant increase of butadiene production in the presence of mutant F9 of MOP decarboxylase from *S. mitis*.

Example 7: Identification of Variants of *S. mitis* MDP Decarboxylase with Further Increased Activity for the Reaction of Conversion of 3-Phosphonoxyisovalerate into Isobutene Additional MVD variants with a further enhanced activity in converting 3-phosphonoxyisovalerate into isobutene were identified through successive rounds of directed or random mutagenesis, recombination of points mutations and in vitro and/or in vivo screening assay. The list of these MVD variants is presented in the following Table 18.

TABLE 18

| Mutations added to F9 variant | Fold Increase | Screening Assay |
|---|---|---|
| D2H | 1.05 | IN VIVO |
| M42L-D87E-S139C-R186L-K231Q | 1.31 | IN VIVO |
| E164Q-R186V-D252E | 2.15 | IN VIVO |
| D87E-S139C-R186L-K231Q | 2.27 | IN VIVO |
| R186V-Q267R | 2.29 | IN VIVO |
| S139C-R186I | 2.39 | IN VIVO |
| L111M-F122Y-R186L | 2.50 | IN VIVO |
| M75I-R186V | 2.57 | IN VIVO |
| S139A-S141C | 2.60 | IN VIVO |
| K179K-R186V | 2.77 | IN VIVO |
| R186V | 2.78 | IN VIVO |
| A57S-A58T-K77R-R186V | 2.86 | IN VIVO |
| L111M-R186L | 2.94 | IN VIVO |
| R186L | 2.94 | IN VIVO |
| A31S-R186V | 3.03 | IN VIVO |
| S139A-S141G | 3.04 | IN VIVO |
| M75I-R186L-S308T | 3.34 | IN VIVO |
| R186L-S308T | 3.40 | IN VIVO |
| R186I | 3.46 | IN VIVO |
| L111M-R186V-S308T | 3.58 | IN VIVO |
| R186V-D221E | 3.67 | IN VIVO |
| L111M-R186V | 3.77 | IN VIVO |
| M1L-L111M-R186V-S308T | 3.77 | IN VIVO |
| R186N | 4.16 | IN VIVO |
| R24S-G86Q-R186I | 4.30 | IN VIVO |
| I16L-S141P-K241I-K180P-E227K | 20.49 | IN VITRO |
| I16L-S141P-K241I-K180P-D291E-M303L | 22.84 | IN VITRO |
| S141P-K241I-S248T-K180P-R24K | 24.46 | IN VITRO |
| I16L-S141P-K241I-S248T-L297F | 25.01 | IN VITRO |
| I16L-S141P-K241I-S248T-M28K-K180P-L188C-L297F-A246E | 28.17 | IN VITRO |
| I16L-S141P-K241I-S248T-M28K-K180P-L188C-L297F-T242E | 29.87 | IN VITRO |
| I16L-S141P-K241I-S248T-M28K-K180P-L188C-L297F-Y255E | 31.23 | IN VITRO |
| I16L-S141P-K241I-S248T-M28K-K180P-L188C-L297F-T198D | 31.56 | IN VITRO |
| I16L-S141P-K241I-S248T-M28K-K180P-L188C-L297F-K23L | 32.24 | IN VITRO |
| I16L-S141P-K241I-S248T-M28K-K180P-L188C-L297F-K179L | 32.58 | IN VITRO |
| I16L-S141P-K241I-S248T-M28K-K180P-L188C-L297F-K231L | 32.58 | IN VITRO |

TABLE 18-continued

| Mutations added to F9 variant | Fold Increase | Screening Assay |
|---|---|---|
| I16L-S141P-K241I-S248T-M28K-K180P-L188C-L297F-P182E | 32.58 | IN VITRO |
| I16L-S141P-K241I-S248T-M28K-K180P-L188C-L297F-A238E | 32.92 | IN VITRO |
| I16L-S141P-K241I-S248T-M28K-K180P-L188C-L297F-K208L | 32.92 | IN VITRO |
| I16L-S141P-K241I-S248T-M28K-K180P-L188C-L297F-R204L | 32.92 | IN VITRO |
| I16L-S141P-K241I-S248T-M28K-K180P-L188C-L297F-R24L | 32.92 | IN VITRO |
| I16L-S141P-K241I-S248T-M28K-K180P-L188C-L297F | 33.94 | IN VITRO |
| I16L-S141P-K241I-K180P-D291E | 35.32 | IN VITRO |
| I16L-S141P-K241I-S248T-K180P-Q267R-R24K-L118C-L159E | 39.40 | IN VITRO |
| I16L-S141P-K241I-S248T-M28K-K180P-L188C-L297F-S142A | 44.78 | IN VITRO |
| I16L-S141P-K241I-S248T-M28K-K180P-L159E-D291E | 44.94 | IN VITRO |
| I16L-S141P-K241I-S248T-K180P-G166S-R24K | 51.64 | IN VITRO |
| I16L-S141P-K241I-S248T-K180P-R24K | 57.93 | IN VITRO |
| I16L-S141P-K241I-S248T-M28K-K180P-L188C-L297F-Q205H | 67.88 | IN VITRO |

The fold increase is the ratio of MDP decarboxylase variant activity over the "F9" variant MDP decarboxylase activity. The "F9" variant corresponds to the *S. mitis* MDP decarboxylase of SEQ ID NO:1 with the following mutations: K24R-C118L-Y121R-E159L-M173C-E177C-K282C-E291D-F297L-L303M-T308S (see SEQ ID NO:3). The fold increase is determined for one substrate concentration (2 or 6 mM Ply in the in vitro assay and 10 mM HIV in the in vivo assay). The quantity of the enzyme is not normalized but these MVD variants are expressed in similar amounts as observed on SDS-PAGE analysis of cell lysates.

The in vitro screening assay used in present Example 7 is described herein-above in section c of Materials and Methods, wherein, preferably, an in vitro assay involving cell lysates has been used, while the assay has preferably been further miniaturized in 384 deepwell microplates.

For the in vivo testing a further in vivo screening assay has been developed as outlined in the following. This assay is based on the use of a bacterial strain transformed with an expression vector containing the coding sequences and leading to the production of the last two enzymes involved in the metabolic pathway converting acetone to isobutene. More specifically, for the production of 3-phosphonoxyisovalerate (Ply) from the 3-hydroxyisovalerate (HIV), the *T. acidophilum* MDP decarboxylase was used (referred to in the following as HIV phosphorylase) and, for the conversion of PIV into isobutene (IBN), the *S. mitis* MDP decarboxylase variant to be tested was used (referred to in the following as PIV decarboxylase). This strain is first cultured for 24 hours in a shaking incubator at 30° C., 700 rpm, in 300 μL of auto-induction culture medium in 384 deepwell microplates, in order to produce the two types of recombinant enzymes. The cell pellet containing these two overexpressed recombinant enzymes was then resuspended in 50 μL of minimum medium supplemented with 10 mM HIV and incubated further for another four hours in a shaking incubator at 30° C., 700 rpm. During this step, HIV phosphorylase catalyses the phosphorylation of HIV with cellular ATP into Ply, which is then converted into IBN by the PIV decarboxylase variants. The IBN produced is then quantified by gas chromatography using the same method as the in vitro screening assay described above in section c of Materials and Methods.

The invention claimed is:

1. A mevalonate disphosphate (MDP) decarboxylase variant derived from an enzyme with more than 60% sequence identity to the amino acid sequence shown in SEQ ID NO:1, wherein the MDP decarboxylase variant comprises one or more substitutions, deletions and/or insertions at one or more of the positions corresponding to amino acid positions 12, 9, 11, 16, 23, 24, 28, 42, 43, 45, 58, 66, 105, 111, 116, 118, 122, 129, 139, 141, 160, 161, 173, 182, 186, 188, 198, 221, 242, 248, 251, 253, 255, 258, 279, 282, 293, 297, 299, 307, and 308 in the amino acid sequence shown in SEQ ID NO:1 or at a position corresponding to any one of these positions in the sequence having at least 60% sequence identity to SEQ ID NO:1, and wherein said MDP decarboxylase variant is capable of converting 3-phosphonoxy-isovalerate into isobutene with a kcat of more than $0.1 \text{ s}^{-1}$.

2. The MDP decarboxylase variant of claim 1 wherein the MDP decarboxylase variant comprises an amino acid sequence with at least 60% sequence identity to SEQ ID NO:1.

3. The MDP variant of claim 1, wherein:

(1) the MDP variant further comprises a substitution or deletion at an amino acid residue at position 1 in the amino acid sequence shown in SEQ ID NO:1 or at a position corresponding to this position in the sequence having at least 60% sequence identity to SEQ ID NO:1, is deleted or substituted with leucine; and/or (2) the amino acid residue at position 2 in the amino acid sequence shown in SEQ ID NO:1 or at a position corresponding to this position in the sequence having at least 60% sequence identity to SEQ ID NO:1, is deleted or substituted with histidine; and/or
(3) the amino acid residue at position 9 in the amino acid sequence shown in SEQ ID NO:1 or at a position corresponding to this position in the sequence having at least 60% sequence identity to SEQ ID NO:1, is deleted or substituted with leucine; and/or
(4) the amino acid residue at position 11 in the amino acid sequence shown in SEQ ID NO:1 or at a position corresponding to this position in the sequence having at least 60% sequence identity to SEQ ID NO:1, is deleted or substituted with cysteine, glutamic acid or phenylalanine, preferably cysteine; and/or
(5) the amino acid residue at position 16 in the amino acid sequence shown in SEQ ID NO:1 or at a position corresponding to this position in the sequence having at least 60% sequence identity to SEQ ID NO:1, is deleted or substituted with leucine; and/or
(6) the amino acid residue at position 23 in the amino acid sequence shown in SEQ ID NO:1 or at a position corresponding to this position in the sequence having at least 60% sequence identity to SEQ ID NO:1, is deleted or substituted with leucine; and/or
(7) the amino acid residue at position 24 in the amino acid sequence shown in SEQ ID NO:1 or at a position corresponding to this position in the sequence having at least 60% sequence identity to SEQ ID NO:1, is deleted or substituted with arginine, serine, or leucine; and/or
(8) the amino acid residue at position 28 in the amino acid sequence shown in SEQ ID NO:1 or at a position corresponding to this position in the sequence having at least 60% sequence identity to SEQ ID NO:1, is deleted or substituted with lysine or alanine; and/or
(9) the MDP variant further comprises a substitution or deletion at an amino acid residue at position 31 in the amino acid sequence shown in SEQ ID NO:1 or at a position corresponding to this position in the sequence having at least 60% sequence identity to SEQ ID NO:1, is deleted or substituted with serine; and/or
(10) the amino acid residue at position 42 in the amino acid sequence shown in SEQ ID NO:1 or at a position corresponding to this position in the sequence having at least 60% sequence identity to SEQ ID NO:1, is deleted or substituted with alanine or leucine; and/or
(11) the amino acid residue at position 43 in the amino acid sequence shown in SEQ ID NO:1 or at a position corresponding to this position in the sequence having at least 60% sequence identity to SEQ ID NO:1, is deleted or substituted with leucine; and/or
(12) the amino acid residue at position 45 in the amino acid sequence shown in SEQ ID NO:1 or at a position corresponding to this position in the sequence having at least 60% sequence identity to SEQ ID NO:1, is deleted or substituted with leucine, phenylalanine, methionine or valine, preferably leucine; and/or
(13) the MDP variant further comprises a substitution or deletion at an amino acid residue at position 53 in the amino acid sequence shown in SEQ ID NO:1 or at a position corresponding to this position in the sequence having at least 60% sequence identity to SEQ ID NO:1, is deleted or substituted with valine; and/or
(14) the MDP variant further comprises a substitution or deletion at an amino acid residue at position 57 in the amino acid sequence shown in SEQ ID NO:1 or at a position corresponding to this position in the sequence having at least 60% sequence identity to SEQ ID NO:1, is deleted or substituted with serine; and/or
(15) the amino acid residue at position 58 in the amino acid sequence shown in SEQ ID NO:1 or at a position corresponding to this position in the sequence having at least 60% sequence identity to SEQ ID NO:1, is deleted or substituted with threonine; and/or
(16) the amino acid residue at position 66 in the amino acid sequence shown in SEQ ID NO:1 at a position corresponding to this position in the sequence having at least 60% sequence identity to SEQ ID NO:1, is deleted or substituted with histidine; and/or
(17) the MDP variant further comprises a substitution or deletion at an amino acid residue at position 75 in the amino acid sequence shown in SEQ ID NO:1 or at a position corresponding to this position in the sequence having at least 60% sequence identity to SEQ ID NO:1, is deleted or substituted with isoleucine; and/or
(18) the MDP variant further comprise a substitution or deletion at an amino acid residue at position 77 in the amino acid sequence shown in SEQ ID NO:1 or at a position corresponding to this position in the sequence having at least 60% sequence identity to SEQ ID NO:1, is deleted or substituted with asparagine or arginine; and/or
(19) the MDP variant further comprises a substitution or deletion at an amino acid residue at position 80 in the amino acid sequence shown in SEQ ID NO:1 or at a position corresponding to this position in the sequence having at least 60% sequence identity to SEQ ID NO:1, is deleted or substituted with glycine; and/or
(20) the MDP variant further comprises a substitution or deletion at an amino acid residue at position 86 in the amino acid sequence shown in SEQ ID NO:1 or at a position corresponding to this position in the sequence having at least 60% sequence identity to SEQ ID NO:1, is deleted or substituted with glutamine; and/or
(21) the MDP variant further comprises a substitution or deletion at an amino acid residue at position 91 in the amino acid sequence shown in SEQ ID NO:1 or at a position corresponding to this position in the sequence having at least 60% sequence identity to SEQ ID NO:1, is deleted or substituted with histidine; and/or
(22) the amino acid residue at position 105 in the amino acid sequence shown in SEQ ID NO:1 or at a position corresponding to this position in the sequence having at least 60% sequence identity to SEQ ID NO:1, is deleted or substituted with alanine; and/or
(23) the amino acid residue at position 111 in the amino acid sequence shown in SEQ ID NO:1 or at a position corresponding to this position in the sequence having at least 60% sequence identity to SEQ ID NO:1, is deleted or substituted with methionine; and/or
(24) the amino acid residue at position 116 in the amino acid sequence shown in SEQ ID NO:1 or at a position corresponding to this position in the sequence having at least 60% sequence identity to SEQ ID NO:1, is deleted or substituted with arginine, isoleucine, leucine, serine or methionine, preferably arginine or isoleucine; and/or
(25) the amino acid residue at position 118 in the amino acid sequence shown in SEQ ID NO:1 at a position corresponding to this position in the sequence having at least 60% sequence identity to SEQ ID NO:1, is deleted or substituted with leucine or tryptophan; and/or
(26) the MDP variant further comprises a substitution or deletion at an amino acid residue at position 120 in the amino acid sequence shown in SEQ ID NO:1 or at a position corresponding to this position in the sequence having at least 60% sequence identity to SEQ ID NO:1, is deleted or substituted with asparagine, leucine, arginine, isoleucine or valine, preferably asparagine, leucine, arginine or isoleucine; and/or

(27) the MDP variant further comprises a substitution or deletion at an amino acid residue at position 121 in the amino acid sequence shown in SEQ ID NO:1 or at a position corresponding to this position in the sequence having at least 60% sequence identity to SEQ ID NO:1, is deleted or substituted with arginine, leucine, tryptophan, phenylalanine, tyrosine, asparagine or lysine, preferably arginine or phenylalanine; and/or

(28) the amino acid residue at position 122 in the amino acid sequence shown in SEQ ID NO:1 or at a position corresponding to this position in the sequence having at least 60% sequence identity to SEQ ID NO:1, is substituted with methionine or tyrosine; and/or

(29) the MDP variant further comprises a substitution or deletion at an amino acid residue at position 123 in the amino acid sequence shown in SEQ ID NO:1 or at a position corresponding to this position in the sequence having at least 60% sequence identity to SEQ ID NO:1, which is deleted or substituted with methionine or arginine; and/or

(30) the amino acid residue at position 129 in the amino acid sequence shown in SEQ ID NO:1 or at a position corresponding to this position in the sequence having at least 60% sequence identity to SEQ ID NO:1, is deleted or substituted with proline or valine; and/or

(31) the MDP variant further comprises a substitution or deletion at an amino acid residue at position 134 in the amino acid sequence shown in SEQ ID NO:1 or at a position corresponding to this position in the sequence having at least 60% sequence identity to SEQ ID NO:1, is deleted or substituted with glycine; and/or

(32) the amino acid residue at position 139 in the amino acid sequence shown in SEQ ID NO:1 or at a position corresponding to this position in the sequence having at least 60% sequence identity to SEQ ID NO:1, is deleted or substituted with cysteine or alanine; and/or

(33) the amino acid residue at position 141 in the amino acid sequence shown in SEQ ID NO:1 or at a position corresponding to this position in the sequence having at least 60% sequence identity to SEQ ID NO:1, is deleted or substituted with proline, cysteine, glycine or threonine; and/or

(34) the MDP variant further comprises a substitution or deletion at an amino acid residue at position 142 in the amino acid sequence shown in SEQ ID NO:1 or at a position corresponding to this position in the sequence having at least 60% sequence identity to SEQ ID NO:1, is deleted or substituted with alanine; and/or

(35) the MDP variant further comprises a substitution or deletion at an amino acid residue at position 159 in the amino acid sequence shown in SEQ ID NO:1 or at a position corresponding to this position in the sequence having at least 60% sequence identity to SEQ ID NO:1, is deleted or substituted with leucine; and/or

(36) the amino acid residue at position 160 in the amino acid sequence shown in SEQ ID NO:1 or at a position corresponding to this position in the sequence having at least 60% sequence identity to SEQ ID NO:1, is deleted or substituted with valine; and/or

(37) the amino acid residue at position 161 in the amino acid sequence shown in SEQ ID NO:1 or at a position corresponding to this position in the sequence having at least 60% sequence identity to SEQ ID NO:1, is deleted or substituted with arginine; and/or

(38) the MDP variant further comprises a substitution or deletion at an amino acid residue at position 164 in the amino acid sequence shown in SEQ ID NO:1 or at a position corresponding to this position in the sequence having at least 60% sequence identity to SEQ ID NO:1, is deleted or substituted with glutamine; and/or

(39) the MDP variant further comprises a substitution or deletion at an amino acid residue at position 166 in the amino acid sequence shown in SEQ ID NO:1 or at a position corresponding to this position in the sequence having at least 60% sequence identity to SEQ ID NO:1, which is deleted or substituted with serine; and/or

(40) the amino acid residue at position 173 in the amino acid sequence shown in SEQ ID NO:1 or at a position corresponding to this position in the sequence having at least 60% sequence identity to SEQ ID NO:1, is deleted or substituted with cysteine; and/or

(41) the MDP variant further comprises a substitution or deletion at an amino acid residue at position 177 in the amino acid sequence shown in SEQ ID NO:1 or at a position corresponding to this position in the sequence having at least 60% sequence identity to SEQ ID NO:1, is deleted or substituted with valine or cysteine, preferably valine; and/or

(42) the MDP variant further comprises a substitution or deletion at an amino acid residue at position 179 in the amino acid sequence shown in SEQ ID NO:1 or at a position corresponding to this position in the sequence having at least 60% sequence identity to SEQ ID NO:1, is deleted or substituted with lysine or leucine; and/or

(43) the MDP variant further comprises a substitution or deletion at an amino acid residue at position 180 in the amino acid sequence shown in SEQ ID NO:1 or at a position corresponding to this position in the sequence having at least 60% sequence identity to SEQ ID NO:1, is deleted or substituted with proline; and/or

(44) the amino acid residue at position 182 in the amino acid sequence shown in SEQ ID NO:1 or at a position corresponding to this position in the sequence having at least 60% sequence identity to SEQ ID NO:1, is deleted or substituted with glutamic acid; and/or

(45) the amino acid residue at position 186 in the amino acid sequence shown in SEQ ID NO:1 or at a position corresponding to this position in the sequence having at least 60% sequence identity to SEQ ID NO:1, is deleted or substituted with histidine, leucine, valine, isoleucine or asparagine; and/or

(46) the amino acid residue at position 188 in the amino acid sequence shown in SEQ ID NO:1 or at a position corresponding to this position in the sequence having at least 60% sequence identity to SEQ ID NO:1, is deleted or substituted with cysteine; and/or

(47) the amino acid residue at position 198 in the amino acid sequence shown in SEQ ID NO:1 or at a position corresponding to this position in the sequence having at least 60% sequence identity to SEQ ID NO:1, is deleted or substituted with aspartic acid; and/or

(48) the MDP variant further comprises a substitution or deletion at an amino acid residue at position 204 in the amino acid sequence shown in SEQ ID NO:1 or at a position corresponding to this position in the sequence having at least 60% sequence identity to SEQ ID NO:1, is deleted or substituted with leucine; and/or

(49) the MDP variant further comprises a substitution or deletion at an amino acid residue at position 205 in the amino acid sequence shown in SEQ ID NO:1 or at a position corresponding to this position in the sequence having at least 60% sequence identity to SEQ ID NO:1, is deleted or substituted with histidine; and/or

(50) the MDP variant further comprises a substitution or deletion at an amino acid residue at position 208 in the amino acid sequence shown in SEQ ID NO:1 or at a position corresponding to this position in the sequence having at least 60% sequence identity to SEQ ID NO:1, is deleted or substituted with leucine; and/or

(51) the amino acid residue at position 221 in the amino acid sequence shown in SEQ ID NO:1 or at a position corresponding to this position in the sequence having at least 60% sequence identity to SEQ ID NO:1, is deleted or substituted with glutamic acid; and/or

(52) the MDP variant further comprises a substitution or deletion at an amino acid residue at position 227 in the amino acid sequence shown in SEQ ID NO:1 or at a position corresponding to this position in the sequence having at least 60% sequence identity to SEQ ID NO:1, is deleted or substituted with lysine; and/or

(53) the MDP variant further comprises a substitution or deletion at an amino acid residue at position 231 in the amino acid sequence shown in SEQ ID NO:1 or at a position corresponding to this position in the sequence having at least 60% sequence identity to SEQ ID NO:1, is deleted or substituted with glutamine or leucine; and/or

(54) the MDP variant further comprises a substitution or deletion at an amino acid residue at position 238 in the amino acid sequence shown in SEQ ID NO:1 or at a position corresponding to this position in the sequence having at least 60% sequence identity to SEQ ID NO:1, is deleted or substituted with arginine, glutamic acid or lysine; and/or

(55) the MDP variant further comprises a substitution or deletion at an amino acid residue at position 241 in the amino acid sequence shown in SEQ ID NO:1 or at a position corresponding to this position in the sequence having at least 60% sequence identity to SEQ ID NO:1, is deleted or substituted with methionine or isoleucine; and/or

(56) the amino acid residue at position 242 in the amino acid sequence shown in SEQ ID NO:1 or at a position corresponding to this position in the sequence having at least 60% sequence identity to SEQ ID NO:1, is deleted or substituted with alanine or glutamic acid; and/or

(57) the MDP variant further comprises a substitution or deletion at an amino acid residue at position 246 in the amino acid sequence shown in SEQ ID NO:1 or at a position corresponding to this position in the sequence having at least 60% sequence identity to SEQ ID NO:1, is deleted or substituted with glutamic acid; and/or

(58) the amino acid residue at position 248 in the amino acid sequence shown in SEQ ID NO:1 or at a position corresponding to this position in the sequence having at least 60% sequence identity to SEQ ID NO:1, is deleted or substituted with threonine; and/or

(59) the amino acid residue at position 251 in the amino acid sequence shown in SEQ ID NO:1 or at a position corresponding to this position in the sequence having at least 60% sequence identity to SEQ ID NO:1, is deleted or substituted with methionine, phenylalanine or valine, preferably methionine; and/or

(60) the MDP variant further comprises a substitution or deletion at an amino acid residue at position 252 in the amino acid sequence shown in SEQ ID NO:1 or at a position corresponding to this position in the sequence having at least 60% sequence identity to SEQ ID NO:1, is deleted or substituted with glutamic acid; and/or

(61) the amino acid residue at position 253 in the amino acid sequence shown in SEQ ID NO:1 or at a position corresponding to this position in the sequence having at least 60% sequence identity to SEQ ID NO:1, is deleted or substituted with valine or isoleucine; and/or

(62) the amino acid residue at position 255 in the amino acid sequence shown in SEQ ID NO:1 or at a position corresponding to this position in the sequence having at least 60% sequence identity to SEQ ID NO:1, is deleted or substituted with glutamic acid; and/or

(63) the amino acid residue at position 258 in the amino acid sequence shown in SEQ ID NO:1 or at a position corresponding to this position in the sequence having at least 60% sequence identity to SEQ ID NO:1, is deleted or substituted with leucine; and/or

(64) the MDP variant further comprises a substitution or deletion at an amino acid residue at position 264 in the amino acid sequence shown in SEQ ID NO:1 or at a position corresponding to this position in the sequence having at least 60% sequence identity to SEQ ID NO:1, is deleted or substituted with glutamine; and/or

(65) the MDP variant further comprises a substitution or deletion at an amino acid residue at position 267 in the amino acid sequence shown in SEQ ID NO:1 or at a position corresponding to this position in the sequence having at least 60% sequence identity to SEQ ID NO:1, is deleted or substituted with arginine; and/or

(66) the amino acid residue at position 279 in the amino acid sequence shown in SEQ ID NO:1 or at a position corresponding to this position in the sequence having at least 60% sequence identity to SEQ ID NO:1, is deleted or substituted with alanine; and/or

(67) the amino acid residue at position 282 in the amino acid sequence shown in SEQ ID NO:1 or at a position corresponding to this position in the sequence having at least 60% sequence identity to SEQ ID NO:1, is deleted or substituted with cysteine, serine, glutamic acid, glycine, glutamine, threonine, valine, alanine or aspartic acid; and/or

(68) the amino acid residue at position 293 in the amino acid sequence shown in SEQ ID NO:1 or at a position corresponding to this position in the sequence having at least 60% sequence identity to SEQ ID NO:1, is deleted or substituted with phenylalanine or tryptophan; and/or

(69) the amino acid residue at position 297 in the amino acid sequence shown in SEQ ID NO:1 or at a position corresponding to this position in the sequence having at least 60% sequence identity to SEQ ID NO:1, is deleted or substituted with cysteine or leucine, preferably cysteine; and/or

(70) the amino acid residue at position 299 in the amino acid sequence shown in SEQ ID NO:1 or at a position corresponding to this position in the sequence having at least 60% sequence identity to SEQ ID NO:1, is deleted or substituted with proline or lysine; and/or

(71) the MDP variant further comprises a substitution or deletion at an amino acid residue at position 303 in the amino acid sequence shown in SEQ ID NO:1 or at a position corresponding to this position in the sequence having at least 60% sequence identity to SEQ ID NO:1, is deleted or substituted with methionine; and/or

(72) the amino acid residue at position 307 in the amino acid sequence shown in SEQ ID NO:1 or at a position corresponding to this position in the sequence having at least 60% sequence identity to SEQ ID NO:1, is deleted or substituted with histidine; and/or
(73) the amino acid residue at position 308 in the amino acid sequence shown in SEQ ID NO:1 or at a position corresponding to this position in the sequence having at least 60% sequence identity to SEQ ID NO:1, is deleted or substituted with serine.

4. The MDP decarboxylase variant of claim 1, wherein the amino acid residue at position 282 in the amino acid sequence shown in SEQ ID NO:1 or at a position corresponding to this position in the sequence having at least 60% sequence identity to SEQ ID NO:1 is substituted with another amino acid residue or deleted.

5. The MDP decarboxylase variant of claim 4, wherein at least one further amino acid residue is substituted or deleted at a position corresponding to amino acid positions 1, 2, 9, 11, 16, 23, 24, 28, 31, 42, 43, 45, 53, 57, 58, 66, 75, 77, 80, 86, 87, 91, 105, 111, 116, 118, 120, 121, 122, 123, 129, 134, 139, 141, 142, 159, 160, 161, 164, 166, 173, 177, 179, 180, 182, 186, 188, 198, 204, 205, 208, 215, 221, 227, 231, 238, 241, 242, 246, 248, 251, 252, 253, 255, 258, 264, 267, 279, 291, 293, 297, 299, 303, 307, 308, and 315 in SEQ ID NO:1 or at a position corresponding to this position in the sequence having at least 60% sequence identity to SEQ ID NO:1.

6. The MDP decarboxylase variant of claim 1, wherein at least one further amino acid residue is substituted or deleted at a position corresponding to amino acid positions 1, 2, 9, 11, 16, 23, 24, 28, 31, 42, 45, 53, 57, 58, 75, 80, 86, 87, 111, 116, 118, 120, 121, 122, 123, 129, 139, 141, 142, 159, 161, 164, 166, 173, 177, 179, 180, 182, 188, 198, 204, 205, 208, 215, 221, 227, 231, 238, 241, 242, 246, 248, 251, 252, 253, 255, 264, 267, 279, 291, 293, 297, 299, 303, 307, 308, and 315 in SEQ ID NO:1 or at a position corresponding to this position in the sequence having at least 60% sequence identity to SEQ ID NO:1.

7. The MDP decarboxylase variant of claim 4, wherein the amino acid residues at position 121 in the amino acid sequence shown in SEQ ID NO:1 or at a position corresponding to this position in the sequence having at least 60% sequence identity to SEQ ID NO:1 is deleted or substituted with another amino acid residue.

8. The MDP decarboxylase variant of claim 1 comprising the amino acid sequence as shown in SEQ ID NO: 1 wherein the following substitutions have been effected:
K24R-C118L-Y121R-E159L-M173C-E177C-K282C-E291D-F297L-L303M-T308S.

9. The MDP decarboxylase variant of claim 8, further comprising the following additional substitutions:
S141P-I16L-K241I-S248T-M28K-K180P.

10. The MDP decarboxylase variant of claim 8, further comprising the following additional substitutions:
S141P-I16L-R91H-K241M-S248T-Q299K.

11. The MDP decarboxylase variant of claim 1 comprising an amino acid sequence as shown in SEQ ID NO: 1 wherein the following substitutions have been effected:
Y121R-E159L-M173C-K282C-L303M-T308S.

12. A nucleic acid molecule encoding the MDP decarboxylase variant of claim 1.

13. A vector comprising the nucleic acid molecule of claim 12.

14. A host cell comprising the nucleic acid molecule of claim 12.

15. A method of producing isobutene, isoprenol, or 1,3 butadiene comprising
(a) enzymatically converting by the MDP decarboxylase variant of claim 1:
(1) 3-hydroxyisovalerate or 3-phosphonoxyisovalerate into isobutene; or
(2) mevalonate or mevalonate-3-phosphate into isoprenol; or
(3) 3-hydroxypent-4-enoate or 3-phosphonoxypent-4-enoate into 1,3-butadiene; and
(b) recovering said isobutene, isoprenol, or 1,3 butadiene.

16. The method of claim 15, wherein the method comprises enzymatically converting 3-hydroxyisovalerate or 3-phosphonoxyisovalerate into isobutene by the MDP decarboxylase variant of claim 1.

17. The method of claim 16, wherein the method comprises the steps of:
(i) culturing the host cell of claim 14 in a suitable medium comprising 3-hydroxyisovalerate or 3-phosphonoxyisovalerate; and
(ii) recovering the produced isobutene.

18. The method of claim 15, wherein the method comprises enzymatically converting mevalonate or mevalonate-3-phosphate into isoprenol by the MDP decarboxylase variant of claim 1.

19. The method of claim 18, wherein the method comprises the steps of:
(i) culturing the host cell of claim 14 in a suitable medium comprising mevalonate or mevalonate-3-phosphate; and
(ii) recovering the produced isoprenol.

20. The method of claim 15, wherein the method comprises enzymatically converting 3-hydroxypent-4-enoate or 3-phosphonoxypent-4-enoate into 1,3-butadiene by the MDP decarboxylase variant of claim 1.

21. The method of claim 20, wherein the method comprises the steps of:
(i) culturing the host cell of claim 14 in a suitable medium comprising 3-hydroxypent-4-enoate or 3-phosphonoxypent-4-enoate; and
(ii) recovering the produced 1,3-butadiene.

22. The MDP decarboxylase variant of claim 3, wherein at least one further amino acid residue is substituted or deleted at a position corresponding to amino acid positions 1, 2, 9, 11, 16, 23, 24, 28, 31, 42, 45, 53, 57, 58, 75, 80, 86, 87, 111, 116, 118, 120, 121, 122, 123, 129, 139, 141, 142, 159, 161, 164, 166, 173, 177, 179, 180, 182, 188, 198, 204, 205, 208, 215, 221, 227, 231, 238, 241, 242, 246, 248, 251, 252, 253, 255, 264, 267, and 315 in SEQ ID NO:1 or at a position corresponding to this position in the sequence having at least 60% sequence identity to SEQ ID NO:1.

* * * * *

SEQUENCE LISTING

<160> NUMBER OF SEQ ID NOS: 23

<210> SEQ ID NO 1
<211> LENGTH: 317
<212> TYPE: PRT
<213> ORGANISM: Streptococcus mitis
<220> FEATURE:
<223> OTHER INFORMATION: Strain B6

<400> SEQUENCE: 1

```
Met Asp Arg Glu Pro Val Thr Val Arg Ser Tyr Ala Asn Ile Ala Ile
1               5                   10                  15

Ile Lys Tyr Trp Gly Lys Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Ser Leu Pro Thr Asp Ala Thr Ala Asp Ala Phe Tyr Ile Asn Gly
    50                  55                  60

Gln Leu Gln Asn Glu Ala Glu His Val Lys Met Ser Lys Ile Ile Asp
65                  70                  75                  80

Arg Tyr Arg Pro Asp Gly Asp Gly Phe Val Arg Ile Asp Thr Gln Asn
                85                  90                  95

Ser Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asn Arg
        115                 120                 125
```

```
Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Gly Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
            195                 200                 205

Asp Tyr Gln Asp Met Leu Val Tyr Leu Lys Ala Asn Asp Phe Ala Lys
    210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gln Gly Glu Ala Cys Tyr
            260                 265                 270

Phe Thr Met Asp Ala Gly Pro Asn Val Lys Val Leu Cys Gln Glu Lys
            275                 280                 285

Asp Leu Glu His Leu Ser Glu Ile Phe Gly Gln Arg Tyr Arg Leu Ile
    290                 295                 300

Val Ser Lys Thr Lys Asp Leu Ser Gln Asp Gly Cys Cys
305                 310                 315

<210> SEQ ID NO 2
<211> LENGTH: 317
<212> TYPE: PRT
<213> ORGANISM: Artificial Sequence
<220> FEATURE:
<223> OTHER INFORMATION: Mutant 2B4 of MDP decarboxylase

<400> SEQUENCE: 2

Met Asp Arg Glu Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Ser Leu Pro Thr Asp Ala Thr Ala Asp Phe Tyr Ile Asn Gly
    50                  55                  60

Gln Leu Gln Asn Glu Ala Glu His Val Lys Met Ser Lys Ile Ile Asp
65                  70                  75                  80

Arg Tyr Arg Pro Asp Gly Asp Gly Phe Val Arg Ile Asp Thr Gln Asn
                85                  90                  95

Ser Met Pro Thr Ala Ala Gly Leu Ser Ser Ser Ser Gly Leu Ser
            100                 105                 110

Ala Leu Val Lys Ala Cys Asn Ala Arg Phe Lys Leu Gly Leu Asn Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Leu Ile
145                 150                 155                 160

Tyr Pro Val Glu Thr Gly Leu Lys Leu Ala Met Ile Cys Leu Val Leu
                165                 170                 175
```

```
Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
            195                 200                 205

Asp Tyr Gln Asp Met Leu Val Tyr Leu Lys Ala Asn Asp Phe Ala Lys
            210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
            245                 250                 255

Ala Met Asp Phe Val Arg Gln Leu Arg Glu Gln Gly Glu Ala Cys Tyr
            260                 265                 270

Phe Thr Met Asp Ala Gly Pro Asn Val Cys Val Leu Cys Gln Glu Lys
            275                 280                 285

Asp Leu Glu His Leu Ser Glu Ile Phe Gly Gln Arg Tyr Arg Met Ile
            290                 295                 300

Val Ser Lys Ser Lys Asp Leu Ser Gln Asp Gly Cys Cys
305                 310                 315

<210> SEQ ID NO 3
<211> LENGTH: 317
<212> TYPE: PRT
<213> ORGANISM: Artificial Sequence
<220> FEATURE:
<223> OTHER INFORMATION: Mutant F9 of MDP decarboxylase

<400> SEQUENCE: 3

Met Asp Arg Glu Pro Val Thr Val Arg Ser Tyr Ala Asn Ile Ala Ile
1               5                   10                  15

Ile Lys Tyr Trp Gly Lys Lys Arg Glu Lys Glu Met Val Pro Ala Thr
            20                  25                  30

Ser Ser Ile Ser Leu Thr Leu Glu Asn Met Tyr Thr Glu Thr Thr Leu
            35                  40                  45

Ser Ser Leu Pro Thr Asp Ala Thr Asp Ala Phe Tyr Ile Asn Gly
        50                  55                  60

Gln Leu Gln Asn Glu Ala Glu His Val Lys Met Ser Lys Ile Ile Asp
65                  70                  75                  80

Arg Tyr Arg Pro Asp Gly Asp Gly Phe Val Arg Ile Asp Thr Gln Asn
            85                  90                  95

Ser Met Pro Thr Ala Ala Gly Leu Ser Ser Ser Ser Gly Leu Ser
            100                 105                 110

Ala Leu Val Lys Ala Leu Asn Ala Arg Phe Lys Leu Gly Leu Asn Arg
            115                 120                 125

Ser Gln Leu Ala Gln Glu Ala Lys Phe Ala Ser Gly Ser Ser Arg
            130                 135                 140

Ser Phe Tyr Gly Pro Leu Gly Ala Trp Asp Lys Asp Ser Gly Leu Ile
145                 150                 155                 160

Tyr Pro Val Glu Thr Gly Leu Lys Leu Ala Met Ile Cys Leu Val Leu
            165                 170                 175

Cys Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
            195                 200                 205

Asp Tyr Gln Asp Met Leu Val Tyr Leu Lys Ala Asn Asp Phe Ala Lys
            210                 215                 220
```

```
Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
            245                 250                 255

Ala Met Asp Phe Val Arg Gln Leu Arg Glu Gln Gly Glu Ala Cys Tyr
        260                 265                 270

Phe Thr Met Asp Ala Gly Pro Asn Val Cys Val Leu Cys Gln Glu Lys
    275                 280                 285

Asp Leu Asp His Leu Ser Glu Ile Leu Gly Gln Arg Tyr Arg Met Ile
290                 295                 300

Val Ser Lys Ser Lys Asp Leu Ser Gln Asp Gly Cys Cys
305                 310                 315
```

<210> SEQ ID NO 4
<211> LENGTH: 957
<212> TYPE: DNA
<213> ORGANISM: Streptococcus mitis
<220> FEATURE:
<221> NAME/KEY: source
<222> LOCATION: (1)..(957)
<223> OTHER INFORMATION: /mol_type="unassigned DNA"
      /organism="Streptococcus mitis"

<400> SEQUENCE: 4

```
atggatcgtg aaccggttac cgttcgtagc tatgcaaata ttgccatcat caaatattgg      60
ggcaaaaaaa aagaaaaaga aatggttccg gcaaccagca gcattagcct gaccctggaa     120
aatatgtata ccgaaaccac cctgagcagc ctgccgaccg atgcaaccgc agatgcattt     180
tatattaatg gtcagctgca gaacgaagcc gaacatgtta aaatgagcaa atcatcgat      240
cgctatcgtc cggatggtga tggttttgtt cgtattgata cccagaatag tatgccgacc     300
gcagcaggtc tgagcagcag cagcagtggt ctgagcgcac tggttaaagc atgtaatgcc     360
tattttaaac tgggtctgaa tcgtagccag ctggcacaag aagcaaaatt tgcaagcggt     420
agcagcagcc gtagctttta tggtccgctg ggtgcatggg ataaagatag cggtgaaatt     480
tatccggttg aaaccggtct gaaactggca atgattatgc tggttctgga agataaaaaa     540
aaaccgatta gcagccgtga tggtatgaaa ctgtgtgttg aaaccagcac cacctttgat     600
gattgggttc gtcagagcga aaaagattat caggatatgc tggtgtacct gaaagcaaat     660
gattttgcca agttggtga gctgaccgaa aaaaatgcac tggcaatgca cgcaaccacc     720
aaaaccgcaa gtccggcatt tagctatctg accgatgcaa gctatgaagc aatggatttt     780
gttcgtcagc tgcgtgaaca gggtgaagca tgttacttta caatggatgc aggtccgaat     840
gttaaagttc tgtgccaaga aaaagacctg gaacatctga gcgaaatttt tggtcagcgt     900
tatcgtctga ttgtgagcaa aaccaaagat ctgagccagg atggttgctg ttaataa       957
```

<210> SEQ ID NO 5
<211> LENGTH: 314
<212> TYPE: PRT
<213> ORGANISM: Streptococcus anginosus
<220> FEATURE:
<223> OTHER INFORMATION: Strain SK52

<400> SEQUENCE: 5

```
Met Asp Arg Lys Ser Val Lys Val Arg Ser Tyr Ala Asn Ile Ala Ile
1               5                   10                  15

Ile Lys Tyr Trp Gly Lys Lys Asp Thr Val Lys Ile Ile Pro Ala Thr
            20                  25                  30
```

-continued

```
Ser Ser Ile Ser Leu Thr Leu Glu Asn Met Tyr Thr Glu Thr Thr Leu
        35                  40                  45

Ser Ser Leu Pro Val Ser Ala Gln Ser Asp Glu Phe Tyr Ile Asn Gly
 50                  55                  60

Val Leu Gln Asp Gln Ala Glu His Lys Lys Met Ser Asn Ile Val Asp
 65                  70                  75                  80

Arg Phe Arg Pro Gln Gly Ala Gly Phe Val Arg Ile Asp Thr Lys Asn
                 85                  90                  95

Asn Met Pro Thr Ala Ala Gly Leu Ser Ser Ser Ser Gly Leu Ser
            100                 105                 110

Ala Leu Val Lys Ala Cys Asn Asp Phe Phe Glu Leu His Leu Ser Thr
            115                 120                 125

Lys Glu Gln Ala Gln Lys Ala Lys Leu Ala Ser Gly Ser Ser Arg
130                 135                 140

Ser Phe Tyr Gly Pro Ile Ala Ala Trp Asp Lys Asp Ser Gly Glu Ile
145                 150                 155                 160

Tyr Pro Val Lys Thr Asp Leu Lys Leu Ala Met Ile Met Leu Val Leu
                165                 170                 175

Tyr Asp Gln Lys Lys Pro Ile Ser Ser Arg Glu Gly Met Lys Arg Cys
            180                 185                 190

Ala Glu Thr Ser Thr Thr Phe Ser Asp Trp Val Arg Gln Ser Glu Glu
            195                 200                 205

Asp Tyr Lys Ala Met Leu Thr Tyr Leu Ser Asn Asn Asp Phe Ala Lys
            210                 215                 220

Val Gly Glu Leu Thr Glu Lys Asn Ala Leu Ala Met His Ala Thr Thr
225                 230                 235                 240

Gln Thr Ala Thr Pro Ala Phe Ser Tyr Leu Thr Glu Lys Ser Tyr Glu
                245                 250                 255

Ala Met Asp Phe Ile Lys Gln Leu Arg Ser Gln Gly Glu Arg Cys Tyr
            260                 265                 270

Phe Thr Met Asp Ala Gly Pro Asn Val Lys Val Leu Cys Leu Glu Glu
            275                 280                 285

Asp Leu Glu His Leu Val Pro Ile Phe Ala Glu Lys Tyr Arg Leu Ile
            290                 295                 300

Val Ser Lys Thr Lys Glu Leu Pro Asp Asp
305                 310

<210> SEQ ID NO 6
<211> LENGTH: 315
<212> TYPE: PRT
<213> ORGANISM: Streptococcus gordonii
<220> FEATURE:
<223> OTHER INFORMATION: Strain Challis / ATCC 35105 / BCRC 15272 /
      CH1 / DL1 / V288

<400> SEQUENCE: 6

Met Asp Arg Lys Pro Val Ser Val Lys Ser Tyr Ala Asn Ile Ala Ile
 1               5                  10                  15

Val Lys Tyr Trp Gly Lys Lys Asp Ala Glu Lys Met Ile Pro Ser Thr
                20                  25                  30

Ser Ser Ile Ser Leu Thr Leu Glu Asn Met Tyr Thr Glu Thr Gln Leu
            35                  40                  45

Ser Pro Leu Pro Asp Thr Ala Thr Gly Asp Glu Phe Tyr Ile Asp Gly
 50                  55                  60

Gln Leu Gln Ser Pro Ala Glu His Ala Lys Ile Ser Lys Ile Ile Asp
 65                  70                  75                  80
```

Arg Phe Arg Ser Pro Glu Asp Gly Phe Val Arg Val Asp Thr Ser Asn
             85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Thr
            115                 120                 125

Glu Glu Leu Ala Gln Leu Ala Lys Phe Ala Ser Gly Ser Ser Ala Arg
130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
            195                 200                 205

Asp Tyr Gln Ala Met Leu Gly Tyr Leu Gln Asp Asn Asp Phe Ala Lys
            210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
            275                 280                 285

Asp Leu Asp His Leu Ala Ala Ile Phe Glu Lys Asp Tyr Arg Leu Ile
            290                 295                 300

Val Ser Lys Thr Lys Asp Leu Ser Asp Glu Ser
305                 310                 315

<210> SEQ ID NO 7
<211> LENGTH: 315
<212> TYPE: PRT
<213> ORGANISM: Streptococcus sanguinis
<220> FEATURE:
<223> OTHER INFORMATION: Strain SK330

<400> SEQUENCE: 7

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Gly Thr Gln Leu
            35                  40                  45

Ser Pro Leu Pro Asp Ser Ala Thr Gly Asp Glu Phe Tyr Ile Asp Gly
        50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Thr
            115                 120                 125

Gln Glu Leu Ala Gln Leu Ala Lys Phe Ala Ser Gly Ser Ser Ala Arg
            130                 135                 140

Ser Phe Phe Gly Pro Leu Ala Ala Trp Asp Lys Asp Ser Gly Val Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Thr Gln Ser Ala Leu
        195                 200                 205

Asp Tyr Gln Ala Met Leu Gly Tyr Leu Arg Asp Asn Asp Phe Val Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
        275                 280                 285

Asp Leu Asp His Leu Val Ala Ile Phe Glu Lys Asp Tyr Arg Leu Ile
    290                 295                 300

Val Ser Lys Thr Lys Asp Leu Ser Asp Glu Gly
305                 310                 315

<210> SEQ ID NO 8
<211> LENGTH: 316
<212> TYPE: PRT
<213> ORGANISM: Streptococcus australis
<220> FEATURE:
<223> OTHER INFORMATION: Strain ATCC 700641

<400> SEQUENCE: 8

Met Asp Arg Lys Pro Val Ser Val Lys Ser Tyr Ala Asn Ile Ala Ile
1               5                   10                  15

Ile Lys Tyr Trp Gly Lys Glu Asn Ser Glu Ala Met Val Pro Ser Thr
            20                  25                  30

Ser Ser Ile Ser Leu Thr Leu Glu Asn Met Tyr Thr Glu Thr Arg Leu
        35                  40                  45

Ser Pro Leu Gly Pro Glu Ala Lys Ser His Ala Phe Phe Ile Asp Gly
    50                  55                  60

Val Phe Gln Asn Glu Ala Glu Gln Ala Lys Ile Gly Ala Val Ile Asp
65                  70                  75                  80

Arg Phe Lys Pro Glu Gly Glu Thr Gly Phe Val Arg Val Asp Thr Ser
                85                  90                  95

Asn Asn Met Pro Thr Ala Ala Gly Leu Ser Ser Ser Ser Ser Gly Leu
            100                 105                 110

Ser Ala Leu Val Lys Ala Cys Asn Cys Tyr Tyr Gln Leu Gly Met Thr
        115                 120                 125

Gln Ala Glu Gln Ala Gln Ala Lys Phe Ala Ser Gly Ser Ser Ser
    130                 135                 140

Arg Ser Phe Phe Gly Pro Leu Ala Ala Trp Asp Lys Asp Thr Gly Glu
145                 150                 155                 160

Ile Tyr Gln Val Glu Thr Asp Leu Lys Leu Ala Met Ile Met Leu Val
                165                 170                 175

Leu Asn Asp Gln Gln Lys Ile Leu Ser Ser Arg Glu Gly Met Lys Arg
            180                 185                 190

Cys Thr Glu Thr Ser Ser Asn Phe Gln Glu Trp Ile Arg Gln Ser Ala
        195                 200                 205

Gln Asp Tyr Gln Asp Met Leu Ala Tyr Leu Lys Asp Asn Asp Phe Glu
    210                 215                 220

Lys Val Gly Glu Leu Thr Glu Arg Asn Ala Leu Leu Met His Ser Thr
225                 230                 235                 240

Thr Lys Thr Ala Ser Pro Ala Phe Ser Tyr Leu Thr Asp Lys Ser Tyr
                245                 250                 255

Glu Ala Met Glu Phe Val Arg Ser Leu Arg Asn Glu Gly Lys Arg Cys
            260                 265                 270

Tyr Phe Thr Met Asp Ala Gly Pro Asn Val Lys Val Leu Cys Leu Glu
        275                 280                 285

Glu Asp Leu Asp Gln Leu Val Pro Leu Phe Glu Gln Asp Tyr Arg Ile
    290                 295                 300

Ile Val Ser Lys Thr Lys Asp Leu Ser His Glu Asp
305                 310                 315

<210> SEQ ID NO 9
<211> LENGTH: 314
<212> TYPE: PRT
<213> ORGANISM: Streptococcus agalactiae
<220> FEATURE:
<223> OTHER INFORMATION: Strain ATCC 13813 / DSM 2134 / JCM 5671 / NCIMB
      701348 / NCTC 8181

<400> SEQUENCE: 9

Met Asp Gly Lys Ser Ile Ser Val Lys Ser Tyr Ala Asn Ile Ala Ile
1               5                   10                  15

Ile Lys Tyr Trp Gly Lys Ala Asp Ala Glu Lys Met Ile Pro Ala Thr
            20                  25                  30

Ser Ser Ile Ser Leu Thr Leu Glu Asn Met Tyr Thr Glu Thr Arg Leu
        35                  40                  45

Thr Ala Leu Gly Lys Asp Ala Lys Lys Asp Glu Phe Tyr Ile Ser Gly
    50                  55                  60

Val Leu Gln Asn Asp His Glu His Asp Lys Met Ser Ala Ile Leu Asp
65                  70                  75                  80

Arg Phe Arg Gln Asn Lys Ser Gly Phe Val Lys Ile Glu Thr Thr Asn
                85                  90                  95

Asn Met Pro Thr Ala Ala Gly Leu Ser Ser Ser Ser Gly Leu Ser
            100                 105                 110

Ala Leu Val Lys Ala Cys Asn Asp Phe Phe Gly Thr Asn Leu Ser Gln
        115                 120                 125

Ser Gln Leu Ala Gln Glu Ala Lys Phe Ala Ser Gly Ser Ser Ser Arg
    130                 135                 140

Ser Phe Phe Gly Pro Val Ala Ala Trp Asp Lys Asp Ser Gly Asp Ile
145                 150                 155                 160

Tyr Lys Val His Thr Asp Leu Asp Leu Ala Met Ile Met Leu Val Leu
                165                 170                 175

Asn Asp Lys Arg Lys Pro Ile Ser Ser Arg Glu Gly Met Lys Ile Cys
            180                 185                 190

Thr Glu Thr Ser Thr Thr Phe Asn Glu Trp Val Arg Gln Ser Glu Gln
        195                 200                 205

Asp Tyr Gln Asp Met Leu Val Tyr Leu Lys Asn Asn Asp Phe Gln Lys

```
            210                 215                 220
Val Gly Gln Leu Thr Glu Arg Asn Ala Leu Ala Met His Ser Thr Thr
225                 230                 235                 240

Lys Thr Ala Thr Pro Ala Phe Ser Tyr Leu Thr Glu Thr Tyr Lys
                245                 250                 255

Ala Met Asp Val Val Lys Lys Leu Arg Glu Lys Gly His Glu Cys Tyr
                260                 265                 270

Tyr Thr Met Asp Ala Gly Pro Asn Val Lys Val Leu Cys Leu Arg Gln
            275                 280                 285

Asp Leu Asp Ala Leu Ala Thr Ile Leu Glu Gln Asp Tyr Arg Ile Ile
        290                 295                 300

Val Ser Thr Thr Lys Glu Leu Ala Asp Gly
305                 310
```

<210> SEQ ID NO 10
<211> LENGTH: 316
<212> TYPE: PRT
<213> ORGANISM: Streptococcus gallolyticus
<220> FEATURE:
<223> OTHER INFORMATION: Strain ATCC BAA-2069

<400> SEQUENCE: 10

```
Met Asp Arg Lys Ile Val Thr Val Lys Ser Tyr Ala Asn Ile Ala Ile
1               5                   10                  15

Ile Lys Tyr Trp Gly Lys Ala Asp Ala Val Lys Met Ile Pro Ala Thr
                20                  25                  30

Ser Ser Ile Ser Leu Thr Leu Glu Asn Met Phe Thr Thr Thr Thr Val
            35                  40                  45

Ser Phe Leu Pro Gln Ser Val Gly His Asp Glu Phe Tyr Ile Asn Gly
        50                  55                  60

Val Leu Gln Asp Glu Lys Glu His Ala Lys Ile Ser Ala Ile Ile Asp
65                  70                  75                  80

Gln Tyr Arg Gly Gly Arg Ser Glu Phe Val Arg Val Glu Thr Ser Asn
                85                  90                  95

Asn Met Pro Thr Ala Ala Gly Leu Ser Ser Ser Ser Ser Gly Leu Ser
                100                 105                 110

Ala Leu Val Lys Ala Cys Asn Glu Leu Phe Glu Thr Gly Leu Asn Gln
            115                 120                 125

Ser Glu Leu Ala Gln Lys Ala Lys Phe Ala Ser Gly Ser Ser Ser Arg
        130                 135                 140

Ser Phe Phe Gly Pro Ile Ala Ala Trp Asp Lys Asp Ser Gly Asp Ile
145                 150                 155                 160

Tyr Pro Val Gln Thr Asp Leu Lys Leu Ala Met Ile Met Leu Val Leu
                165                 170                 175

Ser Asp Ser Lys Lys Pro Ile Ser Ser Arg Glu Gly Met Lys Arg Cys
            180                 185                 190

Ala Glu Thr Ser Thr Thr Phe Ala Asp Trp Val Lys Gln Ser Glu Gln
        195                 200                 205

Asp Tyr Lys Asp Met Leu Ala Tyr Leu Lys Ala Asn Asp Phe Glu Lys
        210                 215                 220

Val Gly Glu Leu Thr Glu Arg Asn Ala Leu Ala Met His Asp Thr Asn
225                 230                 235                 240

Thr His Ala Asn Pro Pro Phe Asn Tyr Leu Thr Asp Lys Thr Tyr Ala
                245                 250                 255

Ala Met Asp Phe Val Lys Ser Leu Arg Ala Gln Gly Glu Lys Cys Tyr
```

```
                    260                 265                 270
Phe Thr Met Asp Ala Gly Pro Asn Val Lys Val Leu Cys Leu Glu Glu
            275                 280                 285

Asp Leu Glu Arg Leu Thr Lys Arg Phe Glu Glu Asn Tyr Arg Val Ile
        290                 295                 300

Ala Ser Arg Thr Lys Val Leu Pro Asp Glu Asn Asp
305                 310                 315

<210> SEQ ID NO 11
<211> LENGTH: 314
<212> TYPE: PRT
<213> ORGANISM: Streptococcus uberis
<220> FEATURE:
<223> OTHER INFORMATION: Strain ATCC BAA-854 / 0140J

<400> SEQUENCE: 11

Met Asp Pro Lys Thr Val Thr Val Lys Ser Tyr Ala Asn Ile Ala Ile
1               5                   10                  15

Ile Lys Tyr Trp Gly Lys Glu Asn Gln Glu Lys Met Ile Pro Ser Thr
            20                  25                  30

Ser Ser Ile Ser Leu Thr Leu Glu Asn Met Tyr Thr Glu Thr Ser Leu
        35                  40                  45

Lys Arg Leu Asp His Gly Ala Gln Lys Asp Leu Phe Tyr Ile Asp Asp
    50                  55                  60

His Leu Gln Asp Gln Ala Glu His Gln Lys Ile Ser Ala Ile Ile Asp
65                  70                  75                  80

Gln Phe Arg Thr Asp Lys Asn Gln Phe Val Glu Val Arg Thr Arg Asn
                85                  90                  95

Asn Met Pro Thr Ala Ala Gly Leu Ser Ser Ser Ser Ser Gly Leu Ser
            100                 105                 110

Ala Leu Val Lys Ala Cys Asn Leu Phe Phe Asp Cys Arg Leu Asn Gln
        115                 120                 125

Lys Glu Leu Ala Gln Lys Ala Lys Phe Ala Ser Gly Ser Ala Ser Arg
    130                 135                 140

Ser Phe Phe Gly Pro Leu Ser Ala Trp Asp Lys Asp Ser Gly Asp Ile
145                 150                 155                 160

Tyr Gln Val Glu Thr Asp Leu Lys Leu Ala Met Ile Met Leu Val Val
                165                 170                 175

Asn Asp Ala Arg Lys Pro Ile Ser Ser Arg Glu Gly Met Lys Leu Cys
            180                 185                 190

Arg Glu Thr Ser Thr Thr Phe Asp Gln Trp Ile Gln Gln Ser Glu Gln
        195                 200                 205

Asp Tyr Gln Glu Met Leu Leu Tyr Leu Lys Asn Asn Asp Phe Glu Lys
    210                 215                 220

Val Gly Gln Leu Thr Glu Lys Asn Ala Leu Ala Met His Ala Thr Thr
225                 230                 235                 240

Arg Thr Ala Lys Pro Ser Phe Ser Tyr Leu Thr Glu Asp Ser Tyr Gln
                245                 250                 255

Ala Met Asp Lys Val Lys Ala Leu Arg Glu Glu Gly Phe Gln Cys Tyr
            260                 265                 270

Phe Thr Met Asp Ala Gly Pro Asn Val Lys Val Leu Cys Leu Glu Lys
        275                 280                 285

Asp Leu Asp Ser Leu Ser Lys Arg Phe Ala Glu Asp Tyr Ser Ile Ile
    290                 295                 300

Val Ser Lys Thr Lys Glu Ile Ser His Asp
305                 310
```

```
                            305                 310

<210> SEQ ID NO 12
<211> LENGTH: 316
<212> TYPE: PRT
<213> ORGANISM: Streptococcus equinus
<220> FEATURE:
<223> OTHER INFORMATION: Strain ATCC 9812

<400> SEQUENCE: 12

Met Asp Arg Lys Ile Val Thr Val Lys Ser Tyr Ala Asn Ile Ala Ile
1               5                   10                  15

Ile Lys Tyr Trp Gly Lys Ala Asp Ala Ala Lys Met Ile Pro Ala Thr
            20                  25                  30

Ser Ser Ile Ser Leu Thr Leu Glu Asn Met Phe Thr Thr Thr Ser Val
        35                  40                  45

Ser Phe Leu Pro Asp Thr Ala Thr His Asp Glu Phe Tyr Ile Asn Gly
    50                  55                  60

Val Leu Gln Asp Glu Lys Glu His Ala Lys Ile Ser Ala Ile Ile Asp
65                  70                  75                  80

Gln Tyr Arg Gly Gln Arg Thr Glu Phe Val Lys Val Glu Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Glu Leu Phe Glu Thr Gly Leu Thr Gln
        115                 120                 125

Ala Glu Leu Ala Gln Lys Ala Lys Phe Ala Ser Gly Ser Ser Ser Arg
    130                 135                 140

Ser Phe Phe Gly Pro Leu Ala Ala Trp Asp Lys Asp Thr Gly Glu Val
145                 150                 155                 160

Tyr Gln Val Glu Thr Asp Leu Lys Leu Gly Met Ile Met Leu Val Leu
                165                 170                 175

Ser Asp Ser Lys Lys Pro Ile Ser Ser Arg Glu Gly Met Lys Arg Cys
            180                 185                 190

Val Glu Thr Ser Thr Thr Phe Glu Asn Trp Val Lys Gln Ser Glu Gln
        195                 200                 205

Asp Tyr Lys Asp Met Leu Gly Tyr Leu Lys Asn Asn Asp Phe Glu Arg
    210                 215                 220

Val Gly Glu Leu Thr Glu Arg Asn Ala Leu Ala Met His Asp Thr Asn
225                 230                 235                 240

Thr His Ala Asn Pro Pro Phe Asn Tyr Leu Thr Glu Glu Ser Tyr Lys
                245                 250                 255

Ala Met Asp Phe Val Lys Gln Leu Arg Ala Glu Gly Glu Lys Cys Tyr
            260                 265                 270

Phe Thr Met Asp Ala Gly Pro Asn Val Lys Val Leu Cys Leu Glu Glu
        275                 280                 285

Asp Leu Glu Arg Leu Thr Lys Arg Phe Glu Glu Asn Tyr Arg Ala Ile
    290                 295                 300

Val Ser Arg Thr Lys Glu Leu Pro Asp Glu Asn Asp
305                 310                 315

<210> SEQ ID NO 13
<211> LENGTH: 314
<212> TYPE: PRT
<213> ORGANISM: Streptococcus pyogenes
<220> FEATURE:
<223> OTHER INFORMATION: Strain ATCC 10782
```

-continued

```
<400> SEQUENCE: 13

Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
            20                  25                  30

Ser Ser Ile Ser Leu Thr Leu Glu Asn Met Phe Thr Thr Thr Ser Ile
        35                  40                  45

Ser Phe Leu Pro Asp Thr Ala Thr Ser Asp Gln Phe Tyr Ile Asn Gly
    50                  55                  60

Val Leu Gln Asn Asp Glu Glu His Thr Lys Ile Ser Ala Ile Ile Asp
65                  70                  75                  80

Gln Phe Arg Gln Pro Gly Gln Ala Phe Val Lys Met Glu Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asp Gln Leu Phe Asn Thr Gln Leu Asp Gln
        115                 120                 125

Lys Ala Leu Ala Gln Lys Ala Lys Phe Ala Ser Gly Ser Ser Ser Arg
    130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
            180                 185                 190

Arg Asp Thr Ser Thr Thr Phe Asp Glu Trp Val Glu Gln Ser Ala Ile
        195                 200                 205

Asp Tyr Gln His Met Leu Thr Tyr Leu Lys Thr Asn Asn Phe Glu Lys
    210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Thr Lys Glu Ser Tyr Gln
                245                 250                 255

Ala Met Glu Ala Val Lys Glu Leu Arg Gln Glu Gly Phe Ala Cys Tyr
            260                 265                 270

Phe Thr Met Asp Ala Gly Pro Asn Val Lys Val Leu Cys Leu Glu Lys
        275                 280                 285

Asp Leu Ala Gln Leu Ala Glu Arg Leu Gly Lys Asn Tyr Arg Ile Ile
    290                 295                 300

Val Ser Lys Thr Lys Asp Leu Pro Asp Val
305                 310

<210> SEQ ID NO 14
<211> LENGTH: 314
<212> TYPE: PRT
<213> ORGANISM: Streptococcus pyogenes

<400> SEQUENCE: 14

Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
            20                  25                  30

Ser Ser Ile Ser Leu Thr Leu Glu Asn Met Phe Thr Thr Thr Ser Val
        35                  40                  45
```

```
Ser Phe Leu Pro Asp Thr Ala Thr Ser Asp Gln Phe Tyr Ile Asn Gly
         50                  55                  60

Val Leu Gln Asn Asp Glu Glu His Thr Lys Ile Ser Thr Ile Ile Asp
 65                  70                  75                  80

Gln Phe Arg Gln Pro Gly Gln Ala Phe Val Lys Met Glu Thr Gln Asn
                 85                  90                  95

Asn Met Pro Thr Ala Ala Gly Leu Ser Ser Ser Ser Gly Leu Ser
            100                 105                 110

Ala Leu Val Lys Ala Cys Asp Gln Leu Phe Asp Thr Gln Leu Asp Gln
            115                 120                 125

Lys Ala Leu Ala Gln Lys Ala Lys Phe Ala Ser Gly Ser Ser Ser Arg
130                 135                 140

Ser Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
                180                 185                 190

Arg Asp Thr Ser Thr Thr Phe Asp Glu Trp Val Glu Gln Ser Ala Ile
                195                 200                 205

Asp Tyr Gln His Met Leu Thr Tyr Leu Lys Thr Asn Asn Phe Glu Lys
210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Thr Lys Glu Ser Tyr Gln
                245                 250                 255

Ala Met Glu Ala Val Lys Glu Leu Arg Gln Glu Gly Phe Ala Cys Tyr
            260                 265                 270

Phe Thr Met Asp Ala Gly Pro Asn Val Lys Val Leu Cys Leu Glu Lys
            275                 280                 285

Asp Leu Ala Gln Leu Ala Glu Arg Leu Gly Lys Asn Tyr Arg Ile Ile
            290                 295                 300

Val Ser Lys Thr Lys Asp Leu Pro Asp Val
305                 310

<210> SEQ ID NO 15
<211> LENGTH: 313
<212> TYPE: PRT
<213> ORGANISM: Leptotrichia goodfellowii
<220> FEATURE:
<223> OTHER INFORMATION: Strain F0264

<400> SEQUENCE: 15

Met Asp Thr Lys Ser Val Arg Ser Tyr Ala Asn Ile Ala Ile Ile Lys
 1               5                  10                  15

Tyr Trp Gly Lys Lys Asp Ala Lys Asn Met Ile Pro Ala Thr Ser Ser
                 20                  25                  30

Ile Ser Leu Thr Leu Glu Asn Met Tyr Thr Asp Thr Glu Ile Ser Phe
             35                  40                  45

Ile Glu Ser Glu Thr Asp Val Phe Tyr Leu Asn Gly Val Leu Gln Asp
         50                  55                  60

Ser Lys Gln Thr Glu Lys Ile Ser Lys Val Val Asp Leu Phe Arg Glu
 65                  70                  75                  80

Asn Lys Glu Gln Lys Val Leu Ile Lys Ser Glu Asn Asn Met Pro Thr
                 85                  90                  95
```

```
Glu Ala Gly Leu Ser Ser Ser Ser Gly Leu Ser Ala Leu Ile Lys
            100                 105                 110

Ala Cys Asn Lys Leu Phe Arg Lys Asn Met Thr Arg Thr Glu Leu Ala
        115                 120                 125

Arg Ile Ser Lys Tyr Gly Ser Gly Ser Ser Ala Arg Ser Phe Phe Gly
    130                 135                 140

Pro Ile Gly Ala Trp Asp Lys Asp Thr Gly Glu Ile Tyr Glu Ile Lys
145                 150                 155                 160

Thr Asp Leu Lys Leu Ala Met Ile Met Leu Val Leu Asn Glu Glu Lys
                165                 170                 175

Lys Ile Ile Ser Ser Arg Glu Gly Met Lys Leu Cys Gly Glu Thr Ser
            180                 185                 190

Thr Ile Phe Asp Lys Trp Ile Lys Asn Ser Glu Ile Glu Tyr Glu Glu
        195                 200                 205

Met Lys Lys Ala Leu Ala Glu Asn Asn Phe Glu Lys Val Gly Glu Leu
    210                 215                 220

Thr Glu Lys Asn Ala Leu Ala Met His Glu Thr Thr Leu Tyr Ala Asn
225                 230                 235                 240

Pro Pro Phe Ser Tyr Leu Thr Asp Lys Ser Arg Glu Ala Met Glu Phe
                245                 250                 255

Val Lys Lys Leu Arg Lys Ser Gly Glu Lys Cys Tyr Phe Thr Met Asp
            260                 265                 270

Ala Gly Pro Asn Val Lys Val Leu Cys Leu Glu Lys Asp Phe Glu Lys
        275                 280                 285

Leu Lys Tyr Val Leu Gly Lys Lys Tyr Lys Ile Ile Ala Ser Lys Thr
    290                 295                 300

Lys Val Ile Thr Asp Glu Asn Asn Gly
305                 310

<210> SEQ ID NO 16
<211> LENGTH: 317
<212> TYPE: PRT
<213> ORGANISM: Streptococcus peroris
<220> FEATURE:
<223> OTHER INFORMATION: Strain ATCC 700780

<400> SEQUENCE: 16

Met Asp Arg Lys Pro Val Thr Val Arg Ser Tyr Ala Asn Ile Ala Ile
1               5                   10                  15

Ile Lys Tyr Trp Gly Lys Lys Asn Glu Lys Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Thr Asp Ala Lys Ala Asp Ala Phe Tyr Ile Asn Gly
    50                  55                  60

Gln Leu Gln Asn Glu Ala Glu His Ala Lys Met Ser Lys Ile Ile Asp
65                  70                  75                  80

Arg Tyr Arg Pro Glu Gly Ala Gly Phe Val Arg Ile Asp Thr Lys Asn
                85                  90                  95

Asn Met Pro Thr Ala Ala Gly Leu Ser Ser Ser Ser Gly Leu Ser
            100                 105                 110

Ala Leu Val Lys Val Cys Asn Ala Tyr Phe Gln Leu Gly Leu Asn Arg
        115                 120                 125

Lys Glu Leu Ala Leu Glu Ala Lys Phe Ala Ser Gly Ser Ser Ser Arg
    130                 135                 140
```

```
Ser Phe Tyr Gly Pro Leu Ala Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Gln Lys Lys Pro Ile Ser Ser Arg Asp Gly Met Lys Leu Cys
            180                 185                 190

Val Glu Thr Ser Thr Thr Phe Glu Asp Trp Val Arg Gln Ser Glu Gln
        195                 200                 205

Asp Tyr Lys Asp Met Leu Ser Tyr Leu Lys Glu Asn Asp Phe Lys Lys
    210                 215                 220

Val Gly Glu Leu Thr Glu Lys Asn Ala Leu Ala Met His Ala Thr Thr
225                 230                 235                 240

Lys Thr Ala Thr Pro Ser Phe Ser Tyr Leu Thr Asp Ala Ser Tyr Glu
                245                 250                 255

Ala Met Asp Phe Val Arg Gln Leu Arg Glu Gln Gly Glu Ser Cys Tyr
                260                 265                 270

Phe Thr Met Asp Ala Gly Pro Asn Val Lys Val Leu Cys Leu Glu Glu
            275                 280                 285

Asp Leu Glu His Leu Ser Glu Leu Leu Gly Gln Arg Tyr Arg Leu Ile
        290                 295                 300

Val Ser Lys Thr Lys Asp Leu Ser Gln Asp Asp Ala Cys
305                 310                 315

<210> SEQ ID NO 17
<211> LENGTH: 317
<212> TYPE: PRT
<213> ORGANISM: Streptococcus infantis
<220> FEATURE:
<223> OTHER INFORMATION: Strain ATCC 700779

<400> SEQUENCE: 17

Met Asp Arg Lys Pro Val Thr Val Arg Ser Tyr Ala Asn Ile Ala Ile
1               5                   10                  15

Ile Lys Tyr Trp Gly Lys Lys Ala Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Ala Asp Ala Thr Ala Asp Ala Phe Tyr Ile Asn Gly
    50                  55                  60

Gln Leu Gln Asn Glu Ala Glu His Ala Lys Met Arg Lys Ile Ile Asp
65                  70                  75                  80

Arg Tyr Arg Pro Glu Gly Ala Gly Phe Val Arg Ile Asp Thr Lys Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Leu Gly Leu Asn Arg
        115                 120                 125

Arg Glu Leu Ala Leu Glu Ala Lys Phe Ala Ser Gly Ser Ser Ser Arg
    130                 135                 140

Ser Phe Tyr Gly Pro Leu Ala Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Gln Lys Lys Pro Ile Ser Ser Arg Asp Gly Met Lys Leu Cys
            180                 185                 190
```

```
Val Glu Thr Ser Thr Thr Phe Asp Glu Trp Ile Arg Gln Ser Glu Gln
            195                 200                 205

Asp Tyr Lys Asp Met Leu Val Tyr Leu Lys Glu Asn Asp Phe Lys Lys
        210                 215                 220

Val Gly Glu Leu Thr Glu Lys Asn Ala Leu Ala Met His Ala Thr Thr
225                 230                 235                 240

Lys Thr Ala Thr Pro Ser Phe Ser Tyr Leu Thr Asp Ala Ser Tyr Glu
                245                 250                 255

Ala Met Asp Phe Val Arg Gln Leu Arg Glu Lys Gly Glu Ser Cys Tyr
            260                 265                 270

Phe Thr Met Asp Ala Gly Pro Asn Val Lys Val Leu Cys Leu Glu Lys
        275                 280                 285

Asp Phe Glu His Leu Ser Glu Leu Leu Gly Gln Arg Tyr Arg Leu Ile
    290                 295                 300

Val Ser Lys Thr Lys Asp Leu Ser Gln Asp Asp Asp Cys
305                 310                 315

<210> SEQ ID NO 18
<211> LENGTH: 317
<212> TYPE: PRT
<213> ORGANISM: Streptococcus infantis
<220> FEATURE:
<223> OTHER INFORMATION: Strain SK1076

<400> SEQUENCE: 18

Met Asp Arg Lys Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Ala Asp Ala Ser Ser Asp Ala Phe Tyr Ile Asn Gly
    50                  55                  60

Gln Leu Gln Asn Glu Ala Glu His Val Lys Met Ser Lys Ile Ile Asp
65                  70                  75                  80

Arg Tyr Arg Pro Glu Gly Ala Gly Ser Val Arg Ile Asp Thr Lys Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Leu Gly Leu Asn Arg
        115                 120                 125

Lys Glu Leu Ala Leu Glu Ala Lys Phe Ala Ser Gly Ser Ser Ser Arg
    130                 135                 140

Ser Phe Tyr Gly Pro Leu Ala Ala Trp Asp Lys Asp Ser Gly Glu Ile
145                 150                 155                 160

Tyr Pro Val Glu Thr Asp Leu Lys Leu Ser Met Ile Met Leu Val Leu
                165                 170                 175

Glu Asp Gln Lys Lys Pro Ile Ser Ser Arg Asp Gly Met Lys Leu Cys
            180                 185                 190

Val Glu Thr Ser Thr Thr Phe Glu Glu Trp Ile Arg Gln Ser Glu Gln
        195                 200                 205

Asp Tyr Lys Asp Met Leu Ile Tyr Leu Lys Glu Asn Asp Phe Glu Lys
    210                 215                 220

Val Gly Ala Leu Thr Glu Lys Asn Ala Leu Ala Met His Ala Thr Thr
225                 230                 235                 240
```

```
Lys Thr Ala Asn Pro Pro Phe Ser Tyr Leu Thr Asp Ala Ser Tyr Glu
                245                 250                 255

Ala Met Asp Phe Val Arg Gln Leu Arg Glu Gln Gly Glu Ser Cys Tyr
            260                 265                 270

Phe Thr Met Asp Ala Gly Pro Asn Val Lys Val Leu Cys Leu Glu Lys
        275                 280                 285

Asp Leu Glu His Leu Ser Glu Leu Leu Gly Gln His Tyr Arg Leu Ile
    290                 295                 300

Val Ser Lys Thr Lys Asp Leu Ser Gln Asp Asp Cys
305                 310                 315

<210> SEQ ID NO 19
<211> LENGTH: 317
<212> TYPE: PRT
<213> ORGANISM: Streptococcus mitis
<220> FEATURE:
<223> OTHER INFORMATION: Strain SK321

<400> SEQUENCE: 19

Met Asp Arg Glu Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Ser Leu Pro Thr Asp Ala Lys Ala Asp Ala Phe Tyr Ile Asn Gly
    50                  55                  60

Gln Leu Gln Asn Glu Ala Glu His Ala Lys Met Ser Lys Ile Ile Asp
65                  70                  75                  80

Arg Tyr Arg Pro Ala Gly Glu Gly Phe Ile Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asp Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Val Tyr Leu Lys Glu Asn Asp Phe Thr Lys
    210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gln Gly Glu Ser Cys Tyr
            260                 265                 270

Phe Thr Met Asp Ala Gly Pro Asn Val Lys Val Leu Cys Gln Glu Lys
        275                 280                 285
```

Asp Leu Glu His Leu Ser Glu Ile Phe Gly Gln Arg Tyr Arg Leu Ile
    290                 295                 300

Val Ser Lys Thr Lys Asp Leu Ser Gln Asp Asp Cys Cys
305                 310                 315

<210> SEQ ID NO 20
<211> LENGTH: 344
<212> TYPE: PRT
<213> ORGANISM: Unknown
<220> FEATURE:
<223> OTHER INFORMATION: Streptococcus species Strain M334

<400> SEQUENCE: 20

Met Tyr His Ser Leu Gly Arg Gln Phe Asn Thr Arg Thr Arg Thr Ser
1               5                   10                  15

Arg Lys Ile Arg Arg Glu Arg Ser Cys Ser Asp Met Asp Arg Glu Pro
                20                  25                  30

Val Thr Val Arg Ser Tyr Ala Asn Ile Ala Ile Ile Lys Tyr Trp Gly
            35                  40                  45

Lys Lys Gln Glu Lys Glu Met Val Pro Ala Thr Ser Ser Ile Ser Leu
    50                  55                  60

Thr Leu Glu Asn Met Tyr Thr Glu Thr Thr Leu Ser Pro Leu Pro Thr
65                  70                  75                  80

Asp Ala Thr Ala Asp Val Phe Tyr Ile Asn Gly Gln Leu Gln Asn Glu
                85                  90                  95

Ala Glu His Ala Lys Met Ser Lys Ile Ile Asp Arg Tyr Arg Pro Ala
            100                 105                 110

Gly Glu Gly Phe Val Arg Ile Asp Thr Gln Asn Asn Met Pro Thr Ala
        115                 120                 125

Ala Gly Leu Ser Ser Ser Ser Gly Leu Ser Ala Leu Val Lys Ala
    130                 135                 140

Cys Asn Ala Tyr Phe Gln Leu Gly Leu Asp Arg Ser Gln Leu Ala Gln
145                 150                 155                 160

Glu Ala Lys Phe Ala Ser Gly Ser Ser Arg Ser Phe Tyr Gly Pro
                165                 170                 175

Leu Gly Ala Trp Asp Lys Asp Ser Gly Glu Ile Tyr Pro Val Glu Thr
            180                 185                 190

Asp Leu Lys Leu Ala Met Ile Met Leu Val Leu Glu Asp Lys Lys Lys
        195                 200                 205

Pro Ile Ser Ser Arg Asp Gly Met Lys Leu Cys Val Glu Thr Ser Thr
    210                 215                 220

Thr Phe Asp Asp Trp Val Arg Gln Ser Glu Lys Asp Tyr Gln Asn Met
225                 230                 235                 240

Leu Val Tyr Leu Lys Gly Asn Asp Phe Ala Lys Val Gly Glu Leu Thr
                245                 250                 255

Glu Lys Asn Ala Leu Ala Met His Ala Thr Thr Lys Thr Ala Ser Pro
            260                 265                 270

Ala Phe Ser Tyr Leu Thr Asp Ala Ser Tyr Glu Ala Met Asp Phe Val
        275                 280                 285

Arg Gln Leu Arg Glu Gln Gly Glu Ala Cys Tyr Phe Thr Met Asp Ala
    290                 295                 300

Gly Pro Asn Val Lys Val Leu Cys Gln Glu Lys Asp Leu Glu His Leu
305                 310                 315                 320

Ser Glu Ile Phe Gly Gln Arg Tyr Arg Leu Ile Val Ser Lys Thr Lys
                325                 330                 335

Asp Leu Ser Gln Asp Asp Cys Cys
            340

<210> SEQ ID NO 21
<211> LENGTH: 317
<212> TYPE: PRT
<213> ORGANISM: Streptococcus sanguinis
<220> FEATURE:
<223> OTHER INFORMATION: Strain ATCC 49296

<400> SEQUENCE: 21

Met Asp Arg Lys Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Thr Asp Ala Thr Ala Asp Ala Phe Tyr Ile Asn Gly
    50                  55                  60

Gln Leu Gln Ser Glu Ala Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Leu Gly Leu Asn Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Arg Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Val Tyr Leu Lys Glu Asn Asp Phe Ala Asn
    210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gly Glu Ala Cys Tyr
            260                 265                 270

Phe Thr Met Asp Ala Gly Pro Asn Val Lys Val Leu Cys Gln Glu Lys
        275                 280                 285

Asp Leu Glu His Leu Ser Glu Ile Phe Gly Gln Arg Tyr Arg Leu Ile
    290                 295                 300

Val Ser Lys Thr Lys Asp Leu Ser Gln Asp Asp Cys Cys
305                 310                 315

<210> SEQ ID NO 22
<211> LENGTH: 317
<212> TYPE: PRT
<213> ORGANISM: Streptococcus oralis
<220> FEATURE:
<223> OTHER INFORMATION: Strain ATCC 35037

<400> SEQUENCE: 22

Met Asp Arg Lys Pro Val Thr Val Arg Ser Tyr Ala Asn Ile Ala Ile
1               5                   10                  15

Ile Lys Tyr Trp Gly Lys Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Thr Asp Ala Thr Ala Asp Ala Phe Tyr Ile Asn Gly
    50                  55                  60

Gln Leu Gln Asn Glu Ala Glu His Ala Lys Ile Ser Lys Ile Ile Asn
65                  70                  75                  80

Arg Tyr Arg Pro Glu Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Leu Gly Leu Asp Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asn Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Leu Tyr Leu Lys Glu Asn Asp Phe Thr Lys
    210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val His Gln Leu Arg Glu Gln Gly Glu Ala Cys Tyr
            260                 265                 270

Phe Thr Met Asp Ala Gly Pro Asn Val Lys Val Leu Cys Gln Glu Lys
        275                 280                 285

Asp Leu Glu His Leu Ser Glu Ile Phe Gly Gln Arg Tyr Arg Leu Ile
    290                 295                 300

Val Ser Lys Thr Lys Asp Leu Ser Gln Asp Asp Cys Cys
305                 310                 315

<210> SEQ ID NO 23
<211> LENGTH: 344
<212> TYPE: PRT
<213> ORGANISM: Streptococcus pneumoniae
<220> FEATURE:
<223> OTHER INFORMATION: Strain ATCC BAA-255 / R6

<400> SEQUENCE: 23

Met Tyr His Ser Leu Gly Asn Gln Phe Asp Thr Arg Thr Arg Thr Ser
1               5                   10                  15

Arg Lys Ile Arg Arg Glu Arg Ser Cys Ser Asp Met Asp Arg Glu Pro

-continued

```
                    20                  25                  30
Val Thr Val Arg Ser Tyr Ala Asn Ile Ala Ile Ile Lys Tyr Trp Gly
        35                  40                  45
Lys Lys Lys Glu Lys Glu Met Val Pro Ala Thr Ser Ser Ile Ser Leu
    50                  55                  60
Thr Leu Glu Asn Met Tyr Thr Glu Thr Thr Leu Ser Pro Leu Pro Ala
65                  70                  75                  80
Asn Val Thr Ala Asp Glu Phe Tyr Ile Asn Gly Gln Leu Gln Asn Glu
                85                  90                  95
Val Glu His Ala Lys Met Ser Lys Ile Ile Asp Arg Tyr Arg Pro Ala
            100                 105                 110
Gly Glu Gly Phe Val Arg Ile Asp Thr Gln Asn Asn Met Pro Thr Ala
            115                 120                 125
Ala Gly Leu Ser Ser Ser Ser Gly Leu Ser Ala Leu Val Lys Ala
            130                 135                 140
Cys Asn Ala Tyr Phe Lys Leu Gly Leu Asp Arg Ser Gln Leu Ala Gln
145                 150                 155                 160
Glu Ala Lys Phe Ala Ser Gly Ser Ser Ser Arg Ser Phe Tyr Gly Pro
                165                 170                 175
Leu Gly Ala Trp Asp Lys Asp Ser Gly Glu Ile Tyr Pro Val Glu Thr
                180                 185                 190
Asp Leu Lys Leu Ala Met Ile Met Leu Val Leu Glu Asp Lys Lys Lys
            195                 200                 205
Pro Ile Ser Ser Arg Asp Gly Met Lys Leu Cys Val Glu Thr Ser Thr
        210                 215                 220
Thr Phe Asp Asp Trp Val Arg Gln Ser Glu Lys Asp Tyr Gln Asp Met
225                 230                 235                 240
Leu Ile Tyr Leu Lys Glu Asn Asp Phe Ala Lys Ile Gly Glu Leu Thr
                245                 250                 255
Glu Lys Asn Ala Leu Ala Met His Ala Thr Thr Lys Thr Ala Ser Pro
            260                 265                 270
Ala Phe Ser Tyr Leu Thr Asp Ala Ser Tyr Glu Ala Met Asp Phe Val
        275                 280                 285
Arg Gln Leu Arg Glu Lys Gly Glu Ala Cys Tyr Phe Thr Met Asp Ala
        290                 295                 300
Gly Pro Asn Val Lys Val Phe Cys Gln Glu Lys Asp Leu Glu His Leu
305                 310                 315                 320
Ser Glu Ile Phe Gly Gln Arg Tyr Arg Leu Ile Val Ser Lys Thr Lys
                325                 330                 335
Asp Leu Ser Gln Asp Asp Cys Cys
            340
```